US008541386B2

(12) United States Patent
Klein et al.

(10) Patent No.: US 8,541,386 B2
(45) Date of Patent: Sep. 24, 2013

(54) CANNABINOID 2 ($CB_2$) RECEPTOR GENE PROMOTER AND UNIQUE RNA TRANSCRIPTS IN B CELLS AND METHODS OF USE

(75) Inventors: Thomas W. Klein, Tampa, FL (US); Tracy Sherwood, Riverview, FL (US); Liang Nong, Tampa, FL (US); Cathy Newton, Land O'Lakes, FL (US)

(73) Assignee: University of South Florida, Tampa, FL (US)

(*) Notice: Subject to any disclaimer, the term of this patent is extended or adjusted under 35 U.S.C. 154(b) by 200 days.

(21) Appl. No.: 12/859,744

(22) Filed: Aug. 19, 2010

(65) Prior Publication Data

US 2011/0092567 A1 Apr. 21, 2011

Related U.S. Application Data

(60) Provisional application No. 61/235,326, filed on Aug. 19, 2009.

(51) Int. Cl.
*C12N 15/113* (2010.01)
*C07H 21/04* (2006.01)

(52) U.S. Cl.
USPC ...................................................... 514/44 A

(58) Field of Classification Search
None
See application file for complete search history.

(56) References Cited

U.S. PATENT DOCUMENTS

| | | | |
|---|---|---|---|
| 2005/0202077 A1* | 9/2005 | Watson et al. | 424/450 |
| 2006/0293262 A1* | 12/2006 | Lieberman et al. | 514/44 |
| 2007/0129367 A1 | 6/2007 | Eatherton et al. | |
| 2010/0056758 A1* | 3/2010 | Deveaux et al. | 530/387.1 |

OTHER PUBLICATIONS

Agudelo, M. et al. "Cannabinoid Receptor 2 ($CB_2$) Mediates Immunoglobulin Class Switching from IgM to IgE in Cultures of Murine-Purified B Lymphocytes" *J Neuroimmune Pharmacol*, 2008, 3:35-42.
Carayon, P. et al. "Modulation and Functional Involvement of CB2 Peripheral Cannabinoid Receptors During B-Cell Differentiation" *Blood*, Nov. 1998, 92(10):3605-3615.
Feng, W. et al. "Expression of CB2 cannabinoid receptor in *Pichia pastoris*" *Protein Expression and Purification*, 2002, 26:496-505.
Galiègue, S. et al. "Expression of central and peripheral cannabinoid receptors in human immune tissues and leukocyte subpopulations" *Eur. J. Biochem.*, 1995, 232:54-61.
Gong, J.P. et al. "Cannabinoid CB2 receptors: Immunohistochemical localization in rat brain" *Brain Research*, 2006, 1071:10-23.
Jordá, M.A. et al. "Hematopoietic cells expressing the peripheral cannabinoid receptor migrate in response to the endocannabinoid 2-arachidonoylglycerol" *Blood*, Apr. 2002, 99(8):2786-2793.

Jordá, M.A. et al. "Identification, Characterization, and Function of a Novel Oncogene the Peripheral Cannabinoid Receptor Cb2" *Ann. N.Y. Acad. Sci.*, 2003, 996:10-16.
Juven-Gershon, T. et al. "Perspectives on the RNA polymerase II core promoter" *Biochemical Society Transactions*, 2006, 34(6):1047-1050.
Kreth, S. et al. "Differential expression of 5'-UTR splice variants of the adenosine $A_{2A}$ receptor gene in human granulocytes: identification, characterization, and functional impact on activation" *The FASEB Journal*, Sep. 2008, 22:3276-3286.
Lee, S.F. et al. "Differential expression of cannabinoid $CB_2$ receptor mRNA in mouse immune cell subpopulations and following B cell stimulation" *European Journal of Pharmacology*, 2001, 423:235-241.
Lee, S.F. et al. "Downregulation of Cannabinoid receptor 2 (CB2) Messenger RNA Expression During in vitro Stimulation of Murine Splenocytes with Lipopolysaccharide" *Advances in Experimental Medicine and Biology*, 2001, 493:223-228.
Marchand, J. et al. "Quantitative Method to Determine mRNA Levels by Reverse Transcriptase-Polymerase Chain Reaction from Leukocyte Subsets Purified by Fluorescence-Activated Cell Sorting: Application to Peripheral Cannabinoid Receptors" *Cytometry*, 1999, 35:227-234.
Massi, P. et al. "Immune function alterations in mice tolerant to $\Delta^9$-tetrahydrocannabinol: functional and biochemical parameters" *Journal of Neuroimmunology*, 1998, 92:60-66.
Munro, S. et al. "Molecular characterization of a peripheral receptor for cannabinoids" *Nature*, Sep. 1993, 365:61-65.
Newton, C.A. et al. "Secondary Immunity to *Legionella pneumophila* and Th1 Activity Are Suppressed by Delta-9-Tetrahydrocannabinol Injection" *Infection and Immunity*, Sep. 1994, 62(9):4015-4020.
Pereira, J.P. et al. "Cannabinoid receptor 2 mediates retention of immature B cells in bone marrow sinusoids" *Nat Immunol.*, Apr. 2009, 10(4):403-411.
Rayman, N. et al. "Distinct Expression Profiles of the Peripheral Cannabinoid Receptor in Lymphoid Tissues Depending on Receptor Activation Status" *J Immunol*, 2004, 172:2111-2117.
Sandelin, A. et al. "Mammalian RNA polymerase II core promoters: insights from genome-wide studies" *Nature Reviews*, Jun. 2007, 8:424-436.

(Continued)

*Primary Examiner* — Tracy Vivlemore
(74) *Attorney, Agent, or Firm* — Saliwanchik, Lloyd & Eisenschenk

(57) ABSTRACT

Cannabinoid receptor 2 ($CB_2$) is expressed in B lymphocytes and is involved in immune regulation. Mouse splenic B cells express three $CB_2$ transcripts utilizing two different first exons. Human peripheral blood B cells express one $CB_2$ transcript utilizing one first exon. Alignment of sequenced RACE products to either the mouse or human genome reveals that isolated transcripts contain previously unidentified transcriptional start sites (TSS). B cells from mouse and human preferentially express one transcript, exon 1a in mouse and exon 1 in human. Multiple $CB_2$ TSSs are utilized in mouse splenic B cells and one TSS in human peripheral blood B cells. The defining of the receptor gene TSSs in these cells provides materials and methods for therapeutically regulating immune function, including antibody isotype switching, using compounds such as inhibitory nucleic acids that downregulate expression of the B cell $CB_2$ gene (e.g., RNAi molecules).

18 Claims, 32 Drawing Sheets

(56) References Cited

OTHER PUBLICATIONS

Schroder, A.J. et al. "Cutting Edge: STAT6 Serves as a Positive and Negative Regulator of Gene Expression in IL-4-Stimulated B Lymphocytes" *J Immunol*, 2002, 168:996-1000.

Sherwood, T.A. et al. "Identification of Transcription Start Sites and Preferential Expression of Select $CB_2$ Transcripts in Mouse and Human B Lymphocytes" *J Neuroimmune Pharmacol*, 2009, 4:476-488.

Takhar, P. et al. "Allergen Drives Class Switching to IgE in the Nasal Mucosa in Allergic Rhinitis" *J Immunol*, 2005, 174:5024-5032.

The Encode Project Consortium "Identification and analysis of functional elements in 1% of the human genome by the ENCODE pilot project" *Nature*, Jun. 2007, 447(7146):799-816.

Thieu, V.T. et al. "IL-4-stimulated NF-κB activity is required for Stat6 DNA binding" *Journal of Leukocyte Biology*, Aug. 2007, 82:370-379.

Turner, J.D. et al. "Tissue specific glucocorticoid receptor expression, a role for alternative first exon usage?" *Biochemical Pharmacology*, 2006, 72:1529-1537.

Yarden, G. et al. "Characterization of sINR, a strict version of the Initiator core promoter element" *Nucleic Acids Research*, 2009, 37(13):4234-4246.

Newton, CA and Klein, TW, "Cannabinoid 2 (CB2) Receptor Involvement in the Down-regulation but not Up-regulation of Serum IgE Levels in Immunized Mice" *The Journal of Neuroimmune Pharmacology*, 2012, 7:591-598.

Sherwood, T, "Characterization of cannabinoid receptor 2 transcript expression in B cells" *Graduate School Theses and Dissertations*, 2010, http://scholarcommons.usf.edu/etd/1767.

GenBank Accession No. FJ357036, version FJ357036.1, GI: 227433957, Sherwood et al., 2009.

* cited by examiner

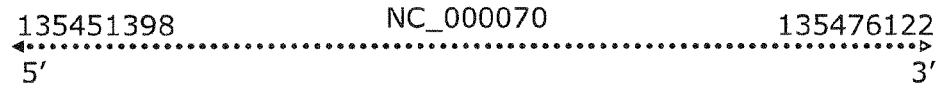
FIG. 1A
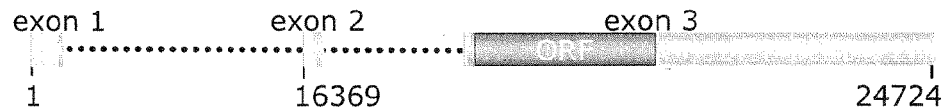
FIG. 1B
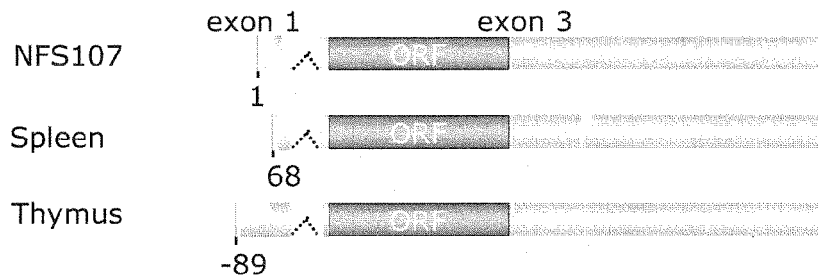
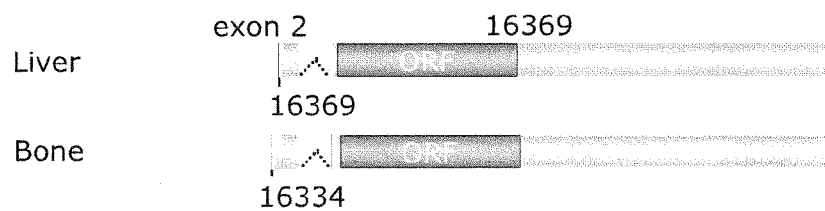
FIG. 1C

Human chromosome 1; 1p36.11
FIG. 2A
hCNR2 gene, 39.3 kb
exon 2 ......................................... exon 1
| | |
39358  37665                                    1
FIG. 2B
hCB₂ Transcripts
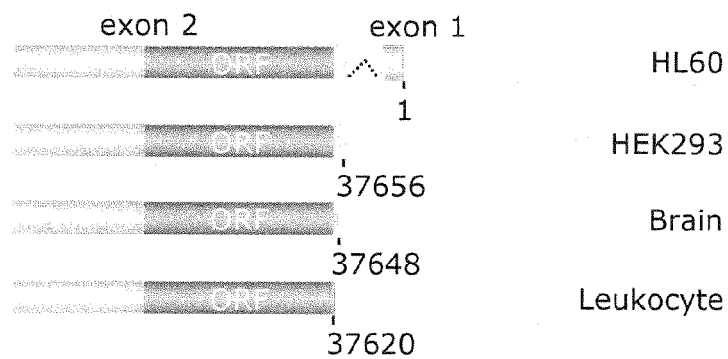
FIG. 2C

Mouse exon 1a RACE products

```
                              +1
Cnr2     CACCAGACCTCCTCTCATTCACTCATCTGCGAAAGTGTGAGAGCAAG
Spleen          AACGCAGAGTACGCGGGGATCTGCGAAAGTGTGAGAGCAAG
Spleen          AACGCAGAGTACGCGGTGATCTGCGAAAGTGTGAGAGCAAG
B cell          AACGCAGAGTACGCGGGGATCTGCGAAAGTGTGAGAGCAAG
B cell          AACGCAGAGTACGCGGTGATCTGCGAAAGTGTGAGAGCAAG
B cell          AAGGCAGAGTAGGGCGTCATCTGCGAAAGTGTGAGAGCAAG
B cell          AACGCAGAGTACGCGGGGATCTGCGAAAGTGTGAGAGCAAG
B cell                         ATCTGCGAAAGTGTGAGAGCAAG
```

Mouse exon 1b RACE products

```
                   +1          +1      +1
Cnr2     AGGCATGAGGCACACACATAGCCTGGCACATGTCACAGACAAAAGGATGT
Spleen            AACGCAGAGTACGACGGGACAGACAGAAGGATGT
B cell             ACGCAGAGTACGCGGCGGACAGACAAAAGGATGT
B cell              CGCAGAGTACGCGGGGACAGACAAAAGGATGT
B cell            ACGCAGAGTACGCGGGGACATGTCACAGACAAAAGGATGT
B cell         CAAGCAGGGGTATACATACCGTGTCACATGTCACAGACAAAAGGATGT
B cell                   TACATAGCCTGGCACATGTCACAGACAAAAGGATGT
B cell         ACAGCATGGGTATACATAGCGTGGCACAGGTCACAGACAAAAGGATGT
```

Mouse exon 2 RACE products

```
                                  +1
Cnr2     TATACATCAAACACATCCTTGCCCTAGAAATAGGTCTTCTAGAAGGCA
Spleen             AAGCAGAGTACGCGGGGAGAAATAGGTCTTCTAGAAGGCA
Spleen                      GGGGGAGAAATAGGTCTTCTAGAAGGCA
B cell             AAGCCGAGTTCGGCGGGAGAAATAGGTCTTCTAGAAGGCA
B cell             ACGCAGAGTACGGCGGGAGAAATAGGTCTTCTAGAAGGCA
B cell                      GGGGAGAAATAGGTCTTCTAGAAGGCA
```

Human RACE products

```
                              +1
CNR2     AGCAAGAGAAAGCTGGCTTGGGGTGGCACTCAACAGGTGCTCTGAGTG
B cell               TACGCGGGGGGCACTCAACAGGTGCTCTGAGTG
B cell                   CGGGGGGCACTCAACAGGTGCTCTGAGTG
B cell             ACGCAGAGTCGCGGGGGCACTCAACAGGTGCTCTGAGTG
```

FIG. 6

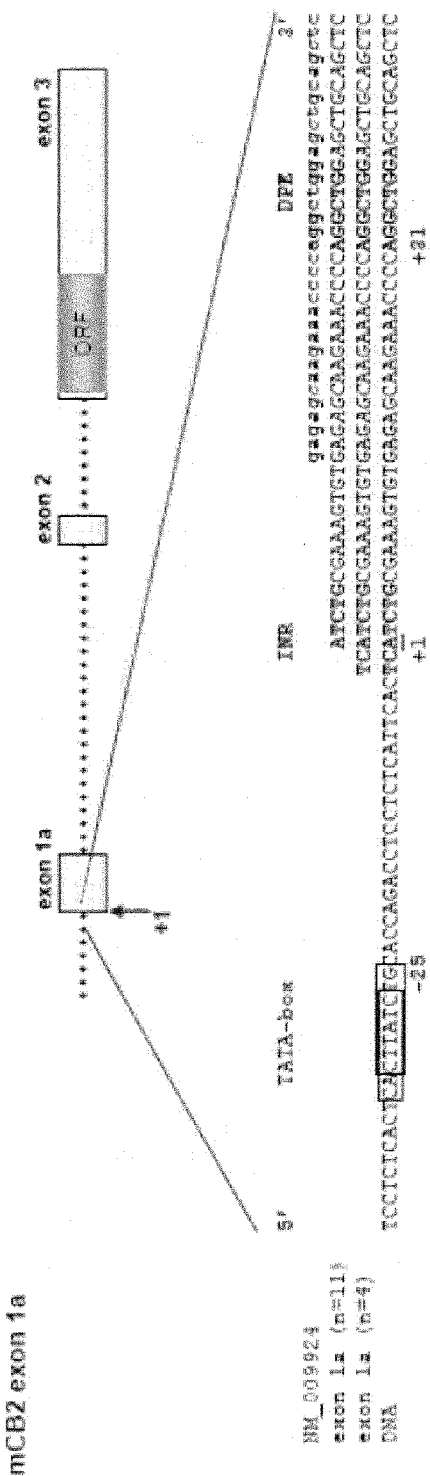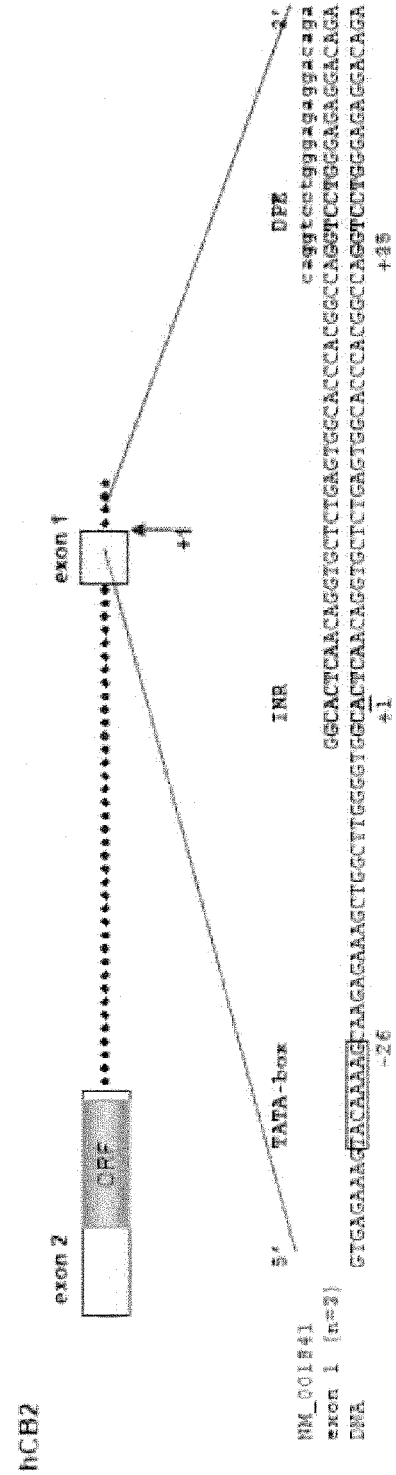
FIG. 7A
FIG. 7B

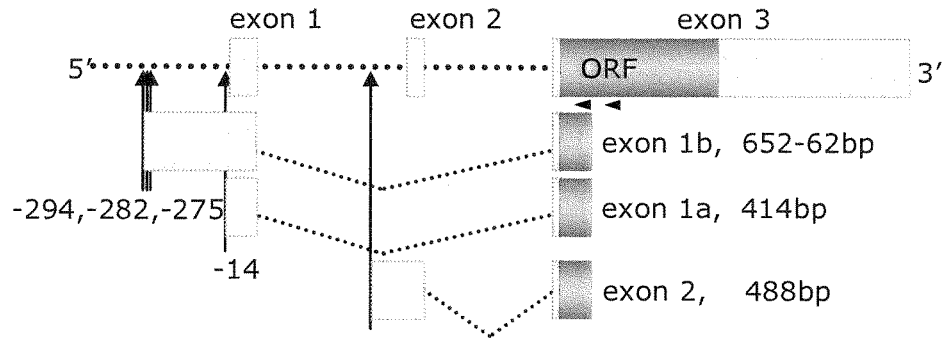

Exon 1a: 151 bp

-14
ATCTGCGAAAGTGTGAGAGCAAGAAACCCCAGGCTGGAGCTGCAGCTCTTGGGACCTACG
TGGGGGTCCCTGCTGGGTCTCCAGATCTGGATACAGAATAGCCAGGACAAGGCTCCACAA
GACCCTGGGGCCCAGCGGCTGACAAATGACA

Exon 1b: 412, 419, & 431 bp

-294       -282    -275
ACATAGCGTGGCACATGTCACAGACAAAAGGATGTAAACTTTACAGAGGTCAAGTGAGTT
GCAGGACAGCATACACCCGGGGCCAGATTAGAACCCAAGTTTCTGGAGTCTAAGGTCTAT
GCCTATGCCCTCCCCTGGCCAGAGTTCCTAGGAAGAGAGAATTCAACCGCAGGGCAAGAA
CACTGTGGCACTGAGGACCCAGAGGGGAAGTGGTAACCGGTACGGAAGGCCAGATCTCCT
CTCACTCACTTATCTGCACCAGACCTCCTCTCATTCACTCATTTGCGAAAGTGTGAGAGC
AAGAAACCCCAGGCTGGAGCTGCAGCTCTTGGGACCTACGTGGGGGTCCCTGCTGGGTCT
CCAGATCTGGATACAGAATAGCCAGGACAAGGCTCCACAAGACCCTGGGGCCCAGCGGCT
GACAAATGACA

Exon 2: 253 bp

-172
AGAAATAGGTCTTCTAGAAGGCACCCATGTGACTTGCAGAGGGTATCTCTATCTTCGTGG
AGACAGGGAGCCGGGCTTCCTGTTGCTGTGTGCATCCTGTTGTTCTCTTGTTAGGATGTC
CATCAAATGCATGCATTTCCTTTCCTAACTCTGGACAGTAACAGTCGTCTGCGGCCAAGC
TGTGCCTGAATGAGCAGAGGCACAGGCACCAGCCGTGGCCACCCAGCAAACATCTCTGCT
GACTCAGACTGGG

FIG. 9

Exon 1: 117 bp

GGGTGTGTTGTGGGTGGCTGGGCACTGGGAGCTGCCGGGGGGTGAGGAGTCCC
AGTTGTTTTTTGTCCTCTCCCAGGACCTGGCCGTGGGTGCCACTCAGAGCACC
TGTTGAGTGC<u>C</u>
     -35

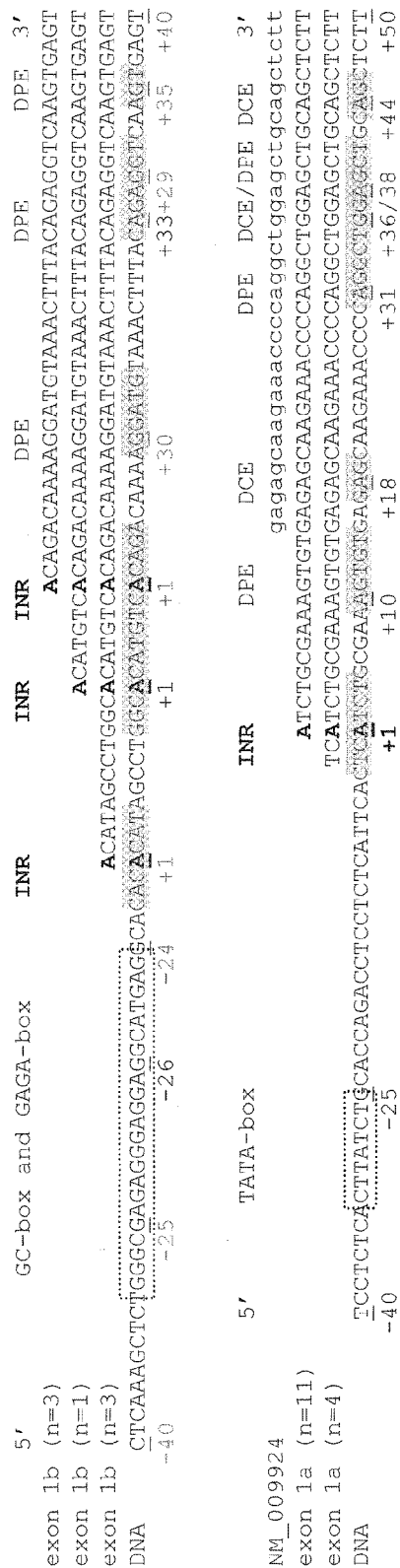
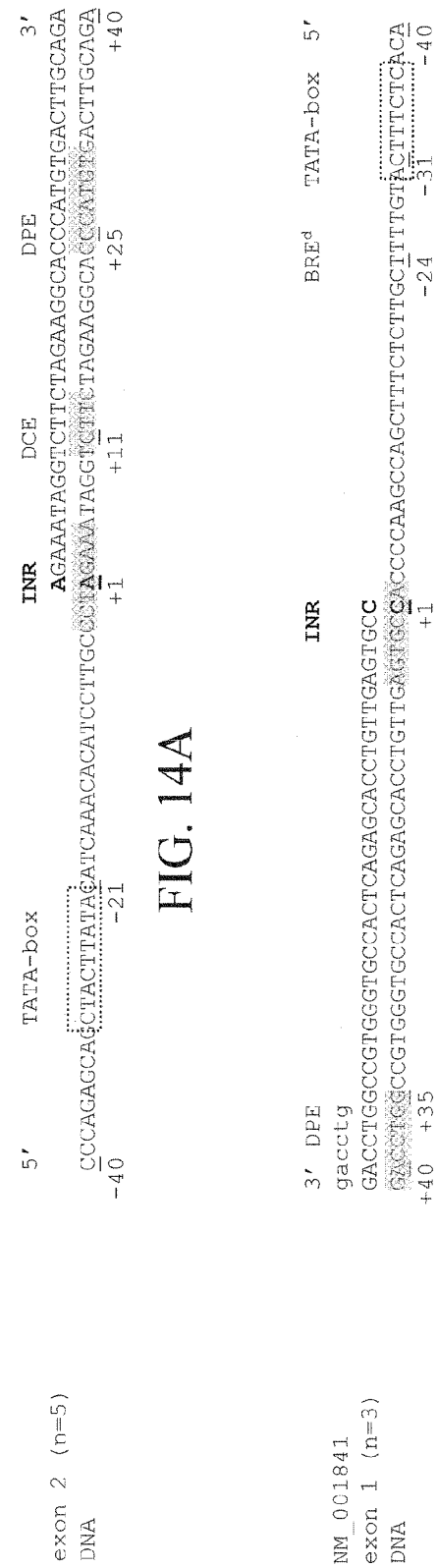
FIG. 14A
FIG. 14B

Exon 1 alignment

```
Mus_musculus  CAGGAGCCAGCAGCGTTCATTCATGTCATCTGCCAACACCTGCAGGCATTTGCATCTCAA
Homo_sapiens  CAGGATCCATCACC---CATTATGTTAATCTGCC------TGTAGGCATTTGCATTTCAA
                                                     +1
Mus_musculus  AGCTCTGGGCGAGAGG-GAGGAGGCATGAGGCACACACAT--------------------
Homo_sapiens  AGCTCTGGCCTAGTGGTGAAGAGGCATTGGAATGGCATGTCCTTTTAGGTGATCTACTGT
                             +1    +1   GATA                    STAT
Mus_musculus  -AGCCTGG---------CACATGTCACAGACAAAAGGATGTAAACTTTACAGAGGTCAAG
Homo_sapiens  AATGTTGGTGCATTATCCCCATTTTACAGATAAAGAAACTTGC-CTTTGGGGAAGTTAAG Mus_musculus  TGAGTTGCAGGACAGCATACACCCGGGGCCAGATTAGAACCCAAGTTTCTGGAGTCTAAG
Homo_sapiens  TGAAT--------CAACATTTTAACGAGGCTGTATTAGAACCCAAGTCCCTTGACTCCAGG
                                STAT6        GATA
Mus_musculus  GTCTATGCCTATGCCCTCCCCTGGCCAGAGTTCCTAGGAAGAGAGAATTCAACCGCAGGG
Homo_sapiens  GTCTAGGCCCATGCCCCACCCTGGCCAGAGTTCGTTGTAAGAGATAACTCAACCGCAGGG
                                                            Elk-1,  c-REL
Mus_musculus  -CAAGAACACTGTGGCACTGAGGACCCAGAGGGGAAGTGGTAACCGGTACGGAAGGCCAG
Homo_sapiens  GCAAGAGCATTGTGGCACCAGGGACCTGGAGGGGAAGTGGTAACAGGCACGGAAGGCCAG
                  GATA                                        +1
Mus_musculus  ATCTCCTCTCACTCACTTATCTGCACCAGACCTCCTCTCATTCACTCATCTGCGAAAGTG
Homo_sapiens  ACCTCCTCACACTCACTCATCTG---------------------TGAGAAAGTA
                                                              NF-kBp50
Mus_musculus  TGAGAGCAAGAAACCCCAGGCTGGAGCTGCAGCT----CTTGGGACCTACGTGGGGGTCCC
Homo_sapiens  CAAAAGCAAGAGAAAGCTGGCTTGGGGTGGCACTCAACAGGTGCTCTGAGTGGCACCCAC
                                                    +1
Mus_musculus  TGCTGGGTCTCCAGATCTGGATACAGAATAGCCAGGAC----AAGGCTCCACAAGACCCT
Homo_sapiens  GGCCAGGTCCTGGGAGA-GGACAGAAAACAACTGGGACTCCTCAGCCCCCGGCAGCTCCC Mus_musculus  GGGGCCCAGCGGCTGACAA-ATGACAGTGAGTGTAACTTCCTTTGTTGTTTTACTTCAGA
Homo_sapiens  AGTGCCCAGCCACCCACAACACAACCGTGA--GTAGCTTTTTTGTTG-TTTATTTTAGG
```

FIG. 15A

Exon 2 alignment

```
                                                     NF-kB,c-REL
Mus_musculus  .ATGGGGGGGGGGTATTGTTATTGTCTCTTCACAAGTGAGAAGAGGGACTTGCCCAAAGT
Homo_sapiens  ............................................................

Mus_musculus  CACATGATGAGAGTGACAGCATTGGACCCAGAGCAGCTACTTATACATCAAACACATCCT
Homo_sapiens  ............................................................
              STAT6 +1      STAT6                                STAT6
Mus_musculus  TGCCCTAGAAATAGGTCTTCTAGAAGGCACCCATGTGACTTGCAGAGGGTATCTCTATCT
Homo_sapiens  .............................................TGACTCCGAAAGGG-ATTTCTATCT
              STAT6           NF-kB,p65,c-REL
Mus_musculus  TC-----GTGGAGACAGGGAGCCGGGCTTCCTGTTGCTGTGTGCATCCTGTTGTTCTCTT
Homo_sapiens  GTCGAAAGGGAAGACAGGGAGCTGGGTTTCCTGTTGCTCTGTGCGTCCTGACGTTGGCTT Mus_musculus  GTTAGGATGTCCAT-CAAATGCATGCATTTCCTTTCCT----AACTCTGGACAGTAACAG
Homo_sapiens  GTTAAGACCTGCATCCAAATGCCCATATTTCCTGCCCTTACCTACTTTGGTTAATAACCA Mus_musculus  T---CGTCTGCGGCCAAGCTGTGCCTGAATGAGCAGAGGCACAGGCACCAGCCGTGGCCA
Homo_sapiens  CGCATGTTGGTGGCCATGCCGGGGCTAGGT-----GAGGCCCAAA-GCCAGCCACCGCCA Mus_musculus  CCCAGCAAACATCTCT--------GCTGACTCAGACTGGGGTAAGGCATTCCCTAACAGT
Homo_sapiens  CCC--CCAACATCCCTCTTCTAGGGTGGATTCTACATGGAGTAAGCCATATCTTGAC...
```

FIG. 15B

```
135450780, 5' T genome position
         FHDF              SWI/SNF            HOX-PBX              MEF2/YY1
TGTCACCTGCAAGCTGAAATAAACACACACACACACACACTTTTGATTTTCTGCTTTGTGATTTTTGAGGCAGGGTCTCTATTTGTAGCC
-604
   GREF/POZ/HSF1                                                    Sp1
CTGAATGTCCTAGAATTTGCTATGTAGACCAAGCTGGCCTTGAACTGCCTCTGCCTCCCGAGTGCTGGAACTAAAGGTGTGTGTCATCAT
                                                      -457
            PAX5/LEF-1(2 sites)                                          AP4/Myf5
GCCCAGCTTCTGAACTTGCTTTTGTCACAGTCACAGAATGGAGCAGAACCAGGAGCCAGCAGCGTTCATTCATGTCATCTGCCAACACCT
                   -388                              -359
           GAGAbox (ie GC-box)          INR      INR      INR      DPE
GCAGGCATTTGCATCTCAAAGCTCTGGGCGAGAGGGAGGAGGCATGAGGCACACACATAGCCTGGCACATGTCACAGACAAAAGGATGTA
                                                   -280    -270-268  -261
     DPE IRF1&2     TtK                                                      Oct-1
AACTTTACAGAGGTCAAGTGAGTTGCAGGACAGCATACACCCGGGGCCAGATTAGAACCCAAGTTTCTGGAGTCTAAGGTCTATGCCTAT
             -218                                            -172
         STAT6/POZ        c-Myb/LTUP                                      GABP/MZF1
GCCCTCCCCTGGCCAGAGTTCCTAGGAAGAGAGAATTCAACCGCAGGGCAAGAACACTGTGGCACTGAGGACCCAGAGGGGAAGTGGTAA
              -132                     -103                                      -72
   Elk-1                TATA-like/Sp1                            INR/RFX2   DCE
CCGGTACGGAAGGCCAGATCTCCTCTCACTCACTTATCTGCACCAGACCTCCTCTCATTCACTCATCTGCGAAAGTGTGAGAGCAAGAAA
                       -26                                  +1            +18
    DPE    DCE   DCE    DPE       BRE^d              INR/SRF            DCE   DPE
CCCCAGGCTGGAGCTGCAGCTCTTGGGACCTACGTGGGGGTCCCTGCTGGGTCTCCAGATCTGGATACAGAATAGCCAGGACAAGGCTCC
+27                              +69           +83
       AP4                                  DCE       BRE^d    DCE                  DCE
ACAAGACCCTGGGGCCCAGCGGCTGACAAATGACAgtgagtgtaacttcttttgttgtttacttcagactcctcgctccagaaagcct
                                +152                                             +205
                                                       3' T genome position, 135451588
```

FIG. 17

```
  +1 AUCUGCGAAAGUGUGAGAGCAAGAAACCCCAGGCUGGAGCUGCAGCUCUUGGGACCUACG
  61 UGGGGGUCCCUGCUGGGUCUCCAGAUCUGGAUACAGAAUAGCCAGGACAAGGCUCCACAA
 121 GACCCUGGGGCCCAGCGGCUGACAAAUGACA
```

FIG. 18

```
-261 ACAGACAAAAGGAUGUAAACUUUACAGAGGUCAAGUGAGUUGCAGGACAGCAUACACCCG
-201 GGGCCAGAUUAGAACCCAAGUUUCUGGAGUCUAAGGUCUAUGCCUAUGCCCUCCCCUGGC
-141 CAGAGUUCCUAGGAAGAGAGAAUUCAACCGCAGGGCAAGAACACUGUGGCACUGAGGACC
 -81 CAGGGGGAAGUGGUAACCGAGUACGGAAGGCCAGAUCUCCUCUCACUCACUUAUCUGCAC
 -21 CAGACCUCCUCUCAUUCACUCAUCUGCAAAGUGUGAGAGCAAGAAACCCCAGGCUGGAG
 +40 CUGCAGCUCUUGGGACCUACGUGGGGGUCCCUGCUGGGUCUCCAGAUCUGGAUACAGAAU
+100 AGCCAGGACAAGGCUCCACAAGACCCUGGGGCCCAGCGGCUGACAAAUGACA
```

FIG. 19

```
-268 ACAUGUCACAGACAAAAGGAUGUAAACUUUACAGAGGUCAAGUGAGUUGCAGGACAGCAU
-208 ACACCCGGGGCCAGAUUAGAACCCAAGUUUCUGGAGUCUAAGGUCUAUGCCUAUGCCCUC
-148 CCCUGGCCAGAGUUCCUAGGAAGAGAGAAUUCAACCGCAGGGCAAGAACACUGUGGCACU
 -88 GAGGACCCAGAGGGGAAGUGGUAACCGGUACGGAAGGCCAGAUCUCCUCUCACUCACUUA
 -28 UCUGCACCAGACCUCCUCUCAUUCACUCAUCUGCGAAAGUGUGAGAGCAAGAAACCCCAG
 +33 GCUGGAGCUGCAGCUCUUGGGACCUACGUGGGGGUCCCUGCUGGGUCUCCAGAUCUGGAU
 +93 ACAGAAUAGCCAGGACAAGGCUCCACAAGACCCUGGGGCCCAGCGGCUGACA
```

FIG. 20

```
-280 ACAUAGCGUGGCACAGGUCACAGACAAAAGGAUGUAAACUUUACAGAGGUCAAGUGAGUU
-220 GCAGGACAGCAUACACCCGGGGCCAGAUUAGAACCCAAGUUUCUGGAGUCUAAGGUCUAU
-160 GCCUAUGCCCUCCCCUGGCCAGAGUUCCUAGGAAGAGAGAAUUCAACCGCAGGGCAAGAA
-100 CACUGUGGCACUGAGGACCCAGAGGGGAAGUGGUAACCGGUACGGAAGGCCAGAUCUCCU
 -40 CUCACUCACUUAUCUGCACCAGACCUCCUCUCAUUCACUCAUUUGCGAAAGUGUGAGAGC
 +21 AAGAAACCCCAGGCUGGAGCUGCAGCUCUUGGGACCUACGUGGGGGUCCCUGCUGGGUCU
 +81 CCAGAUCUGGAUACAGAAUAGCCAGGACAAGGCUCCACAAGACCCUGGGGCCCAGCGGCU
+141 GACAAAUGACA
```

FIG. 21 muExon2

```
  1   AGAAATAGGT CTTCTAGAAG GCACCCATGT GACTTGCAGA GGGTATCTCT ATCTTCGTGG
 61   AGACAGGGAG CCGGGCTTCC TGTTGCTGTG TGCATCCTGT TGTTCTCTTG TTAGGATGTC
121   CATCAAATGC ATGCATTTCC TTTCCTAACT CTGGACAGTA ACAGTCGTCT GCGGCCAAGC
181   TGTGCCTGAA TGAGCAGAGG CACAGGCACC AGCCGTGGCC ACCCAGCAAA CATCTCTGCT
241   GACTCAGACT GGG
```

FIG. 31A

| siRNA | position | sequence |
|---|---|---|
| 1 | 133-151 | GCAUUUCCUUUCCUAACUC |
| 2 | 31-49 | GACUUGCAGAGGGUAUCUC |
| 3 | 218-236 | GCCACCCAGCAAACAUCUC |
| 4 | 102-120 | GUUCUCUUGUUAGGAUGUC |
| 5 | 29-47 | GUGACUUGCAGAGGGUAUC |
| 6 | 68-86 | GAGCCGGGCUUCCUGUUGC |
| 7 | 167-185 | GUCUGCGGCCAAGCUGUGC |
| 8 | 75-93 | GCUUCCUGUUGCUGUGUGC |
| 9 | 154-172 | GACAGUAACAGUCGUCUGC |
| 10 | 8-26 | GGUCUUCUAGAAGGCACCC |
| 11 | 192-210 | GAGCAGAGGCACAGGCACC |
| 12 | 158-176 | GUAACAGUCGUCUGCGGCC |
| 13 | 5-23 | AUAGGUCUUCUAGAAGGCA |
| 14 | 151-169 | UGGACAGUAACAGUCGUCU |
| 15 | 142-160 | UCCUAACUCUGGACAGUAA |
| 16 | 21-39 | CACCCAUGUGACUUGCAGA |
| 17 | 119-137 | CCAUCAAAUGCAUGCAUUU |
| 18 | 228-246 | AAACAUCUCUGCUGACUCA |
| 19 | 36-54 | GCAGAGGGUAUCUCUAUCU |
| 20 | 110-128 | GUUAGGAUGUCCAUCAAAU |
| 21 | 118-136 | GUCCAUCAAAUGCAUGCAU |
| 22 | 114-132 | GGAUGUCCAUCAAAUGCAU |
| 23 | 129-147 | GCAUGCAUUUCCUCCUAAC |
| 24 | 99-117 | GUUGUUCUCUUGUUAGGAU |
| 25 | 107-125 | UCUUGUUAGGAUUCCAUCA |
| 26 | 43-61 | GUAUCUCUAUCUUCGUGGA |
| 27 | 139-157 | CCUUUCCUAACUCUGGACA |
| 28 | 134-152 | CAUUUCCUUUCCUAACUCU |
| 29 | 136-154 | UGCAUUUCCUUUCCUAACU |
| 30 | 224-242 | CAGCAAACAUCUCUGCUGA |

FIG. 31B muExon1b

```
  1  ACATAGCGTG GCACATGTCA CAGACAAAAG GATGTAAACT TTACAGAGGT CAAGTGAGTT
 61  GCAGGACAGC ATACACCCGG GGCCAGATTA GAACCCAAGT TCTGGAGTC  TAAGGTCTAT
121  GCCTATGCCC TCCCCTGGCC AGAGTTCCTA GGAAGAGAGA ATTCAACCGC AGGGCAAGAA
181  CACTGTGGCA CTGAGGACCC AGAGGGGAAG TGGTAACCGG TACGGAAGGC CAGATCTCCT
241  CTCACTCACT TATCTGCACC AGACCTCCTC TCATTCACTC ATTTGCGAAA GTGTGAGAGC
301  AAGAAACCCC AGGCTGGAGC TGCAGCTCTT GGGACCTACG TGGGGGTCCC TGCTGGGTCT
361  CCAGATCTGG ATACAGAATA GCCAGGACAA GGCTCCACAA GACCCTGGGG CCCAGCGGCT
421  GACAAATGAC A
```

FIG. 32A

| siRNA | position | sequence |
|---|---|---|
| 1 | 364-382 | GAUCUGGAUACAGAAUAGC |
| 2 | 58-76 | GUUGCAGGACAGCAUACAC |
| 3 | 385-403 | GGACAAGGCUCCACAAGAC |
| 4 | 56-74 | GAGUUGCAGGACAGCAUAC |
| 5 | 220-238 | GUACGGAAGGCCAGAUCUC |
| 6 | 359-377 | CUCCAGAUCUGGAUACAGA |
| 7 | 291-309 | GUGUGAGAGCAAGAAACCC |
| 8 | 386-404 | GACAAGGCUCCACAAGACC |
| 9 | 99-117 | GUUUCUGGAGUCUAAGGUC |
| 10 | 229-247 | GCCAGAUCUCCUCUCACUC |
| 11 | 264-282 | CCUCCUCUCAUUCACUCAU |
| 12 | 105-123 | GGAGUCUAAGGUCUAUGCC |
| 13 | 205-223 | GGGAAGUGGUAACCGGUAC |
| 14 | 225-243 | GAAGGCCAGAUCUCCUCUC |
| 15 | 212-230 | GGUAACCGGUACGGAAGGC |
| 16 | 49-67 | GUCAAGUGAGUUGCAGGAC |
| 17 | 369-387 | GGAUACAGAAUAGCCAGGA |
| 18 | 152-170 | GAAGAGAGAAUUCAACCGC |
| 19 | 213-231 | GUAACCGGUACGGAAGGCC |
| 20 | 173-191 | GGCAAGAACACUGUGGCAC |
| 21 | 317-335 | GAGCUGCAGCUCUUGGGAC |
| 22 | 115-133 | GUCUAUCGGUAUGCCCUCC |
| 23 | 157-175 | GAGAAUUCAACCGCAGGGC |
| 24 | 114-132 | GGUCUAUGCCUAUGCCCUC |
| 25 | 81-100 | GGCCAGAUUAGAACCCAAG |
| 26 | 101-119 | UUCUGGAGUCUAAGGUCUA |
| 27 | 95-113 | CCAAGUUUCUGGAGUCUAA |
| 28 | 107-125 | AGUCUAAGGUCUAUGCCUA |
| 29 | 359-377 | CUCCAGAUCUGGAUACAGA |
| 30 | 135-153 | CUGGCCAGAGUUCCUAGGA |
| 31 | 139-161 | CCAGAGUCCUAGGAAGAGA |
| 32 | 173-191 | GGCAAGAACACUGUGGCAC |
| 33 | 257-275 | CACCAGACCUCCUCUCAUC |
| 34 | 20-38 | ACAGACAAAAGGAUGUAAA |
| 35 | 144-162 | GUUCCUAGGAAGAGAGAAU |
| 36 | 147-165 | CCUAGGAAGAGAGAAUUCA |
| 37 | 287-305 | GAAAGUGUGAGAGCAAGAA |
| 38 | 91-109 | GAACCCAAGUUUCUGGAGU |
| 39 | 272-290 | CAUUCACUCAUUUGCGAAA |
| 40 | 243-261 | CACUCACUUAUCUGCACCA |
| 41 | 270-288 | CUCAUUCACUCAUUUGCGA |
| 42 | 280-298 | CAUUUGCGAAAGUGUGAGA |
| 43 | 34-52 | GUAAACUUUACAGAGGUCA |

FIG. 32B hu-35REGION

Human CB2 gene sense sequence starting at position 1 in figure 14B

1  GGCACTCAAC AGGTGCTCTG AGTGGCACCC ACGGCCAGGT CCTGGGAGAG GACAGAAAAC
61 AACTGGGACT CCTCA

| siRNA | position | sequence |
|---|---|---|
| 1 | 12-30 | GGUGCUCUGAGUGGCACCC |
| 2 | 3-21 | CACUCAACAGGUGCUCUGA |

FIG. 33

SEQUENCE LISTING

```
<160> NUMBER OF SEQ ID NOS: 221

<210> SEQ ID NO 1
<211> LENGTH: 809
<212> TYPE: DNA
<213> ORGANISM: Mus musculus

<400> SEQUENCE: 1
tgtcacctgc aagctgaaat aaacacacac acacacacac ttttgattt  ctgctttgtg    60 atttttgagg cagggtctct atttgtagcc ctgaatgtcc tagaatttgc tatgtagacc   120
aagctggcct tgaactgcct ctgcctcccg agtgctggaa ctaaaggtgt gtgtcatcat   180
gcccagcttc tgaacttgct tttgtcacag tcacagaatg gagcagaacc aggagccagc   240
agcgttcatt catgtcatct gccaacacct gcaggcattt gcatctcaaa gctctgggcg   300
agagggagga ggcatgaggc acacacatag cctggcacat gtcacagaca aaaggatgta   360
aactttacag aggtcaagtg agttgcagga cagcatacac ccggggccag attagaaccc   420
aagtttctgg agtctaaggt ctatgcctat gccctcccct ggccagagtt cctaggaaga   480
gagaattcaa ccgcagggca agaacactgt ggcactgagg acccagaggg gaagtggtaa   540
ccggtacgga aggccagatc tcctctcact cacttatctg caccagacct cctctcattc   600
actcatctgc gaaagtgtga gagcaagaaa ccccaggctg gagctgcagc tcttgggacc   660
tacgtggggg tccctgctgg gtctccagat ctggatacag aatagccagg acaaggctcc   720
acaagaccct ggggcccagc ggctgacaaa tgacagtgag tgtaacttcc tttgttgttt   780
tacttcagac tcctcgctcc agaaagcct                                     809

<210> SEQ ID NO 2
<211> LENGTH: 151
<212> TYPE: RNA
<213> ORGANISM: Mus musculus

<400> SEQUENCE: 2
aucugcgaaa gugugagagc aagaaacccc aggcuggagc ugcagcucuu gggaccuacg    60
uggggguccc ugcuggggucu ccagaucugg auacagaaua gccaggacaa ggcuccacaa   120
gacccugggg cccagcggcu gacaaaugac a                                   151

<210> SEQ ID NO 3
<211> LENGTH: 412
<212> TYPE: RNA
<213> ORGANISM: Mus musculus

<400> SEQUENCE: 3
acagacaaaa ggauguaaac uuuacagagg ucaagugagu ugcaggacag cauacacccg    60
gggccagauu agaacccaag uuucuggagu cuaaggucua ugccuaugcc cuccccuggc   120
cagaguuccu aggaagagag aauucaaccg cagggcaaga acacugugc acugaggacc    180
```

```
caggggggaag ugguaaccga guacggaagg ccagaucucc ucucacucac uuaucugcac      240
cagaccuccu cucauucacu caucugcaaa agugugagag caagaaaccc caggcuggag      300
cugcagcucu ugggaccuac guggggqucc cugcugggquc uccagaucug gauacagaau    360
agccaggaca aggcuccaca agacccuggg gcccagcggc ugacaaauga ca             412

<210> SEQ ID NO 4
<211> LENGTH: 412
<212> TYPE: RNA
<213> ORGANISM: Mus musculus

<400> SEQUENCE: 4
acaugucaca gacaaaagga uguaaacuuu acagagguca agugaguugc aggacagcau      60
acacccgggg ccagauuaga acccaaguuu cuggagucua aggucuaugc cuaugcccuc    120
cccuggccag aguccuagg aagagagaau ucaaccgcag ggcaagaaca cuguggcacu     180
gaggacccag agggaagug guaaccggua cggaaggcca gaucccucu cacucacuua      240 ucugcaccag accuccucuc auucacucau cugcgaaagu gugagagcaa gaaacccccag   300 gcuggagcug cagcucuugg gaccuacgug ggguccccug cugggqucucc agaucuggau   360 acagaauagc caggacaagg cuccacaaga cccuggggcc cagcggcuga ca            412

<210> SEQ ID NO 5
<211> LENGTH: 431
<212> TYPE: RNA
<213> ORGANISM: Mus musculus

<400> SEQUENCE: 5
acauagcgug gcacagguca cagacaaaag gauguaaacu uuacagaggu caagugaguu      60
gcaggacagc auacacccgg ggccagauua gaacccaagu uucuggaguc uaaggucuau    120
gccuaugccc uccccuggcc agaguuccua ggaagagaga auucaaccgc agggcaagaa    180
cacuguggca cugaggaccc agaggggaag ugguaaccgg uacggaaggc cagaucuccu    240
cucacucacu uaucugcacc agaccuccuc ucauucacuc auuugcgaaa gugugagagc    300
aagaaacccc caggcuggagc ugcagcucuu gggaccuacg ugggguccc ugcugggquc    360 ccagaucugg auacagaaua gccaggacaa ggcuccacaa gacccugggg cccagcggcu   420
gacaaaugac a                                                         431

<210> SEQ ID NO 6
<211> LENGTH: 75
<212> TYPE: DNA
<213> ORGANISM: Homo sapiens

<400> SEQUENCE: 6
ggcactcaac aggtgctctg agtggcaccc acggccaggt cctgggagag acagaaaac       60 aactgggact cctca                                                      75

<210> SEQ ID NO 7
<211> LENGTH: 19
<212> TYPE: RNA
<213> ORGANISM: Artificial Sequence
<220> FEATURE:
<223> OTHER INFORMATION: siRNA 1

<400> SEQUENCE: 7
ggugcucuga guggcaccc                                                  19
```

```
<210> SEQ ID NO 8
<211> LENGTH: 19
<212> TYPE: RNA
<213> ORGANISM: Artificial Sequence
<220> FEATURE:
<223> OTHER INFORMATION: siRNA 2

<400> SEQUENCE: 8
cacucaacag gugcucuga                                                  19

<210> SEQ ID NO 9
<211> LENGTH: 253
<212> TYPE: DNA
<213> ORGANISM: Mus musculus

<400> SEQUENCE: 9
agaaataggt cttctagaag gcacccatgt gacttgcaga gggtatctct atcttcgtgg      60
agacagggag ccgggcttcc tgttgctgtg tgcatcctgt tgttctcttg ttaggatgtc     120
catcaaatgc atgcatttcc tttcctaact ctggacagta acagtcgtct gcggccaagc    180
tgtgcctgaa tgagcagagg cacaggcacc agccgtggcc acccagcaaa catctctgct    240
gactcagact ggg                                                       253

<210> SEQ ID NO 10
<211> LENGTH: 19
<212> TYPE: RNA
<213> ORGANISM: Artificial Sequence
<220> FEATURE:
<223> OTHER INFORMATION: siRNA 1

<400> SEQUENCE: 10 gcauuccuu uccuaacuc                                                   19

<210> SEQ ID NO 11
<211> LENGTH: 19
<212> TYPE: RNA
<213> ORGANISM: Artificial Sequence
<220> FEATURE:
<223> OTHER INFORMATION: siRNA 2

<400> SEQUENCE: 11
gacuugcaga ggguaucuc                                                  19

<210> SEQ ID NO 12
<211> LENGTH: 19
<212> TYPE: RNA
<213> ORGANISM: Artificial Sequence
<220> FEATURE:
<223> OTHER INFORMATION: siRNA 3

<400> SEQUENCE: 12
gccacccagc aaacaucuc                                                  19

<210> SEQ ID NO 13
<211> LENGTH: 19
<212> TYPE: RNA
<213> ORGANISM: Artificial Sequence
<220> FEATURE:
<223> OTHER INFORMATION: siRNA 4

<400> SEQUENCE: 13
guucucuugu uaggauguc                                                  19
```

```
<210> SEQ ID NO 14
<211> LENGTH: 19
<212> TYPE: RNA
<213> ORGANISM: Artificial Sequence
<220> FEATURE:
<223> OTHER INFORMATION: siRNA 5

<400> SEQUENCE: 14
gugacuugca gaggguauc                                                19

<210> SEQ ID NO 15
<211> LENGTH: 19
<212> TYPE: RNA
<213> ORGANISM: Artificial Sequence
<220> FEATURE:
<223> OTHER INFORMATION: siRNA 6

<400> SEQUENCE: 15
gagccgggcu uccuguugc                                                19

<210> SEQ ID NO 16
<211> LENGTH: 19
<212> TYPE: RNA
<213> ORGANISM: Artificial Sequence
<220> FEATURE:
<223> OTHER INFORMATION: siRNA 7

<400> SEQUENCE: 16
gucugcggcc aagcugugc                                                19

<210> SEQ ID NO 17
<211> LENGTH: 19
<212> TYPE: RNA
<213> ORGANISM: Artificial Sequence
<220> FEATURE:
<223> OTHER INFORMATION: siRNA 8

<400> SEQUENCE: 17
gcuuccuguu gcugugugc                                                19

<210> SEQ ID NO 18
<211> LENGTH: 19
<212> TYPE: RNA
<213> ORGANISM: Artificial Sequence
<220> FEATURE:
<223> OTHER INFORMATION: siRNA 9

<400> SEQUENCE: 18
gacaguaaca gucgucugc                                                19

<210> SEQ ID NO 19
<211> LENGTH: 19
<212> TYPE: RNA
<213> ORGANISM: Artificial Sequence
<220> FEATURE:
<223> OTHER INFORMATION: siRNA 10

<400> SEQUENCE: 19
ggucuucuag aaggcaccc                                                19

<210> SEQ ID NO 20
<211> LENGTH: 19
<212> TYPE: RNA
<213> ORGANISM: Artificial Sequence
<220> FEATURE:
<223> OTHER INFORMATION: siRNA 11
```

```
<400> SEQUENCE: 20
gagcagaggc acaggcacc                                                    19

<210> SEQ ID NO 21
<211> LENGTH: 19
<212> TYPE: RNA
<213> ORGANISM: Artificial Sequence
<220> FEATURE:
<223> OTHER INFORMATION: siRNA 12

<400> SEQUENCE: 21
guaacagucg ucugcggcc                                                    19

<210> SEQ ID NO 22
<211> LENGTH: 19
<212> TYPE: RNA
<213> ORGANISM: Artificial Sequence
<220> FEATURE:
<223> OTHER INFORMATION: siRNA 13

<400> SEQUENCE: 22
auaggucuuc uagaaggca                                                    19

<210> SEQ ID NO 23
<211> LENGTH: 19
<212> TYPE: RNA
<213> ORGANISM: Artificial Sequence
<220> FEATURE:
<223> OTHER INFORMATION: siRNA 14

<400> SEQUENCE: 23
uggacaguaa cagucgucu                                                    19

<210> SEQ ID NO 24
<211> LENGTH: 19
<212> TYPE: RNA
<213> ORGANISM: Artificial Sequence
<220> FEATURE:
<223> OTHER INFORMATION: siRNA 15

<400> SEQUENCE: 24
uccuaacucu ggacaguaa                                                    19

<210> SEQ ID NO 25
<211> LENGTH: 19
<212> TYPE: RNA
<213> ORGANISM: Artificial Sequence
<220> FEATURE:
<223> OTHER INFORMATION: siRNA 16

<400> SEQUENCE: 25
cacccaugug acuugcaga                                                    19

<210> SEQ ID NO 26
<211> LENGTH: 19
<212> TYPE: RNA
<213> ORGANISM: Artificial Sequence
<220> FEATURE:
<223> OTHER INFORMATION: siRNA 17

<400> SEQUENCE: 26
ccaucaaaug caugcauuu                                                    19
```

```
<210> SEQ ID NO 27
<211> LENGTH: 19
<212> TYPE: RNA
<213> ORGANISM: Artificial Sequence
<220> FEATURE:
<223> OTHER INFORMATION: siRNA 18

<400> SEQUENCE: 27
aaacaucucu gcugacuca                                              19

<210> SEQ ID NO 28
<211> LENGTH: 19
<212> TYPE: RNA
<213> ORGANISM: Artificial Sequence
<220> FEATURE:
<223> OTHER INFORMATION: siRNA 19

<400> SEQUENCE: 28
gcagagggua ucucuaucu                                              19

<210> SEQ ID NO 29
<211> LENGTH: 19
<212> TYPE: RNA
<213> ORGANISM: Artificial Sequence
<220> FEATURE:
<223> OTHER INFORMATION: siRNA 20

<400> SEQUENCE: 29
guuaggaugu ccaucaaau                                              19

<210> SEQ ID NO 30
<211> LENGTH: 19
<212> TYPE: RNA
<213> ORGANISM: Artificial Sequence
<220> FEATURE:
<223> OTHER INFORMATION: siRNA 21

<400> SEQUENCE: 30
guccaucaaa ugcaugcau                                              19

<210> SEQ ID NO 31
<211> LENGTH: 19
<212> TYPE: RNA
<213> ORGANISM: Artificial Sequence
<220> FEATURE:
<223> OTHER INFORMATION: siRNA 22

<400> SEQUENCE: 31
ggauguccau caaaugcau                                              19

<210> SEQ ID NO 32
<211> LENGTH: 19
<212> TYPE: RNA
<213> ORGANISM: Artificial Sequence
<220> FEATURE:
<223> OTHER INFORMATION: siRNA 23

<400> SEQUENCE: 32
gcaugcauuu ccuccuaac                                              19

<210> SEQ ID NO 33
<211> LENGTH: 19
<212> TYPE: RNA
<213> ORGANISM: Artificial Sequence
<220> FEATURE:
<223> OTHER INFORMATION: siRNA 24
```

```
<400> SEQUENCE: 33
guuguucucu uguuaggau                                                    19

<210> SEQ ID NO 34
<211> LENGTH: 19
<212> TYPE: RNA
<213> ORGANISM: Artificial Sequence
<220> FEATURE:
<223> OTHER INFORMATION: siRNA 25

<400> SEQUENCE: 34
ucuuguuagg auuccauca                                                    19

<210> SEQ ID NO 35
<211> LENGTH: 19
<212> TYPE: RNA
<213> ORGANISM: Artificial Sequence
<220> FEATURE:
<223> OTHER INFORMATION: siRNA 26

<400> SEQUENCE: 35
guaucucuau cuucgugga                                                    19

<210> SEQ ID NO 36
<211> LENGTH: 19
<212> TYPE: RNA
<213> ORGANISM: Artificial Sequence
<220> FEATURE:
<223> OTHER INFORMATION: siRNA 27

<400> SEQUENCE: 36 ccuuccuaa cucuggaca                                                     19

<210> SEQ ID NO 37
<211> LENGTH: 19
<212> TYPE: RNA
<213> ORGANISM: Artificial Sequence
<220> FEATURE:
<223> OTHER INFORMATION: siRNA 28

<400> SEQUENCE: 37 cauuccuuu ccuaacucu                                                     19

<210> SEQ ID NO 38
<211> LENGTH: 19
<212> TYPE: RNA
<213> ORGANISM: Artificial Sequence
<220> FEATURE:
<223> OTHER INFORMATION: siRNA 29

<400> SEQUENCE: 38
ugcauuuccu uuccuaacu                                                    19

<210> SEQ ID NO 39
<211> LENGTH: 19
<212> TYPE: RNA
<213> ORGANISM: Artificial Sequence
<220> FEATURE:
<223> OTHER INFORMATION: siRNA 30

<400> SEQUENCE: 39
cagcaaacau cucugcuga                                                    19
```

```
<210> SEQ ID NO 40
<211> LENGTH: 431
<212> TYPE: DNA
<213> ORGANISM: Mus musculus

<400> SEQUENCE: 40
acatagcgtg gcacatgtca cagacaaaag gatgtaaact ttacagaggt caagtgagtt        60
gcaggacagc atacccgg ggccagatta gaacccaagt ttctggagtc taaggtctat         120
gcctatgccc tccctggcc agagttccta ggaagagaga attcaaccgc agggcaagaa        180
cactgtggca ctgaggaccc agagggaag tggtaaccgg tacgaaggc cagatctcct         240 ctcactcact tatctgcacc agacctcctc tcattcactc atttgcgaaa gtgtgagagc       300
aagaaacccc aggctggagc tgcagctctt gggacctacg tgggggtccc tgctgggtct       360
ccagatctgg atacagaata gccaggacaa ggctccacaa gaccctgggg cccagcggct       420
gacaaatgac a                                                            431

<210> SEQ ID NO 41
<211> LENGTH: 19
<212> TYPE: RNA
<213> ORGANISM: Artificial Sequence
<220> FEATURE:
<223> OTHER INFORMATION: siRNA 1

<400> SEQUENCE: 41
gaucuggaua cagaauagc                                                    19

<210> SEQ ID NO 42
<211> LENGTH: 19
<212> TYPE: RNA
<213> ORGANISM: Artificial Sequence
<220> FEATURE:
<223> OTHER INFORMATION: siRNA 2

<400> SEQUENCE: 42
guugcaggac agcauacac                                                    19

<210> SEQ ID NO 43
<211> LENGTH: 19
<212> TYPE: RNA
<213> ORGANISM: Artificial Sequence
<220> FEATURE:
<223> OTHER INFORMATION: siRNA 3

<400> SEQUENCE: 43
ggacaaggcu ccacaagac                                                    19

<210> SEQ ID NO 44
<211> LENGTH: 19
<212> TYPE: RNA
<213> ORGANISM: Artificial Sequence
<220> FEATURE:
<223> OTHER INFORMATION: siRNA 4

<400> SEQUENCE: 44
gaguugcagg acagcauac                                                    19

<210> SEQ ID NO 45
<211> LENGTH: 19
<212> TYPE: RNA
<213> ORGANISM: Artificial Sequence
<220> FEATURE:
<223> OTHER INFORMATION: siRNA 5
```

-continued

```
<400> SEQUENCE: 45
guacggaagg ccagaucuc                                                19

<210> SEQ ID NO 46
<211> LENGTH: 19
<212> TYPE: RNA
<213> ORGANISM: Artificial Sequence
<220> FEATURE:
<223> OTHER INFORMATION: siRNA 46

<400> SEQUENCE: 46
cuccagaucu ggauacaga                                                19

<210> SEQ ID NO 47
<211> LENGTH: 19
<212> TYPE: RNA
<213> ORGANISM: Artificial Sequence
<220> FEATURE:
<223> OTHER INFORMATION: siRNA 7

<400> SEQUENCE: 47
gugugagagc aagaaaccc                                                19

<210> SEQ ID NO 48
<211> LENGTH: 19
<212> TYPE: RNA
<213> ORGANISM: Artificial Sequence
<220> FEATURE:
<223> OTHER INFORMATION: siRNA 8

<400> SEQUENCE: 48
gacaaggcuc cacaagacc                                                19

<210> SEQ ID NO 49
<211> LENGTH: 19
<212> TYPE: RNA
<213> ORGANISM: Artificial Sequence
<220> FEATURE:
<223> OTHER INFORMATION: siRNA 9

<400> SEQUENCE: 49
guuucuggag ucuaagguc                                                19

<210> SEQ ID NO 50
<211> LENGTH: 19
<212> TYPE: RNA
<213> ORGANISM: Artificial Sequence
<220> FEATURE:
<223> OTHER INFORMATION: siRNA 10

<400> SEQUENCE: 50
gccagaucuc cucucacuc                                                19

<210> SEQ ID NO 51
<211> LENGTH: 19
<212> TYPE: RNA
<213> ORGANISM: Artificial Sequence
<220> FEATURE:
<223> OTHER INFORMATION: siRNA 11

<400> SEQUENCE: 51
ccuccucuca uucacucau                                                19
```

```
<210> SEQ ID NO 52
<211> LENGTH: 19
<212> TYPE: RNA
<213> ORGANISM: Artificial Sequence
<220> FEATURE:
<223> OTHER INFORMATION: siRNA 12

<400> SEQUENCE: 52
ggagucuaag gucuaugcc                                               19

<210> SEQ ID NO 53
<211> LENGTH: 19
<212> TYPE: RNA
<213> ORGANISM: Artificial Sequence
<220> FEATURE:
<223> OTHER INFORMATION: siRNA 13

<400> SEQUENCE: 53
gggaaguggu aaccgguac                                               19

<210> SEQ ID NO 54
<211> LENGTH: 19
<212> TYPE: RNA
<213> ORGANISM: Artificial Sequence
<220> FEATURE:
<223> OTHER INFORMATION: siRNA 14

<400> SEQUENCE: 54
gaaggccaga ucuccucuc                                               19

<210> SEQ ID NO 55
<211> LENGTH: 19
<212> TYPE: RNA
<213> ORGANISM: Artificial Sequence
<220> FEATURE:
<223> OTHER INFORMATION: siRNA 15

<400> SEQUENCE: 55
gguaaccggu acggaaggc                                               19

<210> SEQ ID NO 56
<211> LENGTH: 19
<212> TYPE: RNA
<213> ORGANISM: Artificial Sequence
<220> FEATURE:
<223> OTHER INFORMATION: siRNA 16

<400> SEQUENCE: 56
gucaagugag uugcaggac                                               19

<210> SEQ ID NO 57
<211> LENGTH: 19
<212> TYPE: RNA
<213> ORGANISM: Artificial Sequence
<220> FEATURE:
<223> OTHER INFORMATION: siRNA 17

<400> SEQUENCE: 57
ggauacagaa uagccagga                                               19

<210> SEQ ID NO 58
<211> LENGTH: 19
<212> TYPE: RNA
<213> ORGANISM: Artificial Sequence
<220> FEATURE:
<223> OTHER INFORMATION: siRNA 18
```

```
<400> SEQUENCE: 58
gaagagagaa uucaaccgc                                              19

<210> SEQ ID NO 59
<211> LENGTH: 19
<212> TYPE: RNA
<213> ORGANISM: Artificial Sequence
<220> FEATURE:
<223> OTHER INFORMATION: siRNA 19

<400> SEQUENCE: 59
guaaccggua cggaaggcc                                              19

<210> SEQ ID NO 60
<211> LENGTH: 19
<212> TYPE: RNA
<213> ORGANISM: Artificial Sequence
<220> FEATURE:
<223> OTHER INFORMATION: siRNA 20

<400> SEQUENCE: 60
ggcaagaaca cuguggcac                                              19

<210> SEQ ID NO 61
<211> LENGTH: 19
<212> TYPE: RNA
<213> ORGANISM: Artificial Sequence
<220> FEATURE:
<223> OTHER INFORMATION: siRNA 21

<400> SEQUENCE: 61
gagcugcagc ucuugggac                                              19

<210> SEQ ID NO 62
<211> LENGTH: 19
<212> TYPE: RNA
<213> ORGANISM: Artificial Sequence
<220> FEATURE:
<223> OTHER INFORMATION: siRNA 22

<400> SEQUENCE: 62
gucuaucggu augcccucc                                              19

<210> SEQ ID NO 63
<211> LENGTH: 19
<212> TYPE: RNA
<213> ORGANISM: Artificial Sequence
<220> FEATURE:
<223> OTHER INFORMATION: siRNA 23

<400> SEQUENCE: 63
gagaauucaa ccgcagggc                                              19

<210> SEQ ID NO 64
<211> LENGTH: 19
<212> TYPE: RNA
<213> ORGANISM: Artificial Sequence
<220> FEATURE:
<223> OTHER INFORMATION: siRNA 24

<400> SEQUENCE: 64
ggucuaugcc uaugcccuc                                              19
```

```
<210> SEQ ID NO 65
<211> LENGTH: 19
<212> TYPE: RNA
<213> ORGANISM: Artificial Sequence
<220> FEATURE:
<223> OTHER INFORMATION: siRNA 25

<400> SEQUENCE: 65
ggccagauua gaacccaag                                                    19

<210> SEQ ID NO 66
<211> LENGTH: 19
<212> TYPE: RNA
<213> ORGANISM: Artificial Sequence
<220> FEATURE:
<223> OTHER INFORMATION: siRNA 26

<400> SEQUENCE: 66
uucuggaguc uaaggucua                                                    19

<210> SEQ ID NO 67
<211> LENGTH: 19
<212> TYPE: RNA
<213> ORGANISM: Artificial Sequence
<220> FEATURE:
<223> OTHER INFORMATION: siRNA 27

<400> SEQUENCE: 67
ccaaguuucu ggagucuaa                                                    19

<210> SEQ ID NO 68
<211> LENGTH: 19
<212> TYPE: RNA
<213> ORGANISM: Artificial Sequence
<220> FEATURE:
<223> OTHER INFORMATION: siRNA 28

<400> SEQUENCE: 68
agucuaaggu cuaugccua                                                    19

<210> SEQ ID NO 69
<211> LENGTH: 19
<212> TYPE: RNA
<213> ORGANISM: Artificial Sequence
<220> FEATURE:
<223> OTHER INFORMATION: siRNA 29

<400> SEQUENCE: 69
cuccagaucu ggauacaga                                                    19

<210> SEQ ID NO 70
<211> LENGTH: 19
<212> TYPE: RNA
<213> ORGANISM: Artificial Sequence
<220> FEATURE:
<223> OTHER INFORMATION: siRNA 30

<400> SEQUENCE: 70
cuggccagag uuccuagga                                                    19

<210> SEQ ID NO 71
<211> LENGTH: 19
<212> TYPE: RNA
<213> ORGANISM: Artificial Sequence
<220> FEATURE:
<223> OTHER INFORMATION: siRNA 31
```

```
<400> SEQUENCE: 71
ccagaguccu aggaagaga                                              19

<210> SEQ ID NO 72
<211> LENGTH: 19
<212> TYPE: RNA
<213> ORGANISM: Artificial Sequence
<220> FEATURE:
<223> OTHER INFORMATION: siRNA 32

<400> SEQUENCE: 72
ggcaagaaca cuguggcac                                              19

<210> SEQ ID NO 73
<211> LENGTH: 19
<212> TYPE: RNA
<213> ORGANISM: Artificial Sequence
<220> FEATURE:
<223> OTHER INFORMATION: siRNA 33

<400> SEQUENCE: 73
caccagaccu ccucucauc                                              19

<210> SEQ ID NO 74
<211> LENGTH: 19
<212> TYPE: RNA
<213> ORGANISM: Artificial Sequence
<220> FEATURE:
<223> OTHER INFORMATION: siRNA 34

<400> SEQUENCE: 74
acagacaaaa ggauguaaa                                              19

<210> SEQ ID NO 75
<211> LENGTH: 19
<212> TYPE: RNA
<213> ORGANISM: Artificial Sequence
<220> FEATURE:
<223> OTHER INFORMATION: siRNA 35

<400> SEQUENCE: 75
guuccuagga agagagaau                                              19

<210> SEQ ID NO 76
<211> LENGTH: 19
<212> TYPE: RNA
<213> ORGANISM: Artificial Sequence
<220> FEATURE:
<223> OTHER INFORMATION: siRNA 36

<400> SEQUENCE: 76
ccuaggaaga gagaauuca                                              19

<210> SEQ ID NO 77
<211> LENGTH: 19
<212> TYPE: RNA
<213> ORGANISM: Artificial Sequence
<220> FEATURE:
<223> OTHER INFORMATION: siRNA 37

<400> SEQUENCE: 77
gaaaguguga gagcaagaa                                              19
```

```
<210> SEQ ID NO 78
<211> LENGTH: 19
<212> TYPE: RNA
<213> ORGANISM: Artificial Sequence
<220> FEATURE:
<223> OTHER INFORMATION: siRNA 38

<400> SEQUENCE: 78
gaacccaagu uucuggagu                                                19

<210> SEQ ID NO 79
<211> LENGTH: 19
<212> TYPE: RNA
<213> ORGANISM: Artificial Sequence
<220> FEATURE:
<223> OTHER INFORMATION: siRNA 39

<400> SEQUENCE: 79
cauucacuca uuugcgaaa                                                19

<210> SEQ ID NO 80
<211> LENGTH: 19
<212> TYPE: RNA
<213> ORGANISM: Artificial Sequence
<220> FEATURE:
<223> OTHER INFORMATION: siRNA 40

<400> SEQUENCE: 80
cacucacuua ucugcacca                                                19

<210> SEQ ID NO 81
<211> LENGTH: 19
<212> TYPE: RNA
<213> ORGANISM: Artificial Sequence
<220> FEATURE:
<223> OTHER INFORMATION: siRNA 41

<400> SEQUENCE: 81
cucauucacu cauuugcga                                                19

<210> SEQ ID NO 82
<211> LENGTH: 19
<212> TYPE: RNA
<213> ORGANISM: Artificial Sequence
<220> FEATURE:
<223> OTHER INFORMATION: siRNA 42

<400> SEQUENCE: 82
cauuugcgaa agugugaga                                                19

<210> SEQ ID NO 83
<211> LENGTH: 19
<212> TYPE: RNA
<213> ORGANISM: Artificial Sequence
<220> FEATURE:
<223> OTHER INFORMATION: siRNA 43

<400> SEQUENCE: 83
guaaacuuua cagagguca                                                19

<210> SEQ ID NO 84
<211> LENGTH: 47
<212> TYPE: DNA
<213> ORGANISM: Mus musculus

<400> SEQUENCE: 84
caccagacct cctctcattc actcatctgc gaaagtgtga gagcaag                 47
```

```
<210> SEQ ID NO 85
<211> LENGTH: 41
<212> TYPE: DNA
<213> ORGANISM: Mus musculus

<400> SEQUENCE: 85
aacgcagagt acgcggggat ctgcgaaagt gtgagagcaa g           41

<210> SEQ ID NO 86
<211> LENGTH: 41
<212> TYPE: DNA
<213> ORGANISM: Mus musculus

<400> SEQUENCE: 86
aacgcagagt acgcggtgat ctgcgaaagt gtgagagcaa g           41

<210> SEQ ID NO 87
<211> LENGTH: 41
<212> TYPE: DNA
<213> ORGANISM: Mus musculus

<400> SEQUENCE: 87
aacgcagagt acgcggggat ctgcgaaagt gtgagagcaa g           41

<210> SEQ ID NO 88
<211> LENGTH: 41
<212> TYPE: DNA
<213> ORGANISM: Mus musculus

<400> SEQUENCE: 88
aacgcagagt acgcggtgat ctgcgaaagt gtgagagcaa g           41

<210> SEQ ID NO 89
<211> LENGTH: 41
<212> TYPE: DNA
<213> ORGANISM: Mus musculus

<400> SEQUENCE: 89
aaggcagagt aggggtcat ctgcgaaagt gtgagagcaa g            41

<210> SEQ ID NO 90
<211> LENGTH: 41
<212> TYPE: DNA
<213> ORGANISM: Mus musculus

<400> SEQUENCE: 90
aacgcagagt acgcggggat ctgcgaaagt gtgagagcaa g           41

<210> SEQ ID NO 91
<211> LENGTH: 23
<212> TYPE: DNA
<213> ORGANISM: Mus musculus

<400> SEQUENCE: 91
atctgcgaaa gtgtgagagc aag                              23

<210> SEQ ID NO 92
<211> LENGTH: 50
<212> TYPE: DNA
<213> ORGANISM: Mus musculus

<400> SEQUENCE: 92
aggcatgagg cacacacata gcctggcaca tgtcacagac aaaaggatgt   50
```

```
<210> SEQ ID NO 93
<211> LENGTH: 34
<212> TYPE: DNA
<213> ORGANISM: Mus musculus

<400> SEQUENCE: 93
aacgcagagt acgacgggac agacagaagg atgt                           34

<210> SEQ ID NO 94
<211> LENGTH: 33
<212> TYPE: DNA
<213> ORGANISM: Mus musculus

<400> SEQUENCE: 94
acgcagagta cgcggggaca gacaaaagga tgt                            33

<210> SEQ ID NO 95
<211> LENGTH: 32
<212> TYPE: DNA
<213> ORGANISM: Mus musculus

<400> SEQUENCE: 95
cgcagagtac gcggggacag acaaaaggat gt                             32

<210> SEQ ID NO 96
<211> LENGTH: 40
<212> TYPE: DNA
<213> ORGANISM: Mus musculus

<400> SEQUENCE: 96
acgcagagta cgcggggaca tgtcacagac aaaaggatgt                     40

<210> SEQ ID NO 97
<211> LENGTH: 48
<212> TYPE: DNA
<213> ORGANISM: Mus musculus

<400> SEQUENCE: 97
caagcagggg tatacatacc gtgtcacatg tcacagacaa aaggatgt            48

<210> SEQ ID NO 98
<211> LENGTH: 36
<212> TYPE: DNA
<213> ORGANISM: Mus musculus

<400> SEQUENCE: 98
tacatagcct ggcacatgtc acagacaaaa ggatgt                         36

<210> SEQ ID NO 99
<211> LENGTH: 48
<212> TYPE: DNA
<213> ORGANISM: Mus musculus

<400> SEQUENCE: 99
acagcatggg tatacatagc gtggcacagg tcacagacaa aaggatgt            48

<210> SEQ ID NO 100
<211> LENGTH: 48
<212> TYPE: DNA
<213> ORGANISM: Mus musculus

<400> SEQUENCE: 100
tatacatcaa acacatcctt gccctagaaa taggtcttct agaaggca            48
```

```
<210> SEQ ID NO 101
<211> LENGTH: 40
<212> TYPE: DNA
<213> ORGANISM: Mus musculus

<400> SEQUENCE: 101
aagcagagta cgcggggaga ataggtctt ctagaaggca                               40

<210> SEQ ID NO 102
<211> LENGTH: 28
<212> TYPE: DNA
<213> ORGANISM: Mus musculus

<400> SEQUENCE: 102
gggggagaaa taggtcttct agaaggca                                           28

<210> SEQ ID NO 103
<211> LENGTH: 40
<212> TYPE: DNA
<213> ORGANISM: Mus musculus

<400> SEQUENCE: 103
aagccgagtt cggcgggaga ataggtctt ctagaaggca                               40

<210> SEQ ID NO 104
<211> LENGTH: 40
<212> TYPE: DNA
<213> ORGANISM: Mus musculus

<400> SEQUENCE: 104
acgcagagta cggcgggaga ataggtctt ctagaaggca                               40

<210> SEQ ID NO 105
<211> LENGTH: 27
<212> TYPE: DNA
<213> ORGANISM: Mus musculus

<400> SEQUENCE: 105
ggggagaaat aggtcttcta gaaggca                                            27

<210> SEQ ID NO 106
<211> LENGTH: 48
<212> TYPE: DNA
<213> ORGANISM: Homo sapiens

<400> SEQUENCE: 106
agcaagagaa agctggcttg gggtggcact caacaggtgc tctgagtg                     48

<210> SEQ ID NO 107
<211> LENGTH: 33
<212> TYPE: DNA
<213> ORGANISM: Homo sapiens

<400> SEQUENCE: 107
tacgcggggg gcactcaaca ggtgctctga gtg                                     33

<210> SEQ ID NO 108
<211> LENGTH: 29
<212> TYPE: DNA
<213> ORGANISM: Homo sapiens

<400> SEQUENCE: 108 cgggggcac tcaacaggtg ctctgagtg                                           29
```

<210> SEQ ID NO 109
<211> LENGTH: 39
<212> TYPE: DNA
<213> ORGANISM: Homo sapiens

<400> SEQUENCE: 109
acgcagagtc gcgggggcac tcaacaggtg ctctgagtg            39

<210> SEQ ID NO 110
<211> LENGTH: 10
<212> TYPE: DNA
<213> ORGANISM: Artificial Sequence
<220> FEATURE:
<223> OTHER INFORMATION: UPM sequence supplied with RACE kit

<400> SEQUENCE: 110
aacgcagagt            10

<210> SEQ ID NO 111
<211> LENGTH: 34
<212> TYPE: DNA
<213> ORGANISM: Mus musculus

<400> SEQUENCE: 111
gagagcaaga aacccaggc tggagctgca gctc            34

<210> SEQ ID NO 112
<211> LENGTH: 48
<212> TYPE: DNA
<213> ORGANISM: Mus musculus

<400> SEQUENCE: 112
atctgcgaaa gtgtgagagc aagaaacccc aggctggagc tgcagctc            48

<210> SEQ ID NO 113
<211> LENGTH: 50
<212> TYPE: DNA
<213> ORGANISM: Mus musculus

<400> SEQUENCE: 113
tcatctgcga aagtgtgaga gcaagaaacc ccaggctgga gctgcagctc            50

<210> SEQ ID NO 114
<211> LENGTH: 92
<212> TYPE: DNA
<213> ORGANISM: Mus musculus

<400> SEQUENCE: 114
tcctctcact cacttatctg caccagacct cctctcattc actcatctgc gaaagtgtga            60
gagcaagaaa ccccaggctg gagctgcagc tc            92

<210> SEQ ID NO 115
<211> LENGTH: 21
<212> TYPE: DNA
<213> ORGANISM: Homo sapiens

<400> SEQUENCE: 115
caggtcctgg gagaggacag a            21

<210> SEQ ID NO 116
<211> LENGTH: 56
<212> TYPE: DNA
<213> ORGANISM: Homo sapiens

```
<400> SEQUENCE: 116
ggcactcaac aggtgctctg agtggcaccc acggccaggt cctgggagag gacaga        56

<210> SEQ ID NO 117
<211> LENGTH: 95
<212> TYPE: DNA
<213> ORGANISM: Homo sapiens

<400> SEQUENCE: 117
gtgagaaagt acaaaagcaa gagaaagctg gcttggggtg gcactcaaca ggtgctctga   60
gtggcaccca cggccaggtc ctgggagagg acaga                              95

<210> SEQ ID NO 118
<211> LENGTH: 151
<212> TYPE: DNA
<213> ORGANISM: Mus musculus

<400> SEQUENCE: 118
atctgcgaaa gtgtgagagc aagaaacccc aggctggagc tgcagctctt gggacctacg   60
tgggggtccc tgctgggtct ccagatctgg atacagaata gccaggacaa ggctccacaa  120
gaccctgggg cccagcggct gacaaatgac a                                  151

<210> SEQ ID NO 119
<211> LENGTH: 431
<212> TYPE: DNA
<213> ORGANISM: Mus musculus

<400> SEQUENCE: 119
acatagcgtg gcacatgtca cagacaaaag gatgtaaact ttacagaggt caagtgagtt   60
gcaggacagc atacacccgg ggccagatta gaacccaagt ttctggagtc taaggtctat  120
gcctatgccc tcccctggcc agagttccta ggaagagaga attcaaccgc agggcaagaa  180
cactgtggca ctgaggaccc agaggggaag tggtaaccgg tacggaaggc cagatctcct  240
ctcactcact tatctgcacc agacctcctc tcattcactc atttgcgaaa gtgtgagagc  300
aagaaacccc aggctggagc tgcagctctt gggacctacg tgggggtccc tgctgggtct  360
ccagatctgg atacagaata gccaggacaa ggctccacaa gaccctgggg cccagcggct  420
gacaaatgac a                                                        431

<210> SEQ ID NO 120
<211> LENGTH: 253
<212> TYPE: DNA
<213> ORGANISM: Mus musculus

<400> SEQUENCE: 120
agaaataggt cttctagaag gcacccatgt gacttgcaga gggtatctct atcttcgtgg   60
agacagggag ccgggcttcc tgttgctgtg tgcatcctgt tgttctcttg ttaggatgtc  120
catcaaatgc atgcatttcc tttcctaact ctggacagta acagtcgtct gcggccaagc  180
tgtgcctgaa tgagcagagg cacaggcacc agccgtggcc acccagcaaa catctctgct  240
gactcagact ggg                                                      253

<210> SEQ ID NO 121
<211> LENGTH: 117
<212> TYPE: DNA
<213> ORGANISM: Homo sapiens
```

-continued

<400> SEQUENCE: 121
gggtgtgttg tgggtggctg ggcactggga gctgccgggg ggtgaggagt cccagttgtt    60
ttttgtcctc tcccaggacc tggccgtggg tgccactcag agcacctgtt gagtgcc     117

<210> SEQ ID NO 122
<211> LENGTH: 12
<212> TYPE: DNA
<213> ORGANISM: Mus musculus

<400> SEQUENCE: 122
aggcacacac at                                                       12

<210> SEQ ID NO 123
<211> LENGTH: 24
<212> TYPE: DNA
<213> ORGANISM: Mus musculus

<400> SEQUENCE: 123
ccttgcccta gaataggtc ttct                                           24

<210> SEQ ID NO 124
<211> LENGTH: 17
<212> TYPE: DNA
<213> ORGANISM: Homo sapiens

<400> SEQUENCE: 124
tgagtgccac cccaagc                                                  17

<210> SEQ ID NO 125
<211> LENGTH: 40
<212> TYPE: DNA
<213> ORGANISM: Mus musculus

<400> SEQUENCE: 125
acagacaaaa ggatgtaaac tttacagagg tcaagtgagt                         40

<210> SEQ ID NO 126
<211> LENGTH: 47
<212> TYPE: DNA
<213> ORGANISM: Mus musculus

<400> SEQUENCE: 126
acatgtcaca gacaaaagga tgtaaacttt acagaggtca agtgagt                 47

<210> SEQ ID NO 127
<211> LENGTH: 59
<212> TYPE: DNA
<213> ORGANISM: Mus musculus

<400> SEQUENCE: 127
acatagcctg gcacatgtca cagacaaaag gatgtaaact ttacagaggt caagtgagt    59

<210> SEQ ID NO 128
<211> LENGTH: 99
<212> TYPE: DNA
<213> ORGANISM: Mus musculus

<400> SEQUENCE: 128
ctcaaagctc tgggcgagag ggaggaggca tgaggcacac acatagcctg gcacatgtca   60
cagacaaaag gatgtaaact ttacagaggt caagtgagt                          99

```
<210> SEQ ID NO 129
<211> LENGTH: 36
<212> TYPE: DNA
<213> ORGANISM: Mus musculus

<400> SEQUENCE: 129
gagagcaaga aaccccaggc tggagctgca gctctt                              36

<210> SEQ ID NO 130
<211> LENGTH: 50
<212> TYPE: DNA
<213> ORGANISM: Mus musculus

<400> SEQUENCE: 130
atctgcgaaa gtgtgagagc aagaaacccc aggctggagc tgcagctctt              50

<210> SEQ ID NO 131
<211> LENGTH: 52
<212> TYPE: DNA
<213> ORGANISM: Mus musculus

<400> SEQUENCE: 131
tcatctgcga aagtgtgaga gcaagaaacc ccaggctgga gctgcagctc tt            52

<210> SEQ ID NO 132
<211> LENGTH: 90
<212> TYPE: DNA
<213> ORGANISM: Mus musculus

<400> SEQUENCE: 132
tcctctcact tatctgcacc agacctcctc tcattcactc atctgcgaaa gtgtgagagc    60
aagaaacccc aggctggagc tgcagctctt                                     90

<210> SEQ ID NO 133
<211> LENGTH: 40
<212> TYPE: DNA
<213> ORGANISM: Mus musculus

<400> SEQUENCE: 133
agaaataggt cttctagaag gcacccatgt gacttgcaga                          40

<210> SEQ ID NO 134
<211> LENGTH: 80
<212> TYPE: DNA
<213> ORGANISM: Mus musculus

<400> SEQUENCE: 134
cccagagcag ctacttatac atcaaacaca tccttgccct agaaataggt cttctagaag    60
gcacccatgt gacttgcaga                                                80

<210> SEQ ID NO 135
<211> LENGTH: 41
<212> TYPE: DNA
<213> ORGANISM: Homo sapiens

<400> SEQUENCE: 135
gacctggccg tgggtgccac tcagagcacc tgttgagtgc c                        41

<210> SEQ ID NO 136
<211> LENGTH: 81
<212> TYPE: DNA
<213> ORGANISM: Homo sapiens
```

```
<400> SEQUENCE: 136
gacctggccg tgggtgccac tcagagcacc tgttgagtgc caccccaagc cagctttctc      60
ttgcttttgt actttctcac a                                                81

<210> SEQ ID NO 137
<211> LENGTH: 76
<212> TYPE: DNA
<213> ORGANISM: Mus musculus

<400> SEQUENCE: 137
caggagccag cagcgttcat tcatgtcatc tgccaacacc tgcaggcatt tgcatctcaa      60
agctctgggc gagagg                                                      76

<210> SEQ ID NO 138
<211> LENGTH: 23
<212> TYPE: DNA
<213> ORGANISM: Mus musculus

<400> SEQUENCE: 138
gaggaggcat gaggcacaca cat                                              23

<210> SEQ ID NO 139
<211> LENGTH: 163
<212> TYPE: DNA
<213> ORGANISM: Mus musculus

<400> SEQUENCE: 139
cacatgtcac agacaaaagg atgtaaactt tacagaggtc aagtgagttg caggacagca      60
tacacccggg gccagattag aacccaagtt tctggagtct aaggtctatg cctatgccct     120
cccctggcca gagttcctag gaagagagaa ttcaaccgca ggg                       163

<210> SEQ ID NO 140
<211> LENGTH: 153
<212> TYPE: DNA
<213> ORGANISM: Mus musculus

<400> SEQUENCE: 140
caagaacact gtggcactga ggacccagag gggaagtggt aaccggtacg gaaggccaga      60
tctcctctca ctcacttatc tgcaccagac ctcctctcat tcactcatct gcgaaagtgt     120
gagagcaaga aaccccaggc tggagctgca gct                                  153

<210> SEQ ID NO 141
<211> LENGTH: 61
<212> TYPE: DNA
<213> ORGANISM: Mus musculus

<400> SEQUENCE: 141
cttgggacct acgtgggggt ccctgctggg tctccagatc tggatacaga atagccagga      60
c                                                                      61

<210> SEQ ID NO 142
<211> LENGTH: 37
<212> TYPE: DNA
<213> ORGANISM: Mus musculus

<400> SEQUENCE: 142
aaggctccac aagaccctgg ggcccagcgg ctgacaa                               37
```

<210> SEQ ID NO 143
<211> LENGTH: 40
<212> TYPE: DNA
<213> ORGANISM: Mus musculus

<400> SEQUENCE: 143
atgacagtga gtgtaacttc ctttgttgtt ttacttcaga                              40

<210> SEQ ID NO 144
<211> LENGTH: 14
<212> TYPE: DNA
<213> ORGANISM: Homo sapiens

<400> SEQUENCE: 144
caggatccat cacc                                                          14

<210> SEQ ID NO 145
<211> LENGTH: 17
<212> TYPE: DNA
<213> ORGANISM: Homo sapiens

<400> SEQUENCE: 145
cattatgtta atctgcc                                                       17

<210> SEQ ID NO 146
<211> LENGTH: 123
<212> TYPE: DNA
<213> ORGANISM: Homo sapiens

<400> SEQUENCE: 146
tgtaggcatt tgcatttcaa agctctggcc tagtggtgaa gaggcattgg aatggcatgt        60
ccttttaggt gatctactgt aatgttggtg cattatcccc attttacaga taaagaaact       120
tgc                                                                    123

<210> SEQ ID NO 147
<211> LENGTH: 21
<212> TYPE: DNA
<213> ORGANISM: Homo sapiens

<400> SEQUENCE: 147
ctttggggaa gttaagtgaa t                                                  21

<210> SEQ ID NO 148
<211> LENGTH: 191
<212> TYPE: DNA
<213> ORGANISM: Homo sapiens

<400> SEQUENCE: 148
caacatttta acgaggctgt attagaaccc aagtcccttg actccagggt ctaggcccat        60
gccccaccct ggccagagtt cgttgtaaga gataactcaa ccgcaggggc aagagcattg       120
tggcaccagg gacctggagg ggaagtggta acaggcacgg aaggccagac ctcctcacac       180
tcactcatct g                                                           191

<210> SEQ ID NO 149
<211> LENGTH: 87
<212> TYPE: DNA
<213> ORGANISM: Homo sapiens

<400> SEQUENCE: 149
tgagaaagta caaaagcaag agaaagctgg cttggggtgg cactcaacag gtgctctgag        60
tggcacccac ggccaggtcc tgggaga                                            87

```
<210> SEQ ID NO 150
<211> LENGTH: 72
<212> TYPE: DNA
<213> ORGANISM: Homo sapiens

<400> SEQUENCE: 150
ggacagaaaa caactgggac tcctcagccc ccggcagctc ccagtgccca gccacccaca    60
acacaaccgt ga                                                        72

<210> SEQ ID NO 151
<211> LENGTH: 16
<212> TYPE: DNA
<213> ORGANISM: Homo sapiens

<400> SEQUENCE: 151
gtagcttttt ttgttg                                                    16

<210> SEQ ID NO 152
<211> LENGTH: 11
<212> TYPE: DNA
<213> ORGANISM: Homo sapiens

<400> SEQUENCE: 152
tttattttag g                                                         11

<210> SEQ ID NO 153
<211> LENGTH: 181
<212> TYPE: DNA
<213> ORGANISM: Mus musculus

<400> SEQUENCE: 153 atggggggg ggtattgtta ttgtctcttc acaagtgaga agagggactt gcccaaagtc     60
acatgatgag agtgacagca ttggacccag agcagctact tatacatcaa acacatcctt   120
gccctagaaa taggtcttct agaaggcacc catgtgactt gcagagggta tctctatctt   180
c                                                                   181

<210> SEQ ID NO 154
<211> LENGTH: 67
<212> TYPE: DNA
<213> ORGANISM: Mus musculus

<400> SEQUENCE: 154
gtggagacag ggagccgggc ttcctgttgc tgtgtgcatc ctgttgttct cttgttagga    60
tgtccat                                                              67

<210> SEQ ID NO 155
<211> LENGTH: 23
<212> TYPE: DNA
<213> ORGANISM: Mus musculus

<400> SEQUENCE: 155
caaatgcatg catttccttt cct                                            23

<210> SEQ ID NO 156
<211> LENGTH: 19
<212> TYPE: DNA
<213> ORGANISM: Mus musculus

<400> SEQUENCE: 156
aactctggac agtaacagt                                                 19
```

```
<210> SEQ ID NO 157
<211> LENGTH: 72
<212> TYPE: DNA
<213> ORGANISM: Mus musculus

<400> SEQUENCE: 157
cgtctgcggc caagctgtgc ctgaatgagc agaggcacag gcaccagccg tggccaccca      60
gcaaacatct ct                                                         72

<210> SEQ ID NO 158
<211> LENGTH: 36
<212> TYPE: DNA
<213> ORGANISM: Mus musculus

<400> SEQUENCE: 158
gctgactcag actggggtaa ggcattccct aacagt                               36

<210> SEQ ID NO 159
<211> LENGTH: 14
<212> TYPE: DNA
<213> ORGANISM: Homo sapiens

<400> SEQUENCE: 159
tgactccgaa aggg                                                       14

<210> SEQ ID NO 160
<211> LENGTH: 160
<212> TYPE: DNA
<213> ORGANISM: Homo sapiens

<400> SEQUENCE: 160
atttctatct gtcgaaaggg aagacaggga gctgggtttc ctgttgctct gtgcgtcctg      60
acgttggctt gttaagacct gcatccaaat gcccatattt cctgcccctta cctactttgg   120 ttaataacca cgcatgttgg tggccatgcc ggggctaggt                          160

<210> SEQ ID NO 161
<211> LENGTH: 10
<212> TYPE: DNA
<213> ORGANISM: Homo sapiens

<400> SEQUENCE: 161
gaggcccaaa                                                            10

<210> SEQ ID NO 162
<211> LENGTH: 17
<212> TYPE: DNA
<213> ORGANISM: Homo sapiens

<400> SEQUENCE: 162
gccagccacc gccaccc                                                    17

<210> SEQ ID NO 163
<211> LENGTH: 52
<212> TYPE: DNA
<213> ORGANISM: Homo sapiens

<400> SEQUENCE: 163
ccaacatccc tcttctaggg tggattctac atggagtaag ccatatcttg ac             52

<210> SEQ ID NO 164
<211> LENGTH: 54
<212> TYPE: DNA
<213> ORGANISM: Mus musculus
```

```
<400> SEQUENCE: 164
acagacaaaa ggatgtaaac tttacagagg tcaagtgagt tgcaggacag cata            54

<210> SEQ ID NO 165
<211> LENGTH: 61
<212> TYPE: DNA
<213> ORGANISM: Mus musculus

<400> SEQUENCE: 165
acatgtcaca gacaaaagga tgtaaacttt acagaggtca agtgagttgc aggacagcat      60
a                                                                     61

<210> SEQ ID NO 166
<211> LENGTH: 73
<212> TYPE: DNA
<213> ORGANISM: Mus musculus

<400> SEQUENCE: 166
acatagcctg gcacatgtca cagacaaaag gatgtaaact ttacagaggt caagtgagtt      60
gcaggacagc ata                                                        73

<210> SEQ ID NO 167
<211> LENGTH: 113
<212> TYPE: DNA
<213> ORGANISM: Mus musculus

<400> SEQUENCE: 167
ctcaaagctc tgggcgagag ggaggaggca tgaggcacac acatagcctg gcacatgtca      60
cagacaaaag gatgtaaact ttacagaggt caagtgagtt gcaggacagc ata            113

<210> SEQ ID NO 168
<211> LENGTH: 59
<212> TYPE: DNA
<213> ORGANISM: Mus musculus

<400> SEQUENCE: 168
gagagcaaga aaccccaggc tggagctgca gctcttggga cctacgtggg ggtccctgc       59

<210> SEQ ID NO 169
<211> LENGTH: 73
<212> TYPE: DNA
<213> ORGANISM: Mus musculus

<400> SEQUENCE: 169
atctgcgaaa gtgtgagagc aagaaacccc aggctggagc tgcagctctt gggacctacg      60 tggggtccc tgc                                                         73

<210> SEQ ID NO 170
<211> LENGTH: 75
<212> TYPE: DNA
<213> ORGANISM: Mus musculus

<400> SEQUENCE: 170
tcatctgcga aagtgtgaga gcaagaaacc ccaggctgga gctgcagctc ttggaccta       60 cgtgggggtc cctgc                                                      75

<210> SEQ ID NO 171
<211> LENGTH: 109
<212> TYPE: DNA
<213> ORGANISM: Mus musculus
```

-continued

<400> SEQUENCE: 171
ctcacttatc tgcaccagac ctcctctcat tcactcatct gcgaaagtgt gagagcaaga    60
aaccccaggc tggagctgca gctcttggga cctacgtggg ggtccctgc              109

<210> SEQ ID NO 172
<211> LENGTH: 40
<212> TYPE: DNA
<213> ORGANISM: Mus musculus

<400> SEQUENCE: 172
agaaataggt cttctagaag gcacccatgt gacttgcaga                         40

<210> SEQ ID NO 173
<211> LENGTH: 80
<212> TYPE: DNA
<213> ORGANISM: Mus musculus

<400> SEQUENCE: 173
cccagagcag ctacttatac atcaaacaca tccttgccct agaaataggt cttctagaag    60
gcacccatgt gacttgcaga                                               80

<210> SEQ ID NO 174
<211> LENGTH: 41
<212> TYPE: DNA
<213> ORGANISM: Homo sapiens

<400> SEQUENCE: 174
gacctggccg tgggtgccac tcagagcacc tgttgagtgc c                       41

<210> SEQ ID NO 175
<211> LENGTH: 81
<212> TYPE: DNA
<213> ORGANISM: Homo sapiens

<400> SEQUENCE: 175
gacctggccg tgggtgccac tcagagcacc tgttgagtgc caccccaagc cagctttctc    60
ttgcttttgt actttctcac a                                             81

<210> SEQ ID NO 176
<211> LENGTH: 30
<212> TYPE: DNA
<213> ORGANISM: Artificial Sequence
<220> FEATURE:
<223> OTHER INFORMATION: Mouse GSP1; mCB2-R301

<400> SEQUENCE: 176
cgaccccgtg gaagacgtgg aagatgacaa                                    30

<210> SEQ ID NO 177
<211> LENGTH: 22
<212> TYPE: DNA
<213> ORGANISM: Artificial Sequence
<220> FEATURE:
<223> OTHER INFORMATION: Mouse GSP2; mCB2-R217

<400> SEQUENCE: 177
tgaacaggta cgagggcttt ct                                            22

<210> SEQ ID NO 178
<211> LENGTH: 31
<212> TYPE: DNA
<213> ORGANISM: Artificial Sequence

```
<220> FEATURE:
<223> OTHER INFORMATION: Human GSP1; hCB2-R298

<400> SEQUENCE: 178
gccaggaagt cagccccagc caagctgcca a                                31

<210> SEQ ID NO 179
<211> LENGTH: 30
<212> TYPE: DNA
<213> ORGANISM: Artificial Sequence
<220> FEATURE:
<223> OTHER INFORMATION: Human GSP2; hCB2-R163

<400> SEQUENCE: 179
gcacagccac gttctccagg gcacttagca                                  30

<210> SEQ ID NO 180
<211> LENGTH: 17
<212> TYPE: DNA
<213> ORGANISM: Artificial Sequence
<220> FEATURE:
<223> OTHER INFORMATION: mE1b A (DNA forward primer)

<400> SEQUENCE: 180
ggaggaggca tgaggca                                                17

<210> SEQ ID NO 181
<211> LENGTH: 17
<212> TYPE: DNA
<213> ORGANISM: Artificial Sequence
<220> FEATURE:
<223> OTHER INFORMATION: mE1b B (forward primer)

<400> SEQUENCE: 181
acacatagcc tggcaca                                                17

<210> SEQ ID NO 182
<211> LENGTH: 19
<212> TYPE: DNA
<213> ORGANISM: Artificial Sequence
<220> FEATURE:
<223> OTHER INFORMATION: mE1b C (reverse primer)

<400> SEQUENCE: 182
gcggttgaat tctctcttc                                              19

<210> SEQ ID NO 183
<211> LENGTH: 24
<212> TYPE: DNA
<213> ORGANISM: Artificial Sequence
<220> FEATURE:
<223> OTHER INFORMATION: mE1b G (reverse primer)

<400> SEQUENCE: 183
gacaaagttg caggcgaaga tcac                                        24

<210> SEQ ID NO 184
<211> LENGTH: 20
<212> TYPE: DNA
<213> ORGANISM: Artificial Sequence
<220> FEATURE:
<223> OTHER INFORMATION: mE2 D (DNA forward primer)

<400> SEQUENCE: 184
atacatcaaa cacatccttg                                             20
```

```
<210> SEQ ID NO 185
<211> LENGTH: 19
<212> TYPE: DNA
<213> ORGANISM: Artificial Sequence
<220> FEATURE:
<223> OTHER INFORMATION: mE2 E (forward primer)

<400> SEQUENCE: 185
ttctagaagg cacccatgt                                              19

<210> SEQ ID NO 186
<211> LENGTH: 20
<212> TYPE: DNA
<213> ORGANISM: Artificial Sequence
<220> FEATURE:
<223> OTHER INFORMATION: mE2 F (reverse primer)

<400> SEQUENCE: 186
cctctgctca ttcaggtaca                                             20

<210> SEQ ID NO 187
<211> LENGTH: 24
<212> TYPE: DNA
<213> ORGANISM: Artificial Sequence
<220> FEATURE:
<223> OTHER INFORMATION: mE2 G (reverse primer)

<400> SEQUENCE: 187
gacaaagttg caggcgaaga tcac                                        24

<210> SEQ ID NO 188
<211> LENGTH: 18
<212> TYPE: DNA
<213> ORGANISM: Artificial Sequence
<220> FEATURE:
<223> OTHER INFORMATION: hE1 J (DNA forward primer)

<400> SEQUENCE: 188
gcaagagaaa gctggctt                                               18

<210> SEQ ID NO 189
<211> LENGTH: 19
<212> TYPE: DNA
<213> ORGANISM: Artificial Sequence
<220> FEATURE:
<223> OTHER INFORMATION: hE1 I (forward primer)

<400> SEQUENCE: 189
tcaacaggtg ctctgagtg                                              19

<210> SEQ ID NO 190
<211> LENGTH: 19
<212> TYPE: DNA
<213> ORGANISM: Artificial Sequence
<220> FEATURE:
<223> OTHER INFORMATION: hE1 H (reverse primer)

<400> SEQUENCE: 190
ctgaggagtc ccagttgtt                                              19

<210> SEQ ID NO 191
<211> LENGTH: 26
<212> TYPE: DNA
<213> ORGANISM: Artificial Sequence
<220> FEATURE:
<223> OTHER INFORMATION: mCB2-E3 F (forward primer)
```

<400> SEQUENCE: 191
gccgtgctct atattatcct gtcctc　　　　　　　　　　　　　　　　　　26

<210> SEQ ID NO 192
<211> LENGTH: 24
<212> TYPE: DNA
<213> ORGANISM: Artificial Sequence
<220> FEATURE:
<223> OTHER INFORMATION: mCB2-E3 R (reverse primer)

<400> SEQUENCE: 192
gacaaagttg caggcgaaga tcac　　　　　　　　　　　　　　　　　　24

<210> SEQ ID NO 193
<211> LENGTH: 28
<212> TYPE: DNA
<213> ORGANISM: Artificial Sequence
<220> FEATURE:
<223> OTHER INFORMATION: mCB2-E3 P

<400> SEQUENCE: 193
agaaagccct cgtacctgtt catcagca　　　　　　　　　　　　　　　28

<210> SEQ ID NO 194
<211> LENGTH: 18
<212> TYPE: DNA
<213> ORGANISM: Artificial Sequence
<220> FEATURE:
<223> OTHER INFORMATION: mCB2-E1a F (forward primer)

<400> SEQUENCE: 194
tcatctgcga aagtgtga　　　　　　　　　　　　　　　　　　　　　18

<210> SEQ ID NO 195
<211> LENGTH: 21
<212> TYPE: DNA
<213> ORGANISM: Artificial Sequence
<220> FEATURE:
<223> OTHER INFORMATION: mCB2-E1a R (reverse primer)

<400> SEQUENCE: 195
ttgtcctggc tattctgtat c　　　　　　　　　　　　　　　　　　21

<210> SEQ ID NO 196
<211> LENGTH: 22
<212> TYPE: DNA
<213> ORGANISM: Artificial Sequence
<220> FEATURE:
<223> OTHER INFORMATION: mCB2-E1a P

<400> SEQUENCE: 196
ctggagctgc agctcttggg ac　　　　　　　　　　　　　　　　　　22

<210> SEQ ID NO 197
<211> LENGTH: 17
<212> TYPE: DNA
<213> ORGANISM: Artificial Sequence
<220> FEATURE:
<223> OTHER INFORMATION: mCB2-E1b F (forward primer)

<400> SEQUENCE: 197
acacatagcc tggcaca　　　　　　　　　　　　　　　　　　　　　17

```
<210> SEQ ID NO 198
<211> LENGTH: 19
<212> TYPE: DNA
<213> ORGANISM: Artificial Sequence
<220> FEATURE:
<223> OTHER INFORMATION: mCB2-E1b R (reverse primer)

<400> SEQUENCE: 198
gcggttgaat tctctcttc                                                19

<210> SEQ ID NO 199
<211> LENGTH: 25
<212> TYPE: DNA
<213> ORGANISM: Artificial Sequence
<220> FEATURE:
<223> OTHER INFORMATION: mCB2-E1b P

<400> SEQUENCE: 199
tcaagtgagt tgcaggacag catac                                         25

<210> SEQ ID NO 200
<211> LENGTH: 19
<212> TYPE: DNA
<213> ORGANISM: Artificial Sequence
<220> FEATURE:
<223> OTHER INFORMATION: mCB2-E2 F (forward primer)

<400> SEQUENCE: 200
ttctagaagg cacccatgt                                                19

<210> SEQ ID NO 201
<211> LENGTH: 20
<212> TYPE: DNA
<213> ORGANISM: Artificial Sequence
<220> FEATURE:
<223> OTHER INFORMATION: mCB2-E2 R (reverse primer)

<400> SEQUENCE: 201
cctctgctca ttcaggtaca                                               20

<210> SEQ ID NO 202
<211> LENGTH: 23
<212> TYPE: DNA
<213> ORGANISM: Artificial Sequence
<220> FEATURE:
<223> OTHER INFORMATION: mCB2-E2 P

<400> SEQUENCE: 202
cttcctgttg ctgtgtgcat cct                                           23

<210> SEQ ID NO 203
<211> LENGTH: 20
<212> TYPE: DNA
<213> ORGANISM: Artificial Sequence
<220> FEATURE:
<223> OTHER INFORMATION: Beta-actin F (forward primer)

<400> SEQUENCE: 203
gggaatgggt cagaaggact                                               20

<210> SEQ ID NO 204
<211> LENGTH: 20
<212> TYPE: DNA
<213> ORGANISM: Artificial Sequence
<220> FEATURE:
<223> OTHER INFORMATION: Beta-actin R (reverse primer)
```

<400> SEQUENCE: 204
aggtgtggtg ccagatcttc                                          20

<210> SEQ ID NO 205
<211> LENGTH: 25
<212> TYPE: DNA
<213> ORGANISM: Artificial Sequence
<220> FEATURE:
<223> OTHER INFORMATION: Beta-actin P

<400> SEQUENCE: 205
atgtgggtga cgaggcccag agcaa                                    25

<210> SEQ ID NO 206
<211> LENGTH: 18
<212> TYPE: DNA
<213> ORGANISM: Artificial Sequence
<220> FEATURE:
<223> OTHER INFORMATION: E1-352F (forward primer)

<400> SEQUENCE: 206
ggcacatgtc acagacaa                                            18

<210> SEQ ID NO 207
<211> LENGTH: 20
<212> TYPE: DNA
<213> ORGANISM: Artificial Sequence
<220> FEATURE:
<223> OTHER INFORMATION: E1+123R (reverse primer)

<400> SEQUENCE: 207
gcgaagagtt agggaagagt                                          20

<210> SEQ ID NO 208
<211> LENGTH: 18
<212> TYPE: DNA
<213> ORGANISM: Artificial Sequence
<220> FEATURE:
<223> OTHER INFORMATION: E1-14F (forward primer)

<400> SEQUENCE: 208
cctgctgggt ctccagat                                            18

<210> SEQ ID NO 209
<211> LENGTH: 20
<212> TYPE: DNA
<213> ORGANISM: Artificial Sequence
<220> FEATURE:
<223> OTHER INFORMATION: E1+123R (reverse primer)

<400> SEQUENCE: 209
gcgaagagtt agggaagagt                                          20

<210> SEQ ID NO 210
<211> LENGTH: 18
<212> TYPE: DNA
<213> ORGANISM: Artificial Sequence
<220> FEATURE:
<223> OTHER INFORMATION: E1-441F (forward primer)

<400> SEQUENCE: 210
gttcaattcc cagcaccc                                            18

```
<210> SEQ ID NO 211
<211> LENGTH: 19
<212> TYPE: DNA
<213> ORGANISM: Artificial Sequence
<220> FEATURE:
<223> OTHER INFORMATION: E1-19R (reverse primer)

<400> SEQUENCE: 211
cccacgtagg tcccaagag                                             19

<210> SEQ ID NO 212
<211> LENGTH: 20
<212> TYPE: DNA
<213> ORGANISM: Artificial Sequence
<220> FEATURE:
<223> OTHER INFORMATION: E2-F189 (forward primer)

<400> SEQUENCE: 212
cttgccagtt cccagtttca                                            20

<210> SEQ ID NO 213
<211> LENGTH: 21
<212> TYPE: DNA
<213> ORGANISM: Artificial Sequence
<220> FEATURE:
<223> OTHER INFORMATION: E2+R36 (reverse primer)

<400> SEQUENCE: 213
caagtcacat gggtgccttc t                                          21

<210> SEQ ID NO 214
<211> LENGTH: 20
<212> TYPE: DNA
<213> ORGANISM: Artificial Sequence
<220> FEATURE:
<223> OTHER INFORMATION: E2-F90 (forward primer)

<400> SEQUENCE: 214
agaagaggga cttgcccaaa                                            20

<210> SEQ ID NO 215
<211> LENGTH: 21
<212> TYPE: DNA
<213> ORGANISM: Artificial Sequence
<220> FEATURE:
<223> OTHER INFORMATION: E2+R36 (reverse primer)

<400> SEQUENCE: 215
caagtcacat gggtgccttc t                                          21

<210> SEQ ID NO 216
<211> LENGTH: 20
<212> TYPE: DNA
<213> ORGANISM: Artificial Sequence
<220> FEATURE:
<223> OTHER INFORMATION: E2+F13 (forward primer)

<400> SEQUENCE: 216
tctagaaggc acccatgtga                                            20

<210> SEQ ID NO 217
<211> LENGTH: 20
<212> TYPE: DNA
<213> ORGANISM: Artificial Sequence
<220> FEATURE:
<223> OTHER INFORMATION: E2+R205 (reverse primer)
```

-continued

```
<400> SEQUENCE: 217
ctgtgcctct gctcattcag                                            20

<210> SEQ ID NO 218
<211> LENGTH: 20
<212> TYPE: DNA
<213> ORGANISM: Artificial Sequence
<220> FEATURE:
<223> OTHER INFORMATION: E2-F189 (forward primer)

<400> SEQUENCE: 218
cttgccagtt cccagtttca                                            20

<210> SEQ ID NO 219
<211> LENGTH: 20
<212> TYPE: DNA
<213> ORGANISM: Artificial Sequence
<220> FEATURE:
<223> OTHER INFORMATION: E2+R101 (reverse primer)

<400> SEQUENCE: 219
aacaggatgc acacagcaac                                            20

<210> SEQ ID NO 220
<211> LENGTH: 20
<212> TYPE: DNA
<213> ORGANISM: Artificial Sequence
<220> FEATURE:
<223> OTHER INFORMATION: E2-F25 (forward primer)

<400> SEQUENCE: 220
tcaaacacat ccttgcccta                                            20

<210> SEQ ID NO 221
<211> LENGTH: 20
<212> TYPE: DNA
<213> ORGANISM: Artificial Sequence
<220> FEATURE:
<223> OTHER INFORMATION: E2+R101 (reverse primer)

<400> SEQUENCE: 221
aacaggatgc acacagcaac                                            20
```

CANNABINOID 2 ($CB_2$) RECEPTOR GENE PROMOTER AND UNIQUE RNA TRANSCRIPTS IN B CELLS AND METHODS OF USE

CROSS-REFERENCE TO RELATED APPLICATION

The present application claims the benefit of U.S. Application Ser. No. 61/235,326, filed Aug. 19, 2009, which is hereby incorporated by reference herein in its entirety, including any figures, tables, nucleic acid sequences, amino acid sequences, and drawings.

GOVERNMENT SUPPORT

This invention was made with government support under Grant No. R01 DA019824 awarded by the National Institutes of Health. The government has certain rights in the invention.

FIELD OF INVENTION

This invention relates to immunology and control of the allergic response. More specifically, this invention relates to DNA sequences of the cannabinoid receptor 2 gene promoter and sequences of derived RNA gene transcripts as produced in immune B cells, and methods of employing the sequences allowing for the genetic manipulation of this receptor in B cells to effect the suppression of production of the allergic antibody, thereby reducing allergic disease.

BACKGROUND OF THE INVENTION

The physiological basis of many seasonal allergies is the overproduction in the allergic patient of the allergic antibody, termed immunoglobulin E (IgE). This antibody is produced by specialized immune cells called B cells. IgE antibody can be over-produced in response to allergens (antigens) inhaled by allergic patients and this excess antibody combines with the allergen in the upper airways leading to the symptoms of allergy, such as itchy, watery eyes, runny nose, and even asthma. Understanding the basis for the overproduction of IgE in allergic patients is the goal of many studies by pharmaceutical companies. It is believed that by a deeper understanding of the basis of the allergic response, more effective therapies can be devised for prevention of the over-response. A central question in this area involves an understanding of the molecular mechanisms surrounding immunoglobulin (Ig) class switching in B cells (P. Takhar et al., *Journal of Immunology*, 2005, 174:5024-5032) from protective IgG antibodies to allergic IgE antibodies.

The peripheral cannabinoid receptor ($CB_2$) was first identified in 1993 by Munro et al. (*Nature*, 365:61-65) via cloning of a novel G-protein coupled receptor expressed in the human cell line, HL60, which bound to cannabinoids with relatively high affinity. Since its discovery, the expression of $CB_2$ is shown to be almost exclusively on cells of the immune system, with the ranking order of abundance being B cells>NK cells>macrophages>T cells (Galieque et al., *Eur. J. Biochem.*, 1995, 232:54-61; Carayon et al., *Blood*, 1998, 92:3605-3615; Lee et al., *Eur. J. Pharmacol.*, 2000, 423:235-241). Though B cells appear to express more $CB_2$ receptor than other immune cell types, little is known about the role this receptor plays in B cell activation and overall biology. There is some evidence that $CB_2$ signaling may be involved in B cell differentiation, migration, proliferation and antibody class switching, suggesting the receptor is a part of the B cell immune activation program (Carayon et al., *Blood*, 1998, 92:3605-3615; Jorda et al., *Blood*, 2002, 99:2786-2793; Rayman et al., *J Immunol*, 2004, 172:2111-2117; Massi et al., *J Neuroimmunol*, 1998, 92(1-2):60-6; Marchand et al., *Cytometry*, 1999, 35(3):227-34; Jorda et al., *Ann N Y Acad. Sci.*, 2003, 996:10-6; Agudelo et al., *Journal of NeuroImmune Pharmacology*, 2008, 3:35-42). However, the mechanisms involved in $CB_2$ receptor gene (CNR2) regulation and at what stage in B cell activation this process occurs have been unclear. Identifying the structure of the CNR2 gene promoter and the spectrum of transcription factors involved in gene regulation will help elucidate the role of $CB_2$ in B cell biology. In this regard, several reports suggest that CD40 on B cells as well as stimulation by IL-4, and activation of STAT6, increases $CB_2$ expression; whereas, LPS stimulation reportedly suppresses $CB_2$ mRNA expression in B cells (Carayon et al., *Blood*, 1998, 92:3605-3615; Lee et al., *Eur. J. Pharmacol.*, 2000, 423:235-241; Schroder et al., *J Immunol*, 2002, 168:996-1000; Agudelo et al., *Journal of NeuroImmune Pharmacology*, 2008, 3:35-42; Lee et al., *Adv Exp Med Biol*, 2001, 493:223-228). Though these studies provide some clues to regulation of $CB_2$ expression in activated B cells, more studies are needed to define the factors that regulate CNR2 gene expression and $CB_2$ protein in normal B cells.

The core promoter is the minimal region of DNA required for RNA polymerase II (Pol II) to assemble with the general transcription factors and form the pre-initiation complex for initiation of activator-independent (basal) transcription (Gross and Oelgeschlager, *Biochem Soc Symp*, 2006, 73:225-236). At the center of the core promoter is the initiator (INR) sequence that contains the transcription start site (TSS), which is defined as the most 5' nucleotide of mRNA transcribed by Pol II (Gross and Oelgeschlager, *Biochem Soc Symp*, 2006, 73:225-236; Sandelin et al., *Nat Rev Genet*, 2007, 8:424-436). Correct identification of the TSS in primary resting B cells will lead to the location of the CNR2 core promoter, including core and cis-acting elements, and provide insights into the molecular mechanisms involved in $CB_2$ expression.

SUMMARY OF THE INVENTION

Described herein are $CB_2$ transcription start sites (TSSs) associated with the core promoter in resting mouse primary splenic and human peripheral B cells, and other results from the inventors' investigation of $CB_2$ mRNA transcript production in mouse resting and LPS activated primary B cells.

The present inventors have demonstrated that marijuana cannabinoids can induce, in an animal model, antibody class switching similar to that occurring in human allergy (C. Newton et al. *Infection and Immunity*, 2004, 62:4015-4020, which is incorporated herein by reference in its entirety). More recently, the inventors have produced data suggesting that cannabinoids do this through the stimulation of cannabinoid 2 ($CB_2$) receptor proteins on B cells. These data provide a basis for controlling IgE production through $CB_2$ receptors. Therefore, treatments designed to inhibit $CB_2$ receptor expression could suppress IgE production. The gene promoter region on the chromosome responsible for regulating the expression of the $CB_2$ receptor gene, and therefore the expression of $CB_2$ receptor proteins on B cells, has not been described previously and forms the basis of an aspect of the present invention. Although the promoter is described herein in the context of mouse B cells, the inventors propose that the promoter in human B cells is very similar to that of the mouse B cells used as a point of reference/basis for the description of the invention, and thus, application in the context of the human B cells, as well as other non-human mammals/animals, is contemplated. Therefore, it is contemplated that, using the systems and methods herein described, the expression of the $CB_2$ receptors on human B cells can be suppressed resulting in a method of inhibiting the overproduction of IgE and the symptoms of allergy. The identification of TSSs and preferential expression of select $CB_2$ transcripts of the invention are also described in Sherwood T. A. et al., *J. Neuroimmune Pharmacol.*, 2009, 4:476-488, which is incorporated herein by reference in its entirety).

An aspect of the present invention includes the location and linear DNA structure of the marijuana cannabinoid $CB_2$ receptor gene promoter region on chromosome 4 in mouse B cells. A derivative of these promoters, and therefore also a part of this invention, are the RNA nucleotide sequences of the genetic message or transcripts that are produced from this gene and unique to B cells. The mouse gene promoter provided by the invention is termed "promoter 1" and represents 809 nucleotide base pairs of DNA located on chromosome 4, along with derivatives and analogs of the promoter 1. Promoter 1 is located 5' to intron 1 and upstream of exon 2, intron 2, and exon 3 (the $CB_2$ open reading frame, ORF) (see model of gene and nucleotide sequence as described in the following sections). The mouse promoter 1 nucleotide sequence has been shown by us using gene expression techniques to regulate the expression of the $CB_2$ gene in B cells and, as such, may be modified and manipulated by various genetic techniques in the control of B cell functions, including the production of IgE. It is contemplated that a second promoter, promoter 2, exists with a similar sequence and structure to that of promoter 1 and is therefore also involved in the regulation of the expression of the mouse $CB_2$ gene. This second promoter region is also subject to manipulation thus controlling the expression of $CB_2$ and B cell function. The corresponding location and structure of the $CB_2$ receptor gene promoter region of human B cells is another aspect of the invention.

Direct derivatives of promoter 1 and another aspect of this invention are unique 5' ribonucleotide fragments termed unique gene transcript fragments 1, 2, 3, and 4 with defined ribonucleotide sequences. The production of these unique fragments in B cells has been validated by the inventors using the 5'RACE technique and nucleotide sequencing. These RNA sequences are a part of the invention and contain nucleotide sequences unique to B cells and as such have the potential to be manipulated by nucleic acid-based inhibitory techniques such as interfering RNA (RNAi), antisense, and ribozyme methodologies in order to suppress $CB_2$ receptor expression in these cells.

The "holy grail" in allergy management is to control the production of allergic antibodies of the IgE type in the patient. This invention provides mechanisms for controlling IgE production in people. One important use for this invention is in the design of reagents for use in gene therapy for allergic and other diseases. For example, aspects of the invention provide key tools for evaluating the effects of substances (e.g., compounds) on the promoter 1 nucleotide sequence. At present, numerous investigators are actively engaged in the development of reagents to suppress IgE production. The present invention provides those IgE suppression reagents (e.g., inhibitory nucleic acid molecules such as RNA interference (RNAi)-inducing molecules, antisense oligonucleotides, ribozymes, and constructs that induce targeted gene deletion upon insertion) and their nucleic acid targets.

In a first aspect, the present invention provides an isolated and purified nucleic acid molecule encoding a cannabinoid receptor 2 gene promoter (promoter 1). The promoter 1 can be a molecule selected from the group consisting of: (a) a cannabinoid receptor 2 gene promoter nucleic acid sequence or derivative or analogue thereof; (b) a promoter 1 or promoter 2 nucleic acid sequence or derivative or analogue thereof; (c) a cannabinoid receptor 2 gene promoter nucleic acid sequence as set forth in SEQ ID NO: 1; (d) a biologically active cannabinoid receptor 2 gene promoter nucleic acid sequence as set forth in SEQ ID NO: 1; (e) a cannabinoid receptor 2 gene promoter encoded by a nucleic acid molecule comprising a nucleic acid sequence having 40%, 42%, 44%, 46%, 48%, 50%, 52%, 54%, 56%, 58%, 60%, 62%, 64%, 66%, 68%, 70%, 72%, 74%, 76%, 78%, 80%, 82%, 84%, 86%, 88%, 90%, 92%, 94%, 96%, 98%, or greater sequence identity to SEQ ID NO: 1 (FIG. 8); (f) a biologically active cannabinoid receptor 2 gene promoter encoded by a nucleic acid molecule comprising a nucleic acid sequence having 40%, 42%, 44%, 46%, 48%, 50%, 52%, 54%, 56%, 58%, 60%, 62%, 64%, 66%, 68%, 70%, 72%, 74%, 76%, 78%, 80%, 82%, 84%, 86%, 88%, 90%, 92%, 94%, 96%, 98%, or greater sequence identity to SEQ ID NO: 1 (FIG. 8); (g) a biologically active cannabinoid receptor 2 gene promoter encoded by a nucleic acid molecule comprising a nucleic acid sequence having 40%, 42%, 44%, 46%, 48%, 50%, 52%, 54%, 56%, 58%, 60%, 62%, 64%, 66%, 68%, 70%, 72%, 74%, 76%, 78%, 80%, 82%, 84%, 86%, 88%, 90%, 92%, 94%, 96%, 98%, or greater sequence identity to SEQ ID NO: 1 (FIG. 8); (h) a biologically active cannabinoid receptor 2 gene promoter encoded by a nucleic acid molecule comprising a nucleic acid sequence having 40%, 42%, 44%, 46%, 48%, 50%, 52%, 54%, 56%, 58%, 60%, 62%, 64%, 66%, 68%, 70%, 72%, 74%, 76%, 78%, 80%, 82%, 84%, 86%, 88%, 90%, 92%, 94%, 96%, 98%, or greater sequence identity to 50 contiguous nucleotides of SEQ ID NO: 1 (FIG. 17); (i) a biologically active cannabinoid receptor 2 gene promoter encoded by a nucleic acid molecule comprising a nucleic acid sequence having 40%, 42%, 44%, 46%, 48%, 50%, 52%, 54%, 56%, 58%, 60%, 62%, 64%, 66%, 68%, 70%, 72%, 74%, 76%, 78%, 80%, 82%, 84%, 86%, 88%, 90%, 92%, 94%, 96%, 98%, or greater sequence identity to 75 contiguous nucleotides of SEQ ID NO: 1 (FIG. 17); (j) a biologically active cannabinoid receptor 2 gene promoter encoded by a nucleic acid molecule comprising a nucleic acid sequence having 40%, 42%, 44%, 46%, 48%, 50%, 52%, 54%, 56%, 58%, 60%, 62%, 64%, 66%, 68%, 70%, 72%, 74%, 76%, 78%, 80%, 82%, 84%, 86%, 88%, 90%, 92%, 94%, 96%, 98%, or greater sequence identity to 100 contiguous nucleotides of SEQ ID NO: 1 (FIG. 17); (k) a biologically active cannabinoid receptor 2 gene promoter encoded by a nucleic acid molecule comprising a nucleic acid sequence having 40%, 42%, 44%, 46%, 48%, 50%, 52%, 54%, 56%, 58%, 60%, 62%, 64%, 66%, 68%, 70%, 72%, 74%, 76%, 78%, 80%, 82%, 84%, 86%, 88%, 90%, 92%, 94%, 96%, 98%, or greater sequence identity to 150 contiguous nucleotides of SEQ ID NO: 1 (FIG. 17); (l) a biologically active cannabinoid receptor 2 gene promoter encoded by a nucleic acid molecule comprising a nucleic acid sequence having 40%, 42%, 44%, 46%, 48%, 50%, 52%, 54%, 56%, 58%, 60%, 62%, 64%, 66%, 68%, 70%, 72%, 74%, 76%, 78%, 80%, 82%, 84%, 86%, 88%, 90%, 92%, 94%, 96%, 98%, or greater sequence identity to 200 contiguous nucleotides of SEQ ID NO: 1 (FIG. 17); (m) a cannabinoid receptor 2 gene promoter encoded by a nucleic acid molecule comprising a nucleic acid sequence having 40%, 42%, 44%, 46%, 48%, 50%, 52%, 54%, 56%, 58%, 60%, 62%, 64%, 66%, 68%, 70%, 72%, 74%, 76%, 78%, 80%, 82%, 84%, 86%, 88%, 90%, 92%, 94%, 96%, 98%, or greater sequence identity to 30, 40, 60, 70, 80, 90, 100, 110, 120, 130, 140, 150, 160, 180, 200, 220, 240, 250, 275, 300, 325, 350, 375, 400, 425, 450, 475, 500, 550, 600 or more contiguous nucleotides of SEQ ID NO: 1 (FIG. 17); and (n) a biologically active cannabinoid receptor 2 gene promoter encoded by a nucleic acid molecule comprising a nucleic acid sequence having 40%, 42%, 44%, 46%, 48%, 50%, 52%, 54%, 56%, 58%, 60%, 62%, 64%, 66%, 68%, 70%, 72%, 74%, 76%, 78%, 80%, 82%, 84%, 86%, 88%, 90%, 92%, 94%, 96%, 98%, or greater sequence identity to 10, 20, 30, 40, 60, 70, 80, 90, 100, 110, 120, 130, 140, 150, 160, 180, 200, 220, 240, 250, 275, 300, 325, 350, 375, 400, 425, 450, 475, 500, 550, 600 or more contiguous nucleotides of SEQ ID NO: 1 (FIG. 17).

In a second aspect the present invention provides a method of screening for an allergen. The method can include the steps of providing a cell having a construct comprising a cannabinoid receptor 2 gene promoter and a reporter gene, contacting the cell with one or more substances (i.e., compounds) to be tested as an allergen and measuring the resulting reporter gene expression. In certain embodiments the cannabinoid receptor 2 gene promoter is a promoter selected from the promoters of the first aspect.

In a third aspect the present invention provides a method of screening for an anti-allergen. The method can include the steps of providing a cell having a construct comprising a cannabinoid receptor 2 gene promoter and a reporter gene, contacting the cell with an allergen and one or more candidate substances (i.e., compounds) to be tested as an anti-allergen and measuring the resulting reporter gene expression. The resulting reporter gene expression can further be compared to the reporter gene expression of a cell contacted with only an allergen. In certain embodiments the cannabinoid receptor 2 gene promoter is a promoter selected from the promoters of the first aspect. Down-regulation of the reporter gene can be used to indicate that the screened compound is a potential anti-allergen.

In a fourth aspect the present invention provides a method of regulating the expression of the $CB_2$ receptor gene (CNR2). The method can include the step of contacting a cell with one or more substances (e.g., compounds) that interact with the $CB_2$ gene promoter region or transcript. In certain embodiments, the promoter can be selected from the group consisting of promoter 1 and promoter 2. In some embodiments, the compounds are inhibitory nucleic acid molecules such as interfering RNA (e.g., siRNA, shRNA), antisense oligonucleotides, ribozymes, or constructs that result in targeted deletion of the CNR2 gene.

In a fifth aspect the present invention provides a method of regulating the immunoglobulin E (IgE)-mediated allergic response. The method can include the step of contacting a cell with one or more substances (i.e., compounds) that interacts with the $CB_2$ gene promoter region. In certain embodiments the promoter can be selected from the group consisting of promoter 1 and promoter 2. In some embodiments, the compounds are inhibitory nucleic acid molecules such as interfering RNA (e.g., siRNA, shRNA), antisense oligonucleotides, or ribozymes.

In a sixth aspect the present invention provides an isolated and purified nucleic acid molecule encoding a cannabinoid receptor 2 gene. Exemplary nucleic acids are provided in the appended claims.

In a seventh aspect the present invention provides a reporter vector comprising a $CB_2$ gene promoter (or a derivative or analog thereof) and a reporter gene. In certain embodiments the reporter vector can utilize a $CB_2$ gene promoter that corresponds to a promoter 1 fragment as provided in FIG. 13, or a derivative or analog of said promoter 1 fragment. The reporter vector can utilize reporter genes such as luciferase.

In an eighth aspect the present invention provides an isolated and purified amino acid encoded by the nucleic acids of the present invention.

In a ninth aspect the present invention provides a method of regulating (reducing) the expression of a B cell $CB_2$ receptor gene (CNR2), comprising contacting a cell with one or more compounds that directly or indirectly interacts with the $CB_2$ gene promoter region or transcript within the cell, thereby regulating expression of the B cell $CB_2$ receptor gene. In some embodiments, the cell is a B cell. In some embodiments, the $CB_2$ gene promoter region is not native to the cell (e.g., the cell has been genetically modified to express the $CB_2$ gene). In some embodiments, the one or more compounds comprise an inhibitory nucleic acid molecule that reduces expression of the B cell $CB_2$ receptor gene. In some embodiments, the inhibitory nucleic acid molecule targets a human $CB_2$ gene promoter region comprising at least one region selected from among the transcription start site (tss) for human exon 1, or at least a portion of the 3' or 5' untranslated region (UTR) for human exon 1 (FIG. 10; FIG. 14B). In some embodiments, the inhibitory nucleic acid molecule targets mouse CB2 gene promoter region comprising at least one region selected from among the transcription start site (tss) for mouse exon 1a, mouse exon 1b, or mouse exon 2, or at least a portion of the 3' or 5' UTR for mouse exon 1a, mouse exon 1b, or mouse exon 2 (FIG. 9; FIG. 14A). In some embodiments, the inhibitory nucleic acid molecule comprises a nucleic acid sequence that is complementary with a target nucleic acid sequence within or overlapping with the B cell $CB_2$ gene promoter region or a transcript thereof. In some embodiments, the inhibitory nucleic acid molecule is selected from among an interfering RNA (RNAi) molecule, an antisense oligonucleotide, a ribozyme, and a construct that causes targeted deletion of the $CB_2$ gene (e.g., induces a recombination event upon insertion into the B cell $CB_2$ gene promoter region). In some embodiments, the inhibitory nucleic acid molecule comprises short interfering RNA (siRNA) or short hairpin RNA (shRNA). In some embodiments, the contacting step comprises contacting a viral or non-viral vector with the cell, and the viral or non-viral vector is carrying the inhibitory nucleic acid molecule, or carrying a nucleic acid molecule encoding the inhibitory nucleic acid, wherein the nucleic acid molecule encoding the inhibitory nucleic acid molecule is operably linked to a promoter that drives expression of the nucleic acid molecule encoding the inhibitory nucleic acid molecule (e.g., in the case of shRNA).

In some embodiments, the $CB_2$ gene promoter region targeted by the one or more compounds comprises at least one region selected from among the transcription start site (tss) for human exon 1, or at least a portion of the 3' or 5' untranslated region (UTR) for human exon 1 (FIG. 10; FIG. 14B). In some embodiments, the $CB_2$ gene promoter region targeted by the one or more compounds comprises at least one region selected from among the transcription start site (tss) for mouse exon 1a, mouse exon 1b, or mouse exon 2, or at least a portion of the 3' or 5' UTR for mouse exon 1a, mouse exon 1b, or mouse exon 2 (FIG. 9; FIG. 14A).

In some embodiments, the one or more compounds (e.g., inhibitory nucleic acid molecules) target a sequence within the following sequence of the human $CB_2$ gene promoter region or transcript: GGCACTCAACAGGTGCTCTG AGTGGCACCCACGGCCAGGTCCTGG-GAGAGGACAGAAAACAACTGGGACTCCTC A (SEQ ID NO: 6) (FIG. 33). In some embodiments, the compound is an interfering RNA molecule comprising the nucleic acid sequence GGUGCUCUGAGUGGCACCC (SEQ ID NO: 7)

or CACUCAACAGGUGCUCUGA (SEQ ID NO: 8), which target positions 12-30 and 3-21, respectively (FIG. 33).

In some embodiments, the one or more compounds (e.g., inhibitory nucleic acid molecules) target a sequence within the following sequence of the mouse CB$_2$ gene promoter region or transcript:

(SEQ ID NO: 9)
AGAAATAGGTCTTCTAGAAGGCACCCATGTGACTTGCAGAGGGTATCTCT

ATCTTCGTGGAGACAGGGAGCCGGGCTTCCTGTTGCTGTGTGCATCCTGT

TGTTCTCTTGTTAGGATGTCCATCAAATGCATGCATTTCCTTTCCTAACT

CTGGACAGTAACAGTCGTCTGCGGCCAAGCTGTGCCTGAATGAGCAGAGG

CACAGGCACCAGCCGTGGCCACCCAGCAAACATCTCTGCTGACTCAGACT

GGG (mouse Exon 2, FIG. 31A). In some embodiments, the compound is an interfering RNA molecule comprising at least one nucleic acid sequence from among:

| | |
|---|---|
| GCAUUUCCUUUCCUAACUC; | (SEQ ID NO: 10) |
| GACUUGCAGAGGGUAUCUC; | (SEQ ID NO: 11) |
| GCCACCCAGCAAACAUCUC; | (SEQ ID NO: 12) |
| GUUCUCUUGUUAGGAUGUC; | (SEQ ID NO: 13) |
| GUGACUUGCAGAGGGUAUC; | (SEQ ID NO: 14) |
| GAGCCGGGCUUCCUGUUGC; | (SEQ ID NO: 15) |
| GUCUGCGGCCAAGCUGUGC; | (SEQ ID NO: 16) |
| GCUUCCUGUUGCUGUGUGC; | (SEQ ID NO: 17) |
| GACAGUAACAGUCGUCUGC; | (SEQ ID NO: 18) |
| GGUCUUCUAGAAGGCACCC; | (SEQ ID NO: 19) |
| GAGCAGAGGCACAGGCACC; | (SEQ ID NO: 20) |
| GUAACAGUCGUCUGCGGCC; | (SEQ ID NO: 21) |
| AUAGGUCUUCUAGAAGGCA; | (SEQ ID NO: 22) |
| UGGACAGUAACAGUCGUCU; | (SEQ ID NO: 23) |
| UCCUAACUCUGGACAGUAA; | (SEQ ID NO: 24) |
| CACCCAUGUGACUUGCAGA; | (SEQ ID NO: 25) |
| CCAUCAAAUGCAUGCAUUU; | (SEQ ID NO: 26) |
| AAACAUCUCUGCUGACUCA; | (SEQ ID NO: 27) |
| GCAGAGGGUAUCUCUAUCU; | (SEQ ID NO: 28) |
| GUUAGGAUGUCCAUCAAAU; | (SEQ ID NO: 29) |
| GUCCAUCAAAUGCAUGCAU; | (SEQ ID NO: 30) |
| GGAUGUCCAUCAAAUGCAU; | (SEQ ID NO: 31) |
| GCAUGCAUUUCCUCCUAAC; | (SEQ ID NO: 32) |
| GUUGUUCUCUUGUUAGGAU; | (SEQ ID NO: 33) |
| UCUUGUUAGGAUUCCAUCA; | (SEQ ID NO: 34) |
| GUAUCUCUAUCUUCGUGGA; | (SEQ ID NO: 35) |
| CCUUUCCUAACUCUGGACA; | (SEQ ID NO: 36) |
| CAUUUCCUUUCCUAACUCU; | (SEQ ID NO: 37) |
| UGCAUUUCCUUUCCUAACU; | (SEQ ID NO: 38) |
| and | |
| CAGCAAACAUCUCUGCUGA | (SEQ ID NO: 39) |
| (FIG. 31B). | |

In some embodiments, the compound is an inhibitory nucleic acid molecule that targets a sequence within the following sequence of the mouse CB$_2$ gene promoter region:

(SEQ ID NO: 40)
ACATAGCGTGGCACATGTCACAGACAAAAGGATGTAAACTTTACAGAGGT

CAAGTGAGTTGCAGGACAGCATACACCCGGGGCCAGATTAGAACCCAAGT

TTCTGGAGTCTAAGGTCTATGCCTATGCCCTCCCCTGGCCAGAGTTCCTA

GGAAGAGAGAATTCAACCGCAGGGCAAGAACACTGTGGCACTGAGGACCC

AGAGGGGAAGTGGTAACCGGTACGGAAGGCCAGATCTCCTCTCACTCACT

TATCTGCACCAGACCTCCTCTCATTCACTCATTTGCGAAAGTGTGAGAGC

AAGAAACCCCAGGCTGGAGCTGCAGCTCTTGGGACCTACGTGGGGGTCCC

TGCTGGGTCTCCAGATCTGGATACAGAATAGCCAGGACAAGGCTCCACAA

GACCCTGGGGCCCAGCGGCTGACAAATGACA (mouse Exon 1b (which contains mouse Exon 1a); FIG. 32A). In some embodiments, the compound is an interfering RNA molecule comprising at least one nucleic acid sequence from among:

| | |
|---|---|
| GAUCUGGAUACAGAAUAGC; | (SEQ ID NO: 41) |
| GUUGCAGGACAGCAUACAC; | (SEQ ID NO: 42) |
| GGACAAGGCUCCACAAGAC; | (SEQ ID NO: 43) |
| GAGUUGCAGGACAGCAUAC; | (SEQ ID NO: 44) |
| GUACGGAAGGCCAGAUCUC; | (SEQ ID NO: 45) |
| CUCCAGAUCUGGAUACAGA; | (SEQ ID NO: 46) |
| GUGUGAGAGCAAGAAACCC; | (SEQ ID NO: 47) |
| GACAAGGCUCCACAAGACC; | (SEQ ID NO: 48) |
| GUUUCUGGAGUCUAAGGUC; | (SEQ ID NO: 49) |
| GCCAGAUCUCCUCUCACUC; | (SEQ ID NO: 50) |
| CCUCCUCUCAUUCACUCAU; | (SEQ ID NO: 51) |
| GGAGUCUAAGGUCUAUGCC; | (SEQ ID NO: 52) |
| GGGAAGUGGUAACCGGUAC; | (SEQ ID NO: 53) |
| GAAGGCCAGAUCUCCUCUC; | (SEQ ID NO: 54) |
| GGUAACCGGUACGGAAGGC; | (SEQ ID NO: 55) |
| GUCAAGUGAGUUGCAGGAC; | (SEQ ID NO: 56) |
| GGAUACAGAAUAGCCAGGA; | (SEQ ID NO: 57) |
| GAAGAGAGAAUUCAACCGC; | (SEQ ID NO: 58) |
| GUAACCGGUACGGAAGGCC; | (SEQ ID NO: 59) |
| GGCAAGAACACUGUGGCAC; | (SEQ ID NO: 60) |

-continued

| | |
|---|---|
| GAGCUGCAGCUCUUGGGAC; | (SEQ ID NO: 61) |
| GUCUAUCGGUAUGCCCUCC; | (SEQ ID NO: 62) |
| GAGAAUUCAACCGCAGGGC; | (SEQ ID NO: 63) |
| GGUCUAUGCCUAUGCCCUC; | (SEQ ID NO: 64) |
| GGCCAGAUUAGAACCCAAG; | (SEQ ID NO: 65) |
| UUCUGGAGUCUAAGGUCUA; | (SEQ ID NO: 66) |
| CCAAGUUUCUGGAGUCUAA; | (SEQ ID NO: 67) |
| AGUCUAAGGUCUAUGCCUA; | (SEQ ID NO: 68) |
| CUCCAGAUCUGGAUACAGA; | (SEQ ID NO: 69) |
| CUGGCCAGAGUUCCUAGGA; | (SEQ ID NO: 70) |
| CCAGAGUCCUAGGAAGAGA; | (SEQ ID NO: 71) |
| GGCAAGAACACUGUGGCAC; | (SEQ ID NO: 72) |
| CACCAGACCUCCUCUCAUC; | (SEQ ID NO: 73) |
| ACAGACAAAAGGAUGUAAA; | (SEQ ID NO: 74) |
| GUUCCUAGGAAGAGAGAAU; | (SEQ ID NO: 75) |
| CCUAGGAAGAGAGAAUUCA; | (SEQ ID NO: 76) |
| GAAAGUGUGAGAGCAAGAA; | (SEQ ID NO: 77) |
| GAACCCAAGUUUCUGGAGU; | (SEQ ID NO: 78) |
| CAUUCACUCAUUUGCGAAA; | (SEQ ID NO: 79) |
| CACUCACUUAUCUGCACCA; | (SEQ ID NO: 80) |
| CUCAUUCACUCAUUUGCGA; | (SEQ ID NO: 81) |
| CAUUUGCGAAAGUGUGAGA; and | (SEQ ID NO: 82) |
| GUAAACUUUACAGAGGUCA (FIG. 32B). | (SEQ ID NO: 83) |

In some embodiments, the one or more compounds (e.g., inhibitory nucleic acid molecules) are contacted with the cell in vivo, wherein the contacting step comprises administering the one or more compounds to a human or non-human subject. Preferably, an effective amount of one or more compounds are administered such that it results in regulation (reduction) of an IgE-mediated allergic response in the subject. In some embodiments, the subject has an IgE-mediated allergic disease, and administration of the one or more compounds (by themselves or administered simultaneously or consecutively with other agents) alleviates one or more symptoms of the allergic disease.

The method of the invention may be used to treat (therapeutically or prophylactically) an IgE-mediated immune disorder, such as an IgE-mediated allergic disease, or reduce or alleviate an IgE-mediated immune response. IgE-mediated diseases include, but are not limited to, food allergies (e.g., allergies to nuts, shellfish, eggs, milk, beans), drug allergies (e.g., penicillin, other antibiotics), allergies to animal dander and dust mites, insect allergies (e.g., fire ants, bees), and hay fever and asthma allergens (e.g., plants, trees, grasses).

In some embodiments, the contacting step (in vivo or in vitro) results in suppression of IgE production by the cell.

In some embodiments, the cell is a human cell. In some embodiments, the cell is a mouse cell or other non-human, mammalian cell.

In some embodiments, the one or more compounds are contacted with the cell in vitro (e.g., in cell culture).

A tenth aspect of the present invention provides an inhibitory nucleic acid molecule that is capable of directly or indirectly interacting with the B cell $CB_2$ gene promoter region or transcript and thereby reducing expression of the B cell $CB_2$ gene. In some embodiments, the $CB_2$ gene promoter region targeted by the inhibitory nucleic acid molecule comprises at least one region selected from among the transcription start site (tss) for human exon 1, or at least a portion of the 3' or 5' untranslated region (UTR) for human exon 1 (FIG. 10; FIG. 14B). In some embodiments, the $CB_2$ gene promoter region targeted by the inhibitory nucleic acid molecule comprises at least one region selected from among the transcription start site (tss) for mouse exon 1a, mouse exon 1b, or mouse exon 2, or at least a portion of the 3' or 5' UTR for mouse exon 1a, mouse exon 1b, or mouse exon 2 (FIG. 9; FIG. 14A). In some embodiments, the inhibitory nucleic acid molecule comprises a nucleic acid sequence that is complementary with a target nucleic acid sequence within or overlapping with the B cell $CB_2$ gene promoter region. In some embodiments, the inhibitory nucleic acid molecule comprises a nucleic acid sequence that is complementary with a target nucleic acid sequence within or overlapping with at least one region selected from among the transcription start site (tss) for human exon 1, or at least a portion of the 3' or 5' untranslated region (UTR) for human exon 1 (FIG. 10; FIG. 14B). In some embodiments, the inhibitory nucleic acid molecule comprises a nucleic acid sequence that is complementary with a target nucleic acid sequence within or overlapping with at least one region selected from among the transcription start site (tss) for mouse exon 1a, mouse exon 1b, or mouse exon 2, or at least a portion of the 3' or 5' UTR for mouse exon 1a, mouse exon 1b, or mouse exon 2 (FIG. 9; FIG. 14A). In some embodiments, the inhibitory nucleic acid molecule is selected from among an interfering RNA (RNAi) molecule, an antisense oligonucleotide, a ribozyme, and a construct that causes targeted deletion of the $CB_2$ gene (e.g., induces a recombination event upon insertion into the B cell $CB_2$ gene promoter region). In some embodiments, the inhibitory nucleic acid molecules target a sequence within the sequence of the human $CB_2$ gene promoter region or transcript above and shown in FIG. 33. In some embodiments, the inhibitory nucleic acid molecule is an interfering RNA molecule comprising the nucleic acid sequence GGUGCUCUGAGUGGCACCC (SEQ ID NO: 7) or CACUCAACAGGUGCUCUGA (SEQ ID NO: 8), which target positions 12-30 and 3-21, respectively (FIG. 33). In some embodiments, the inhibitory nucleic acid molecule targets a sequence within the sequence of the mouse $CB_2$ gene promoter region or transcript shown above and in FIG. 31A (mouse Exon 2; SEQ ID NO: 9). In some embodiments, the inhibitory nucleic acid molecule is an interfering RNA molecule comprising at least one nucleic acid sequence shown above and in FIG. 31B (SEQ ID NOs: 10-39). In some embodiments, the inhibitory nucleic acid molecule targets a sequence within the sequence of the mouse $CB_2$ gene promoter region or transcript shown above and in FIG. 32A (mouse Exon 1b; SEQ ID NO: 40). In some embodiments, the inhibitory nucleic acid molecule is an interfering RNA molecule comprising at least one nucleic acid sequence shown above and in FIG. 32B (SEQ ID NOs: 41-83).

Another aspect of the invention concerns viral vectors and non-viral vectors carrying one or more inhibitory nucleic acid molecules of the invention or carrying a nucleic acid sequence encoding the inhibitory nucleic acid molecule, wherein the nucleic acid sequence encoding the inhibitory nucleic acid molecule is operably linked to a promoter that drives expression of the nucleic acid sequence encoding the inhibitory nucleic acid molecule (e.g., in the case of shRNA).

Another aspect of the invention is method for expressing a B cell $CB_2$ receptor polypeptide in a host cell, comprising administering a nucleic acid molecule to the cell, wherein the nucleic acid molecule comprises a nucleic acid sequence encoding the B cell $CB_2$ receptor polypeptide ($CB_2$ receptor coding sequence) and an operably linked B cell $CB_2$ gene promoter region, and wherein the nucleic acid sequence encoding the B cell $CB_2$ receptor polypeptide is expressed. The nucleic acid molecule can be administered within a viral vector or non-viral vector. In some embodiments, the nucleic acid molecule is administered to the cell in vitro. In some embodiments, the nucleic acid molecule is administered to the cell in vivo. The host cell may be a B-cell or a non-B-cell. In some embodiments, the nucleic acid molecule is administered to the cell in vivo, wherein expression of the nucleic acid sequence encoding the B cell $CB_2$ receptor polypeptide increases immunoglobulin E (IgE) production by the cell (e.g., a B cell). In some in vivo embodiments, the subject is a human or non-human mammal.

In some embodiments, the nucleic acid molecule is administered for treatment (therapy or prophylaxis) of a disorder in which increased IgE is of benefit. In some embodiments, the disorder is a pathogenic infection, such as a parasitic infection. In some embodiments, the infection is a helminthic infection. In some embodiments, the infection is a trypanosome infection.

BRIEF DESCRIPTION OF THE DRAWINGS

For a fuller understanding of the invention, reference should be made to the following detailed description, taken in connection with the accompanying drawings, in which:

FIGS. 1A-1C show results of computational analysis of the mouse Cnr2 (mCnr2) gene. FIG. 1A depicts the chromosome location of the mCnr2 (GenBank accession no. NC000070). FIG. 1B depicts the mCnr2 gene structure. Boxes represent exons, whereas white boxes are the untranslated region (UTR) and the dark grey shaded area is the protein coding region. ORF=open reading frame. Dotted lines are introns, which are spliced out to form mature mRNA. FIG. 1C shows mouse $CB_2$ mRNA transcripts. mCB$_2$ exon 1 transcripts are expressed in the murine leukemic cell line NFS107 (GenBank accession nos. X93168, NM009924), the spleen and thymus (GenBank accession nos. X86405, and AK037898), whereas mCB$_2$ exon 2 transcripts are expressed in liver and bone (GenBank accession nos. BC024052 and AK036658).

FIGS. 2A-2C show results of computational analysis of the human CNR2 (hCNR2) gene. FIG. 2A depicts the chromosome location of the hCNR2 (GenBank accession no. NC000001). FIG. 2B depicts the hCNR2 gene structure. Boxes represent exons, whereas white boxes are the untranslated region (UTR) and the dark grey shaded area is the protein coding region. ORF=open reading frame. Dotted lines are introns, which are spliced out to form mature mRNA. FIG. 1C shows hCB2 mRNA transcripts. hCB$_2$ mRNA transcripts are expressed in the human promyelocytic leukemic cell line HL60, human embryonic kidney cell line HEK293, brain, and leukocytes (GenBank accession nos. NM001841, AV430063, BC074767, and AM156854-6).

FIG. 3A shows RT-PCR products visualized on an agarose gel. FIG. 3B shows results of flow cytometry analysis of lymphocytes treated with CD19-PE, CD3-PerCP, NK-pan-FITC and F/480-APC anti-mouse mAbs (FITC and APC data not shown) to determine lymphocyte enrichment. The bar graph in FIG. 3C represents data of 5 independent B cell purification procedures (black bar). Grey bars are CD3+ cells.

FIG. 5A shows mouse 5' RACE products, 1° product length; exon 1b, 778-788 bp; exon 2, 614 bp; exon 1a, 543 bp. 2° size; exon 1b, 697-707 bp; exon 2, 533 bp; exon 1a, 459 bp. FIG. 5B shows the human 5' RACE product, 1°, 455 bp; 2°, 381 bp.

FIG. 6 shows an alignment of 5' RACE products, revealing the location of the TSSs (SEQ ID NOs: 84-109). To determine the TSS, the GCG SeqWeb PileUp program was used to align the 5' end of the RACE products with the CNR2 gene and the UPM (AACGCAGAGT) (SEQ ID NO: 110)-SII Oligo (ACGCGGG) sequences supplied with the RACE kit. TSSs are bold underlined and marked as +1. Shaded grey indicates the kit primers.

FIGS. 7A and 7B show the mouse and human putative core promoter elements near the TSSs. Once the TSS was located (+1) by pile-up analysis of the sequenced $CB_2$ transcripts with that of the Cnr2 gene and GenBank $CB_2$ mRNA clones, the CNR2 gene region spanning approximately −40 bp to +40 bp of the TSS was analyzed for core promoter elements which is blown-up here in order to view the sequences. FIG. 7A shows the putative core promoter of the mouse mCB2 exon 1a transcript (SEQ ID NO: 111-114). FIG. 7B shows the human hCNR2 gene putative core promoter SEQ ID NO: 115-117). INR Initiator (consensus sequence YYANWYY). DPE, Downstream promoter element (consensus sequence RGWCGTG).

FIG. 9 shows the mouse Cnr2 gene location of the TSSs and 5'UTR sequences identified by 5' RACE. Mouse $CB_2$ transcripts are labeled with their corresponding exon along with the number of nucleotides sequenced for each RACE product. The upward arrows represent the Cnr2 gene location of the TSSs (underlined nucleotide) relative to position 1 (bold underlined nucleotide) of the Genbank™ accession nos. NM009924 for exons 1a (SEQ ID NO: 118) & 1b (SEQ ID NO: 119) and BC024052 for exon 2 (SEQ ID NO: 120). Small black arrows mark the relative location of the GSPs. The 5'UTR exon sequences of the mCB$_2$ transcripts submitted to GenBank (accession nos. FJ357033-5).

FIG. 11A is an illustration of the strategy for primer mapping of the mouse mCB$_2$ TSSs. Forward primers A and D (black arrows) only amplify genomic DNA while forward primers B and E (grey arrows) amplify both genomic DNA and cDNA derived from CB$_2$ mRNA. The reverse primers C, F, and G (grey arrows) are shown. The blown out sequences (SEQ ID NOs: 122-123) illustrate where the forward primers bind in relation to the TSSs. The bold letters are the 3' and 5' end of the forward primers, and underlined nucleotides are the TSS. FIG. 11B shows results of gel electrophoresis of the mapped CB$_2$ transcripts, where in lane 1 contains cDNA derived from 1 μg of total RNA from mouse splenic B cells, lane 2 is genomic DNA extracted from B cells, and lane 3 contains the no template control. The bands are labeled with the primer pair (white letters) used for PCR amplification. The panels are labeled with the exon TSS tested.

FIG. 12B shows results of gel electrophoresis of the mapped hCB$_2$ transcript, where in lane 1 contains cDNA derived from 1 μg of total RNA from human PBMC B cells, lane 2 is genomic DNA extracted from B cells, and lane 3 contains the no template control. The primers used for each PCR are labeled in white above the bands.

FIGS. 14A and 14B show mouse and human putative core promoter elements near the TSSs. The gene region spanning approximately –40 bp to +40 bp of the TSSs was analyzed for core promoter elements. FIG. 14A shows the putative core promoters of the three mouse mCB$_2$ transcripts (SEQ ID NOs: 125-134). For exon 1b the numbers for the TSSs (+1) are color coordinated with their respective core promoter element. FIG. 14B shows the human hCNR2 gene putative core promoter (SEQ ID NOs: 135-136). INR, Initiator (consensus sequence YYANWYY). DPE, Downstream promoter element (consensus sequence RGWCGTG) BRE$^d$, TFIIB recognition element downstream the TATA-box (consensus sequence RTDKKKK).

FIGS. 15A and 15B show a ClustalW alignment of the mouse (SEQ ID NOs: 137-143 and SEQ ID NOs: 153-158) and human (SEQ ID NOs: 144-152 and SEQ ID NOs: 159-163) putative promoters. Conserved regions of mCnr2 and hCNR2 enabled prediction of the promoter region and cis-sequences (labeled and underlined). The 5' RACE TSSs (+1) are bold.

FIG. 16A shows results of PCR amplification of Cnr2 promoter regions TA-cloned into the TOPO-blue vector. FIG. 16B shows Hind III digest of TOPO-Cnr2 clones for subcloned into the pGL3-enhancer vector. FIG. 16C shows results of PCR amplification of Cnr2 clones in the pGL3-enhancer vector.

FIG. 17 shows the specific DNA nucleotide sequence of mouse promoter 1 for CB$_2$ gene in B cells [SEQ ID NO: 1]. The arrows indicate the location of transcription initiation by RNA Pol II. The major initiation site for basal transcription is indicated by the +1, which was determined by quantitative real time PCR. The trans-factors are labeled and indicated by black bold nucleotides. The underlined nucleotides indicate where the truncations were made for the experimental promoter constructs. The lower case nucleotides are the beginning of intron 1 with the first six having the splicing consensus sequence. The promoter is characterized by defined sequence of deoxyribonucleotides on chromosome 4 of the mouse genome stretching from genome position 135450780 to position 135451588. The DNA sequence for the complementary strand of this promoter is given in FIG. 17 and starts with deoxyribonucleotides 5'TGTCA at position 135450780 on chromosome 4 and extends to deoxyribonucleotides 5'AGCCT at position 135451588 on chromosome 4. This promoter region contains 4 validated transcription start sites (see arrows) and possibly a 5$^{th}$ site.

FIG. 18 shows the specific ribouncleotide sequence of unique fragment 1 for the mouse CB$_2$ gene in B cells [SEQ ID NO: 2]. Direct derivatives of promoter 1 and a second part of this invention are unique 5' ribonucleotide fragments termed unique gene transcript fragments 1, 2, 3, and 4 with defined ribonucleotide sequences (see FIGS. 18-21, respectively). The production of these unique fragments in B cells has been validated by us using the 5'RACE technique and nucleotide sequencing. Unique fragment 1 starts with AUCUG at position +1 in FIG. 17 and extends 151 nucleotides ending in UGACA at position +151 in FIG. 17 (see FIG. 18). Unique fragment 2 starts with ACAGA at position –261 in FIG. 17 and extends 412 nucleotides ending in UGACA at position +151 in FIG. 17 (see FIG. 19). Unique fragment 3 starts with ACAUG at position –268 in FIG. 17 and extends 419 nucleotides ending in UGACA at position +151 in FIG. 17 (see FIG. 20). Unique fragment 4 starts with ACAUA at position –280 in FIG. 17 and extends 431 nucleotides ending in UGACA at position +151 in FIG. 17 (see FIG. 21).

FIG. 19 shows the specific ribonucleotide sequence of unique fragment 2 of the mouse CB$_2$ gene in B cells [SEQ ID NO: 3].

FIG. 20 shows the specific ribonucleotide sequence of unique fragment 3 of the mouse CB$_2$ gene in B cells [SEQ ID NO: 4].

FIG. 21 shows the specific ribonucleotide sequence of unique fragment 4 of the mouse CB$_2$ gene in B cells [SEQ ID NO: 5].

FIG. 22A shows luciferase activity in exon 1 putative Cnr2 promoter pGL3-clones. FIG. 22B shows luciferase activity of exon 2 putative Cnr2 promoter pGL3-clones.

FIG. 24A shows the putative core promoters of the $mCB_2$ exon 1a and 1b transcripts in mouse (SEQ ID NOs: 164-171). As indicated above (FIG. 23, the luciferase reporter assay was used to analyze the relative promoter activity of each construct transfected into IL-4 (10 ng/ml) and anti-CD40 (500 ng/ml) activated primary B cells. The data are means±S.E.M expressed as a fold change to that of the pGL3-enhancer vector, shown in FIG. 24B. RLU, relative light units INR, Initiator (consensus sequence YYANWYY). DPE, Downstream promoter element (consensus sequence RGWCGTG) $BRE^d$, TFIIB recognition element downstream the TATA-box (consensus sequence RTDKKKK).

FIG. 29A shows results of gel electrophoresis of the 5' RACE products present in the B cell lines. FIG. 29B and 29C show results of RT-qPCR for $CB_2$ transcript expression in the B cell lines.

FIG. 30A shows the putative core promoter of the mCB2 exon 2 transcript (SEQ ID NOs:172-173). FIG. 30B shows the hCNR2 gene putative core promoter (SEQ ID NOs: 174-175). INR, Initiator (consensus sequence YYANWYY). DPE, Downstream promoter element (consensus sequence RGWCGTG) $BRE^d$, TFIIB recognition element downstream the TATA-box (consensus sequence RTDKKKK).

FIGS. 31A and 31B show nucleotides of Exon 2 of the mouse $CB_2$ promoter region (FIG. 31A), and thirty exemplified candidate interfering RNA sequences (siRNA, terminal UU nucleotides not shown) and target sequence positions (FIG. 31B) within the region shown in FIG. 31A. Candidate siRNAs 1-12 were identified using www.promega.com/siRNADesigner/program/using default parameters. Candidate siRNAs 14-38 were identified using bioinfo.clontech.com/rnaidesigner/sirnaSequenceDesign.do, using default parameters. Candidate siRNAs 19-30 were identified using jura.wi.mit.edu/bioc/siRNAext/home.php. The candidate siRNAs are listed in the order generated from each database based on predictive effectiveness of knockdown.

FIGS. 32A and 32B show nucleotides of Exon 1b of the mouse $CB_2$ promoter region (FIG. 32A), and forty-three exemplified candidate interfering RNA sequences (siRNA, terminal UU nucleotides not shown) and target sequence positions (FIG. 32B) within the region shown in FIG. 32A. Candidate siRNAs 1-24 were identified using www.promega.com/siRNADesigner/program/siRNA Target Designer using default parameters. Candidate siRNAs 25-34 were identified using bioinfo.clontech.com/rnaidesigner/sirnaSequenceDesign.do, using default parameters. Candidate siRNAs 35-43 were identified using Whitehead jura.wi.mit.edu/bioc/siRNAext/home.php. The candidate siRNAs are listed in the order generated from each database based on predictive effectiveness of knockdown.

FIG. 33 shows the first 75 nucleotides of the —35 region of the human $CB_2$ promoter region starting at position 1 (SEQ ID NO: 6) in FIG. 14B. FIG. 33 also shows two exemplified candidate interfering RNA sequences (siRNA, terminal UU nucleotides not shown) and target sequence positions within the region shown above. Candidate siRNA 1 (SEQ ID NO: 7) and siRNA 2 (SEQ ID NO: 8) were identified using www- .promega.com/siRNADesigner/program/ and bioinfo.clontech.com/rnaidesigner/sirnaSequenceDesign.do, respectively, with default parameters.

BRIEF DESCRIPTION OF THE SEQUENCES

Figure 3A:
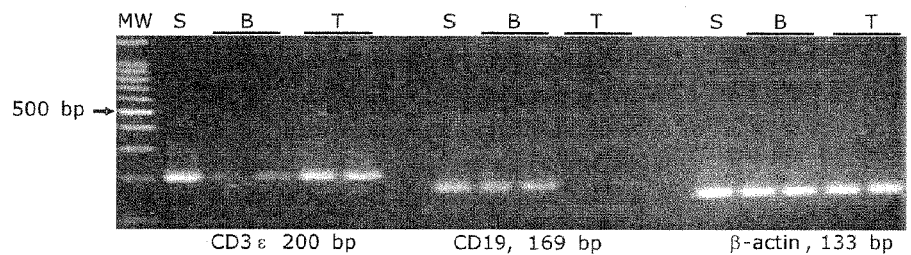
FIGS. 3A-3C show results of phenotypic analysis of mouse immune cell subtypes. Mouse B and T cells were isolated from splenocytes by affinity purification (EasySep®). RT-PCR was carried out for the presence of the CD3ε message in T cells and for B cell specific marker CD19. β-actin was used as loading control.

SEQ ID NO: 1 is the DNA sequence of mouse promoter 1 for $CB_2$ gene in B cells (shown in FIG. 17).

SEQ ID NO: 2 is the ribonucleotide sequence of unique fragment 1 of the mouse $CB_2$ gene in B cells (shown in FIG. 18, and shown starting at position +1 and ending at position +151 in FIG. 17).

SEQ ID NO: 3 is the ribonucleotide sequence of unique fragment 2 of the mouse $CB_2$ gene in B cells (shown in FIG. 19, and shown starting at position 261 and ending at position +151 in FIG. 17).

SEQ ID NO: 4 is the ribonucleotide sequence of unique fragment 3 of the mouse $CB_2$ gene in B cells (shown in FIG. 20, and shown starting at position –268 and ending at position +151 in FIG. 17).

SEQ ID NO: 5 is the ribonucleotide sequence of unique fragment 4 of the mouse $CB_2$ gene in B cells (shown in FIG. 21, and shown starting at position –280 and ending at position +151 in FIG. 17).

SEQ ID NO: 6 is the first 75 nucleotides of the –35 region of the human $CB_2$ promoter region starting at position 1 in FIG. 14B (also shown in FIG. 33).

SEQ ID NO: 7 is an exemplified candidate interfering RNA sequence (siRNA, terminal UU nucleotides not shown) (shown in FIG. 33).

SEQ ID NO: 8 is an exemplified candidate interfering RNA sequence (siRNA, terminal UU nucleotides not shown) (shown in FIG. 33).

SEQ ID NO: 9 is the nucleotide sequence of exon 2 of the mouse $CB_2$ gen promoter region (shown in FIG. 31A).

SEQ ID NOs: 10-39 are thirty exemplified candidate interfering RNA sequences targeting exon 2 of the mouse $CB_2$ promoter region. (shown in FIG. 31B).

SEQ ID NO: 40 is the nucleotide sequence of exon 1b of the mouse $CB_2$ promoter region (shown in FIG. 32A).

SEQ ID NOs: 41-83 are forty-three exemplified candidate interfering RNA sequences targeting exon 1b of the mouse $CB_2$ promoter region (shown in FIG. 32B).

SEQ ID NOs: 84-109 are aligned 5' RACE products of mouse exon 1a (SEQ ID NOs: 84-91), mouse exon 1b (SEQ ID NOs: 92-99), mouse exon 2 (SEQ ID NOs: 100-105), and human CNR2 gene (SEQ ID NOs: 106-109) (shown in FIG. 6).

SEQ ID NO: 110 is the UPM sequence supplied with RACE kit.

SEQ ID NOs: 111-114 are putative core promoter sequences of the mouse mCB2 exon 1a transcript (shown in FIG. 7A).

SEQ ID NOs: 115-117 are putative core promoter sequences of the human hCNR2 gene putative core promoter (shown in FIG. 7B).

SEQ ID NOs: 118-120 are sequences of mouse Cnr2 gene exons 1a, 1b, and 2, respectively (shown in FIG. 9).

Figure 10:
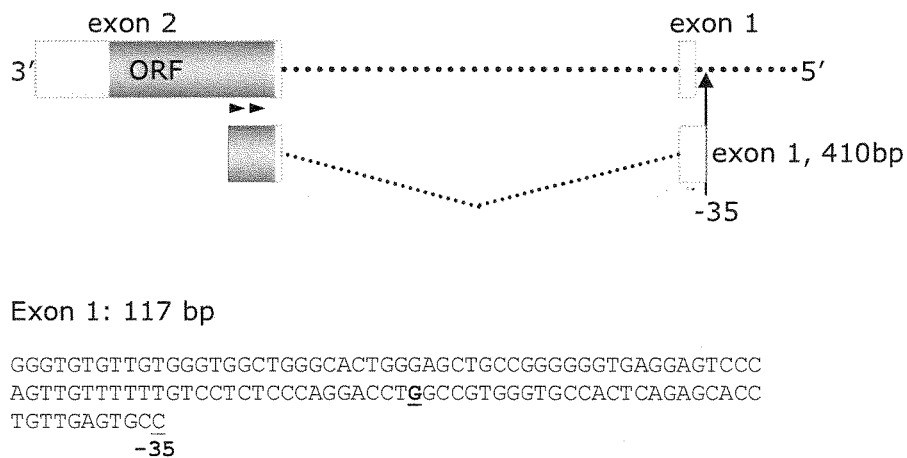
FIG. 10 shows human CB$_2$ 5'RACE transcripts having a single TSS and 5'UTR. The CNR2 gene location of the TSS (upward arrow). The number below the arrow represents the location of the TSS (underlined nucleotide) relative to position 1 (bold underlined nucleotide) of Genbank™ accession no. NM001841. Small black arrows mark the relative location of the GSPs. The CB$_2$ 5'UTR exon 1 sequence submitted to GenBank (accession no. FJ357036) (SEQ ID NO: 121).

SEQ ID NO: 121 is the human $CB_2$ 5'UTR exon 1 sequence, submitted to GenBank (Accession No. FJ357036) (shown in FIG. 10).

Figure 11A:
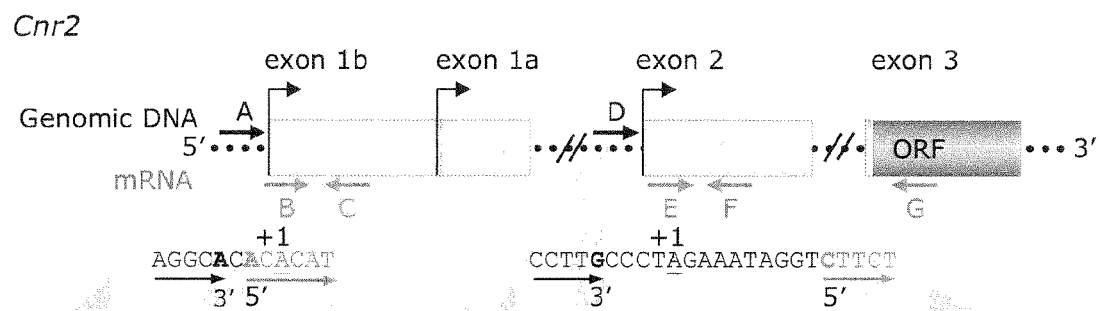
FIGS. 11A and 11B show primer mapping of the mouse mCB$_2$ TSSs.
Figure 11B:
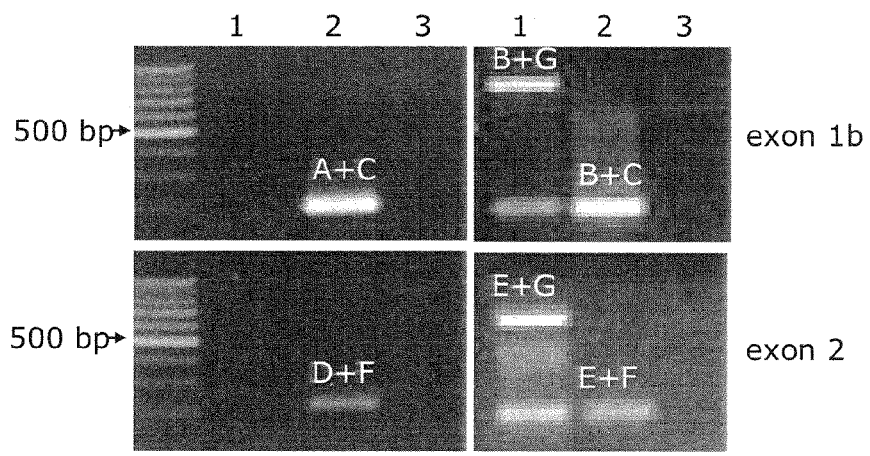

SEQ ID NOs: 122-123 are blown out sequences illustrating where the forward primers bind in relation to the TSSs (shown in FIG. 11a).

Figure 12A:
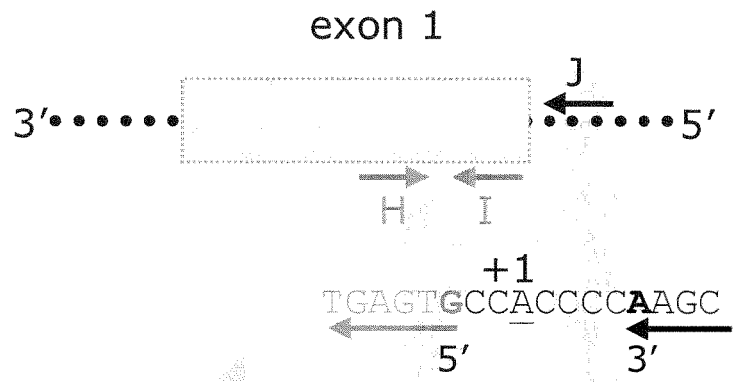
FIGS. 12A and 12B show primer mapping of hCB$_2$ TSS. In the primer map (FIG. 12A), forward primer J (black arrow) only amplifies genomic DNA and forward primer I (grey arrow) amplifies both genomic DNA and the cDNA derived from CB$_2$ mRNA. The reverse primer H (grey arrow) is shown. The blown out sequence (SEQ ID NO: 124) illustrates where the forward primers bind in relation to the TSSs. The bold letters are the 3' and 5' end of the forward primers, and the underlined nucleotide is the TSS.

SEQ ID NO: 124 is the blown out sequence illustrating where the forward primers bind in relation to the TSSs (shown in FIG. 12a).

SEQ ID NOs: 125-134 are putative core promoter sequences of the three mouse $mCB_2$ transcripts (shown in FIG. 14A).

SEQ ID NOs: 135-136 are the human hCNR2 gene putative core promoter sequence (FIG. 14B).

SEQ ID NOs: 137-143 are aligned mouse mCnr2 putative promoter sequences (shown in FIG. 15A).

SEQ ID NOs: 144-152 are aligned human hCNR2 putative promoter sequences (shown in FIG. 15A).

SEQ ID NOs: 153-158 are aligned mouse mCnr2 putative promoter sequences (shown in FIG. 15B).

SEQ ID NOs: 159-163 are aligned human hCNR2 putative promoter sequences (shown in FIG. 15B).

Figure 24A:
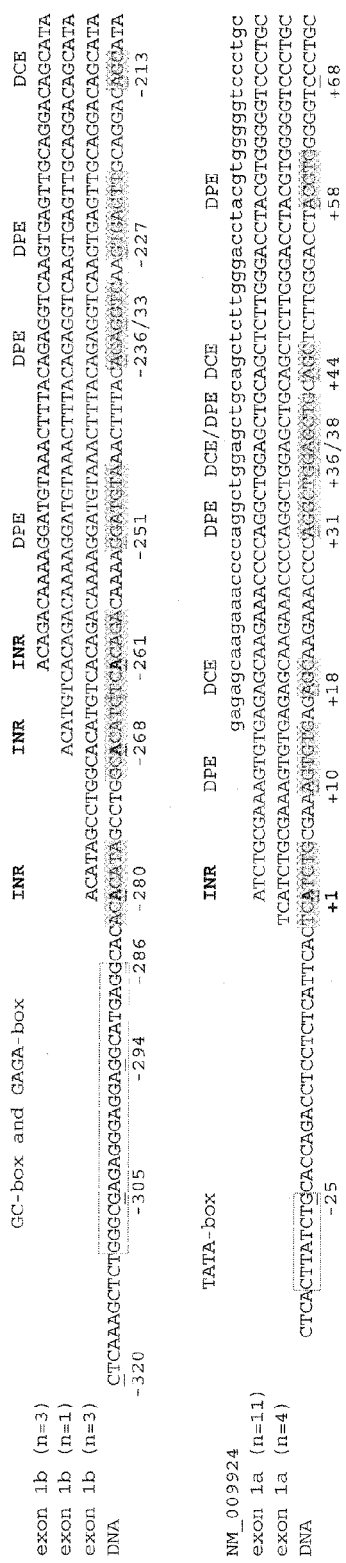
FIGS. 24A and 24B show promoter activity in the region containing the mouse exon 1a and 1b TSSs. A PileUp analysis was performed using the GCG SeqWeb software of the sequenced $CB_2$ transcripts with that of the Cnr2 gene and GenBank $CB_2$ mRNA clones to determine the location of the 5' RACE TSS (+1). Once located, the Cnr2 gene region spanning approximately −359 bp to +205 bp of the exon 1a TSS (+1) was analyzed for promoter activity.
Figure 24B:
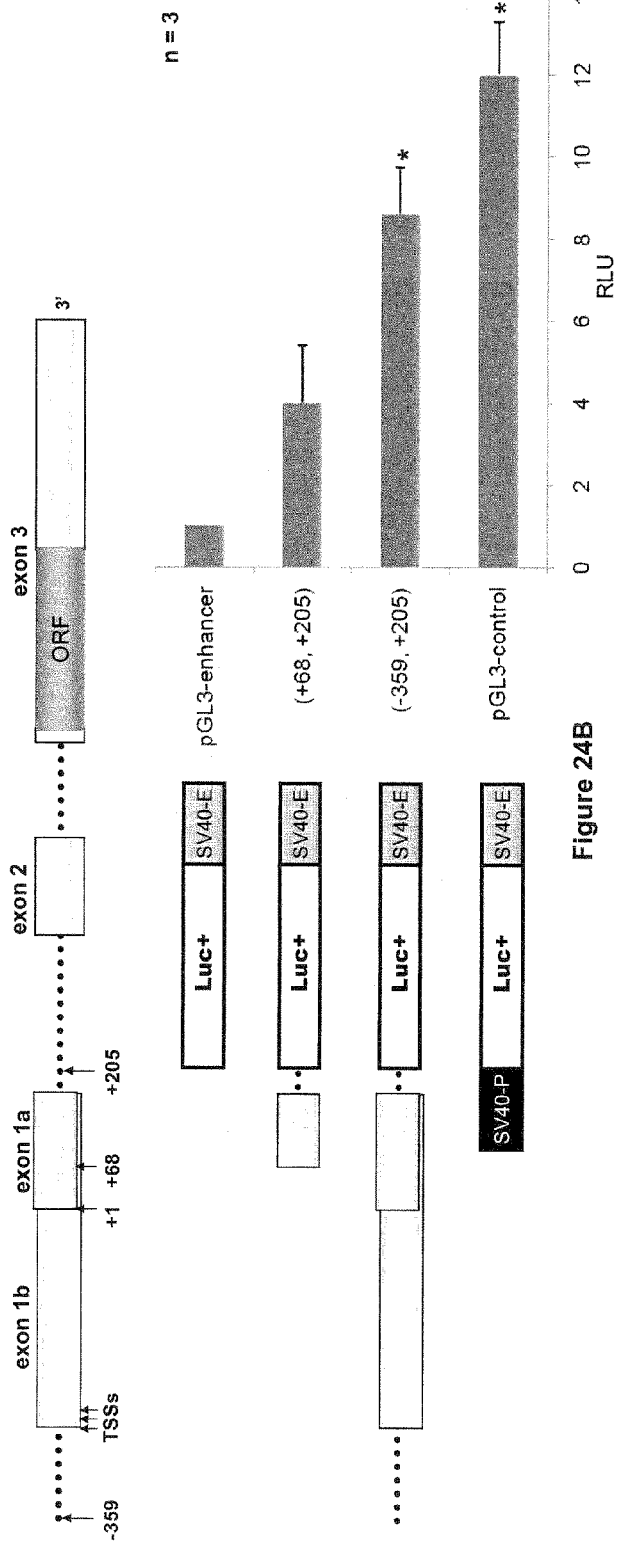

SEQ ID NOs: 164-171 are putative core promoter sequences of the $mCB_2$ exon 1a and 1b transcripts in mouse (shown in FIG. 24A).

Figure 30A:
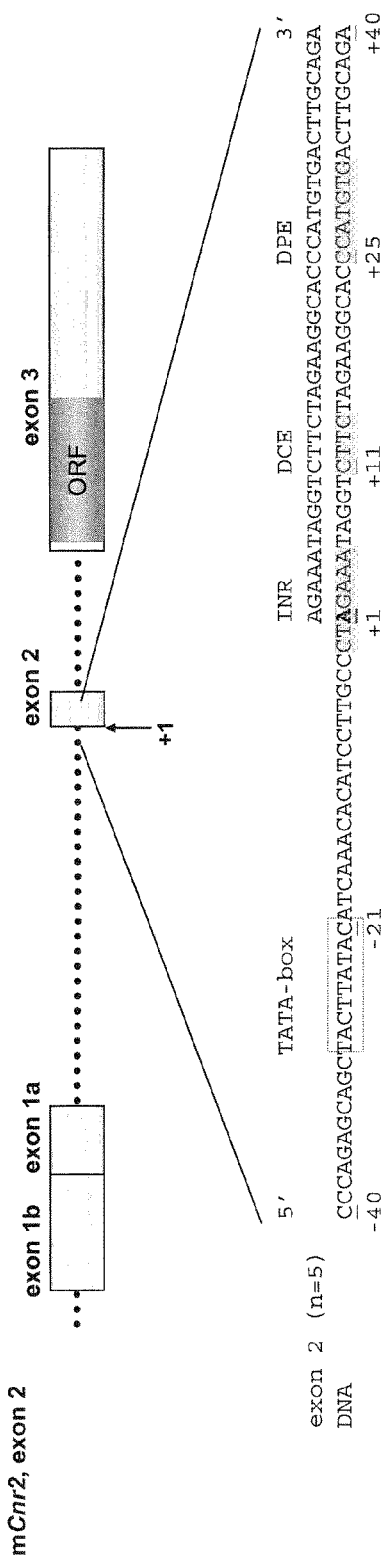
FIGS. 30A and 30B show putative core promoter elements near the TSSs. Once the location of the 5' RACE TSS (+1) was identified by PileUp analysis (GCG SeqWeb software), the gene region spanning approximately −40 bp to +40 bp of the TSSs was analyzed for core promoter elements, which is blown-up here in order to view the sequences.

SEQ ID NOs: 172-173 are putative core promoter sequences of the mCB2 exon 2 transcript (shown in FIG. 30A).

Figure 30B:
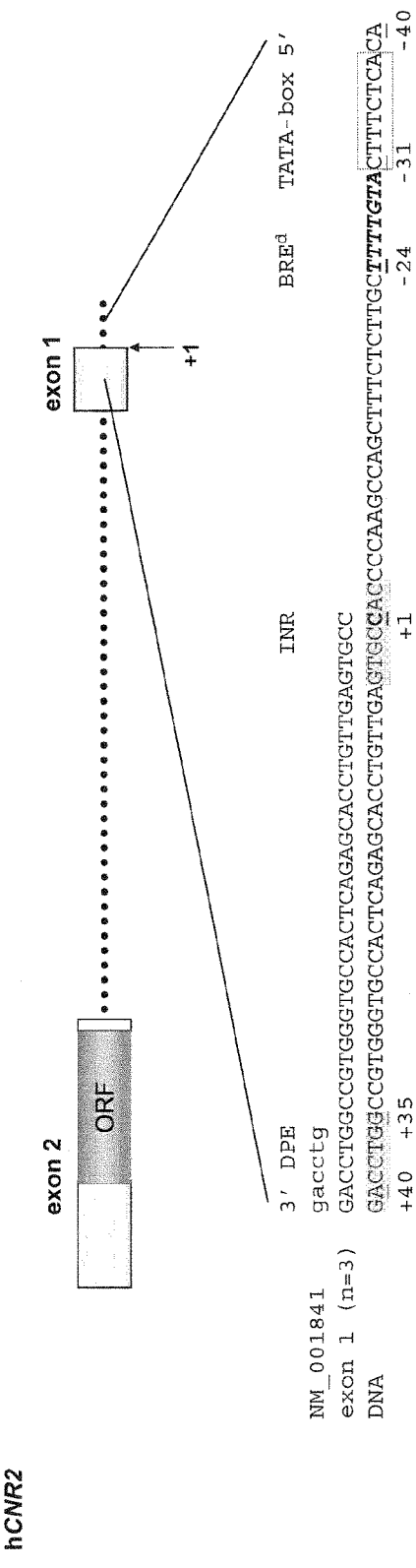

SEQ ID NOs: 174-175 are hCNR2 gene putative core promoter sequences (shown in FIG. 30B).

SEQ ID NOs: 176-179—SMART 5' RACE primers used to identify the TSS (listed in Table 1).

SEQ ID NOs: 180-190 are primers used for mapping the TSSs (listed in Table 2).

SEQ ID NOs: 191-205 are primers and Taqman probes used in this study (listed in Table 3).

SEQ ID NOs: 206-221 are promoter clones and PCR primers (listed in Table 4).

DETAILED DISCLOSURE OF THE INVENTION

Cannabinoids and cannabinoid receptors have been shown to play important roles in immune regulation particularly as modulators of anti-inflammatory cytokines and antibody production. The predominant cannabinoid receptor involved in this immune regulation is cannabinoid receptor 2 ($CB_2$), which is robustly expressed in B cells. Utilizing a combination of bioinformatics, 5' RACE, real time RT-qPCR, and reporter assays, we showed that human B cells from peripheral blood mononuclear cells (PBMC) expressed one $CB_2$ transcript while mouse B cells from spleen express three $CB_2$ transcripts. Alignment of the sequenced B cell RACE products to either the mouse or human genome, along with the GenBank mRNA sequences, revealed that the transcripts isolated in this study contained previously unidentified transcriptional start sites (TSSs). In addition, expression construct testing of the genomic region containing the TSSs of the mouse CB, exon 1 and 2 transcripts showed a significant increase of promoter activity. Bioinformatics analysis for cis-sequences in the promoter regions identified DNA binding sites for NF-kB, STAT6, and Elk1 transcription factors activated by LPS, IL-4 and anti-CD40. Regarding variations in $CB_2$ transcript expression among the immune cell subtypes, RACE analysis showed that the exon 1b transcript is seen in B cells but not in T cells, dendritic cells or macrophages. Furthermore, RT-qPCR showed variations in transcript expression during B cell development as well as in resting versus LPS or IL-4/anti-CD40 stimulated B cells. The exon 1a transcript was predominant in pre-, immature and resting B cells whereas the exon 1b and 2 transcripts were enhanced in mature and activated B cells. These data showed for the first time that human B cells use one TSS for $CB_2$ expression while mouse B cells use multiple TSSs for the expression of three $CB_2$ transcripts, in which the expression of the individual transcript is related to immune cell type and/or cell activation state. Additionally, this is the first report in mouse B cells defining TSSs that are in genomic areas with promoter activity thus suggesting the location of two promoter regions. Defining the TSSs, promoters and $CB_2$ transcript expression profile during various stages of B cell activation provide opportunities for therapeutic methods useful in regulating the expression of this receptor in B cells.

The invention provides a defined sequence of deoxyribonucleotides on chromosome 4 of the mouse genome stretching from genome position 135450780 to position 135451588. The DNA sequence for the complementary strand of this promoter is given in FIG. 17 and starts with deoxyribonucleotides 5'TGTCA at position 135450780 on chromosome 4 and extends to deoxyribonucleotides 5'AGCCT at position 135451588 on chromosome 4. This promoter region contains 4 transcription start sites (see arrows), which have been validated by the present inventors, and possibly a $5^{th}$ site.

Direct derivatives of promoter 1 and a second part of this invention are unique 5' ribonucleotide fragments termed unique gene transcript fragments 1, 2, 3, and 4 with defined ribonucleotide sequences (see FIGS. 18-21). The production of these unique fragments in B cells has been validated by the inventors using the 5'RACE technique and nucleotide sequencing. Unique fragment 1 starts with AUCUG at position +1 in FIG. 17 and extends 151 nucleotides ending in UGACA at position +151 in FIG. 17 (see FIG. 18). Unique fragment 2 starts with ACAGA at position −261 in FIG. 17 and extends 412 nucleotides ending in UGACA at position +151 in FIG. 17 (see FIG. 18). Unique fragment 3 starts with ACAUG at position −268 in FIG. 17 and extends 419 nucleotides ending in UGACA at position +151 in FIG. 17 (see FIG. 19). Unique fragment 4 starts with ACAUA at position −280 in FIG. 17 and extends 431 nucleotides ending in UGACA at position +151 in FIG. 17 (see FIG. 21).

Figure 13A:
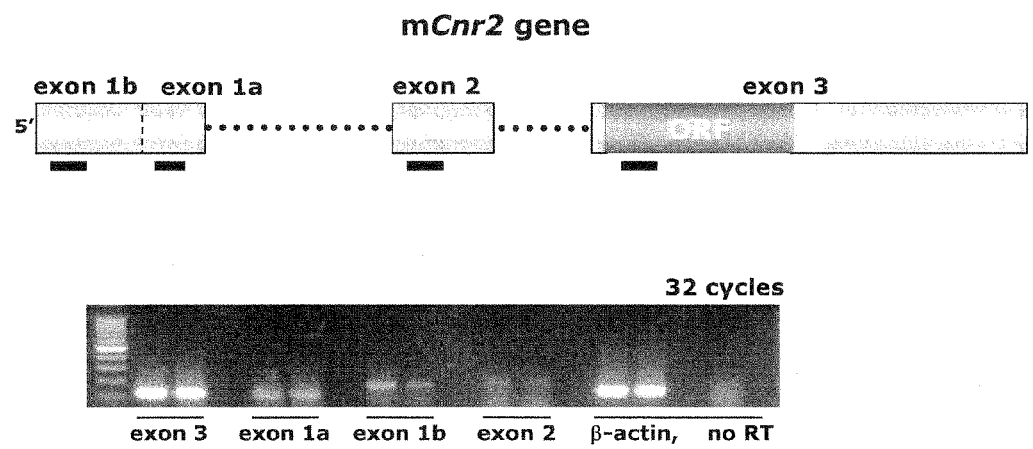
FIGS. 13A and 13B show results of quantitative real time RT-PCR (RT-qPCR) for mouse mCB$_2$ mRNA expression in resting splenic B cells. Semi-quantitative RT-PCR of the mCB$_2$ transcripts was carried out using exon specific primers and 2 separate mouse B cell samples. The samples were collected after 32 cycles of amplification and run on a 2% agarose gel visualized with ethidium bromide, shown in FIG. 13A. Using taqman probes; RT-qPCR was performed to determine the major CB$_2$ transcript utilized in mouse B cells at basal transcription. Results were normalized with β-actin and expressed as a ratio of CB$_2$ transcript/β-actin, shown in FIG. 13B Data are means±S.E.M. of five independent experiments.
Figure 13B:
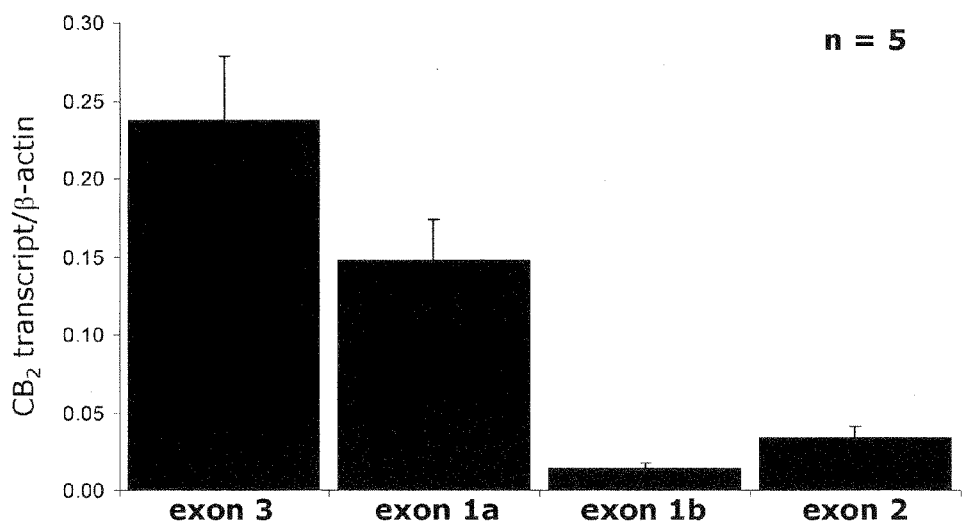

The gene promoter activity of a chromosome segment can be determined by inserting the segment of putative promoter into a so-called Reporter Vector and then inserting the vector into a relevant cell type. 17 different DNA fragments of the putative promoter segment of the $CB_2$ gene were isolated and inserted these into the pGL3 Luciferase Promoter Vector (Promega Corporation, Madison, Wis. 73711). These different Vectors were then inserted (transfected) into the 18.81 mouse B cell line and tested for gene promoter activity by assaying the activity of the read-out gene product, luciferase (FIG. 13B). The activity of the luciferase is expressed in relative light units (RLUs) normalized to the control vector construct containing only a gene enhancer sequence (see Enhan bar in FIG. 13). From FIG. 13A-B, it can be seen that the highest gene promoter activity is associated with fragment −359 to +205. Lengthening or shortening this fragment lessens the promoter activity; however, fragment −604 to +205 still has very good promoter activity and is therefore identified as the sequence encompassing the gene promoter.

The focus of this research was to determine the Cnr2 gene transcription start site (TSS) and associated promoter and cis-sequences involved in $CB_2$ in RNA expression in B cells as well as investigate transcript usage in resting and activated cells. Previous studies suggest a role of $CB_2$ in the immune regulation of B cells by demonstrating involvement in B cell differentiation, migration, proliferation, and immunoglobulin class switching to IgE. A preliminary computational analysis of the murine Cnr2 gene and GenBank $CB_2$ mRNA clones revealed that two alternate transcripts containing different 5'UTR first exons (1 and 2) were reported. Three clones from immune tissues contained the exon 1 5'UTR, whereas clones originating from bone and liver contained the exon 2 5'UTR. This analysis indicated that more than one transcript is produced from the Cnr2 gene, and that the transcripts may be related to cell type or function. From this, the present inventors hypothesized that the Cnr2 gene encodes multiple transcripts in B cells and other immune cells, which are varied following changes in cell function. In order to test this hypothesis, the present inventors propose the following aims:

Aim 1. To Determine the Extent of $CB_2$ Transcript Expression and TSSs in B cells (Examples 1-4)

Evidence in the genomic databases suggested the occurrence of multiple $CB_2$ transcripts utilizing different first exons in various mouse tissues, as mentioned above. It is well known that the TSS is located either at the beginning of the first exon or upstream from it. Since 2 first exons (exon 1 and 2) have been reported, B cells possibly express multiple TSSs and $CB_2$ transcripts employing different first exons. Therefore, the inventors explored this possibility in resting B cells. To accomplish this aim, the inventors used the Switching Mechanism At 5' end of RNA Transcript—Rapid Amplification of cDNA Ends (SMART 5' RACE) to identify the number and location of the $CB_2$ TSSs in splenic and PBMC B cells.

Aim 2. To Characterize the Cnr2 Gene Promoter in B Cells (Examples 5-8)

It has been well established that accurate identification of the TSS leads to the location of the core promoter, which is usually −40 bp upstream to +40 bp downstream of the TSS. The basic elements that comprise the core promoter are the TATA-box, INR (Initiator), DPE (downstream promoter element), and BRE (TFIIB recognition elements) (Sandelin, A. et al., *Nature reviews,* 2007, 8:424-436). Identifying the promoter will lead to a better understanding of how the Cnr2 gene is regulated in B cells, which in turn will lead to the elucidation of the mechanisms involved in the immunobiology of $CB_2$ and B cells. The inventors started with a bioinformatics analysis using web based analytical tools, such as Genomatix, to locate the putative promoter regions of the Cnr2 gene. These were then cloned into luciferase reporter gene expression vectors and transfected into purified splenic B cells to test for promoter activity. Truncations of the clones were performed to identify core promoter and cis-regulatory sequences.

Aim 3. To Determine $CB_2$ Transcript Usage in Activated B Cells as Well as Other Immune Cell Subtypes (Examples 9-11)

Since $CB_2$ is abundant in B cells and implicated in the involvement of various B cell functions, an understanding of transcript usage under varying conditions of B cell activation will be of value in designing future studies to regulate $CB_2$ expression. The GenBank data showed that multiple $CB_2$ transcripts exist; therefore, the inventors surmised that some of these could be unique to B cells and the various associated 5' UTR sequences could provide useful targets for selectively suppressing or enhancing receptor expression in B cells. In this aim, the present inventors compared $CB_2$ transcript usage in resting and stimulated B cells. The literature shows that stimulation of B cells with anti-CD40 and/or IL-4, through STAT6 activation, increases $CB_2$ expression (Carayon, P. et al., *Blood,* 1998, 92:3605-3615; Lee, S. F. et al., *Eur J Pharmacol,* 2001, 423:235-241; Agudelo, M. et al., *Journal of Neuroimmune Pharmacology,* 2008, 3:35-42; Schroder, A. J. et al., *J Immunol,* 2002, 168:996-1000) whereas, LPS stimulation suppresses expression (Lee, S. F. et al., *Advances in Experimental Medicine and Biology,* 2001, 493:223-228). Therefore, to examine $CB_2$ transcript usage, the inventors stimulated purified B cells with stimuli reported to increase $CB_2$ expression, such as IL4 that activates STAT6, anti-CD40 that increases NFκB, and LPS, a known B cell mitogen, that binds to TLR4 and activates NFκB and/or IRF3. However, LPS has been shown to decrease $CB_2$ message; therefore, results from these experiments may uncover possible repressor elements. To perform these experiments, B cells were isolated and cultured alone or with the various stimuli, and analyzed by RT-qPCR at various time points following B cell stimulation.

Since the inventors wanted to know if any of the $CB_2$ transcripts are unique in B cells, other immune cell subtypes were analyzed, such as T cells, dendritic cells and macrophages for the presence of $CB_2$ transcript variants.

The present inventors have characterized for the first time multiple TSSs that define alternative $CB_2$ transcripts in mouse splenic B cells as well as a single TSS and transcript in human PBMC B cells. The inventors were able to confirm by RT-PCR primer mapping, the relative location of the TSS for mouse exons 1b and 2, as well as the human exon 1. These experimentally defined TSSs directed further in silico analysis and showed that these regions contain consensus sequences for multiple elements such as TATA-box, INR and DPE. These elements were found at the expected distances from the TSSs and by reporter assay experiments these segments contained significant promoter activity inferring that we correctly identified several of the TSSs in mouse B cells as well as identify the location of two promoters. In addition, we identified $CB_2$ transcript usage in resting B cells as well as other immune cell subtypes, in which the exon 1b transcript appears to be unique to B cells and therefore may serve as a therapeutic target in B cells. In addition, $CB_2$ transcript expression was different in the mouse B cell lines representing various maturation stages. Furthermore, we identified $CB_2$ transcript expression in LPS and IL-4/anti-CD40 activated B cells, in which the exon 1b and exon 2 variants appear to be important.

The stimuli used in this study are known inducers of class switch recombination (CSR) and previous work done in the inventors' lab has suggested a role for $CB_2$ receptor activation in enhancing IL-4/anti-CD40 CSR from IgM to IgE; therefore, it is possible from the work here, that exon 1b transcripts are unique to B cells and therefore provide a gene target for suppressing $CB_2$ expression in only B cells and not other immune cell subtypes. The identification of the $CB_2$ transcripts expressed during these conditions provides gene targets for the therapeutic administration of nucleic acid-based effecter molecules (e.g., by RNA interference (RNAi), antisense oligonucleotides, ribozymes) in suppressing $CB_2$ and IgE production in allergic diseases, and can guide future studies in regulating this receptor at the gene level.

The compound used to reduce $CB_2$ gene expression in vitro or in vivo can be virtually any substance and can encompass numerous chemical classes, including organic compounds or inorganic compounds. Preferably, an effective amount of the compound is administered to the cells with a carrier (preferably, a pharmaceutically acceptable carrier). The compound may be a substance such as genetic material, protein, lipid, carbohydrate, small molecules, a combination of any of two or more of foregoing, or other compositions. The compound may be naturally occurring or synthetic, and may be a single substance or a mixture. The compound can be obtained from a wide variety of sources including libraries of compounds. The compound can be or include, for example, a polypeptide, peptidomimetic, amino acid(s), amino acid analog(s), polynucleotide(s), polynucleotide analog(s), nucleotide(s), nucleotide analog(s), or other small molecule(s). In some embodiments, the compound is an inhibitory nucleic acid molecule such as an RNA interference molecule (e.g., siRNA or shRNA), antisense oligonucleotide, ribozyme, or other nucleic acid that targets a B cell $CB_2$ promoter region for reducing gene expression of a cell.

In one embodiment, the compound is an interfering RNA specific for a target sequence within or overlapping with a B cell $CB_2$ promoter region. RNAi molecules can be selected using an siRNA Target Finder program (AMBION) and in accordance with published guidelines (Tuschl T., *Nature Biotechnol.*, 2002, 20:446448). As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to reduce (e.g., to lessen (knockdown) or essentially eliminate ("silence")) the expression of target genes.

As used herein, the term "small interfering RNA" ("siRNA") (also referred to in the art as "short interfering RNAs") refers to an RNA (or RNA analog) that is capable of directing or mediating RNA interference. In one embodiment, the siRNA is between about 10-50 nucleotides (or nucleotide analogs). Optionally, a polynucleotide (e.g., DNA) encoding the siRNA may be administered to cells in vitro or in vivo, such as in a vector, wherein the DNA is transcribed.

As used herein, a siRNA having a "sequence sufficiently complementary to a target mRNA sequence to direct target-specific RNA interference (RNAi)" means that the siRNA has a sequence sufficient to trigger the destruction of the target mRNA of the $CB_2$ promoter region by the RNAi machinery or process. "mRNA" or "messenger RNA" or "transcript" is single-stranded RNA that specifies the amino acid sequence of one or more polypeptides. This information is translated during protein synthesis when ribosomes bind to the mRNA.

The scientific literature is replete with reports of endogenous and exogenous gene expression silencing using siRNA, highlighting their therapeutic potential (Gupta, S. et al. *PNAS*, 2004, 101:1927-1932; Takaku, H. *Antivir Chem. Chemother*, 2004, 15:57-65; Pardridge, W. M. *Expert Opin. Biol. Ther.*, 2004, 4:1103-1113; Zheng, B. J. *Antivir. Ther.*, 2004, 9:365-374; Shen, W. G. *Chin. Med. J. (Engl)*, 2004, 117:1084-1091; Fuchs, U. et al. *Curr. Mol. Med.*, 2004, 4:507-517; Wadhwa, R. et al. *Mutat. Res.*, 2004, 567:71-84; Ichim, T. E. et al. *Am. J. Transplant*, 2004, 4:1227-1236; Jana, S. et al. *Appl. Microbiol. Biotechnol.*, 2004, 65:649-657; Ryther, R. C. et al. *Gene Ther.*, 2005, 12:5-11; Chae, S-S. et al., *J. Clin. Invest.*, 2004, 114:1082-1089; Fougerolles, A. et al., *Methods Enzymol.*, 2005, 392:278-296), each of which is incorporated herein by reference in its entirety. Therapeutic silencing of endogenous genes by systemic administration of siRNAs has been described in the literature (Kim B. et al., *American Journal of Pathology*, 2004, 165:2177-2185; Soutschek J. et al., *Nature*, 2004, 432:173-178; Pardridge W. M., *Expert Opin. Biol. Ther.*, 2004, July, 4(7): 1103-1113), each of which is incorporated herein by reference in its entirety.

The methods may include further steps. In some embodiments, a subject with an allergic disease is identified or a subject at risk for the disease is identified. A subject may be someone who has not been diagnosed with the disease or condition or someone diagnosed with disease, including someone previously treated for the disease. Alternatively, the individual may not have been diagnosed with the disease but suspected of having the disease based either on patient history or family history, or the exhibition or observation of characteristic symptoms or genetic profile, for example.

The inhibitory nucleic acid molecules used in the methods, vectors, and compositions of the present invention are typically in an isolated state. According to the present invention, an isolated nucleic acid molecule or nucleic acid sequence, is a nucleic acid molecule or sequence that has been synthesized or removed from its natural milieu. As such, "isolated" does not necessarily reflect the extent to which the nucleic acid molecule has been purified. An isolated nucleic acid molecule or sequence useful as an inhibitory molecule in the present composition can include DNA, RNA, or any derivatives of either DNA or RNA. The nucleic acids can be modified or unmodified. An isolated nucleic acid molecule or sequence can be double stranded (i.e., containing both a coding strand and a complementary strand) or single stranded.

A nucleic acid molecule can be isolated from a natural source, or it can be produced using recombinant DNA technology (e.g., polymerase chain reaction (PCR) amplification, cloning) or chemical synthesis. Nucleic acid molecules can be generated or modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules, and combinations thereof.

Although the phrase "nucleic acid molecule" primarily refers to the physical nucleic acid molecule and the phrase "nucleic acid sequence" primarily refers to the sequence of nucleotides on the nucleic acid molecule, the two phrases are used interchangeably herein. As used herein, a "coding" nucleic acid sequence refers to a nucleic acid sequence that encodes at least a portion of a peptide or protein (e.g., a portion of an open reading frame), and can more particularly refer to a nucleic acid sequence encoding a peptide or protein which, when operatively linked to a transcription control sequence (e.g., a promoter sequence), can express the peptide or protein.

Modified nucleic acid sequences will be understood to mean any nucleotide sequence obtained by mutagenesis according to techniques well known to persons skilled in the art, and exhibiting modifications in relation to the normal sequences. For example, mutations in the regulatory and/or promoter sequences for the expression of a polypeptide that result in a modification of the level of expression of a polypeptide according to one example provide for a "modified nucleotide sequence". Likewise, substitutions, deletions, or additions of nucleic acids to the polynucleotides in one example, provide for "homologous" or "modified" nucleotide sequences. In various embodiments, "homologous" or "modified" nucleic acid sequences have substantially the same biological or serological activity as the native (naturally occurring) peptide. A "homologous" or "modified" nucleotide sequence will also be understood to mean a splice variant of the polynucleotides of the instant invention or any nucleotide sequence encoding a "modified polypeptide" as defined below.

A homologous nucleotide sequence, for the purposes of the present invention, encompasses a nucleotide sequence having a percentage identity with the bases of the nucleotide sequences of between at least (or at least about) 20.00% to 99.99% (inclusive). The aforementioned range of percent identity is to be taken as including, and providing written description and support for, any fractional percentage, in intervals of 0.01%, between 20.00% and 99.99%. These percentages are purely statistical and differences between two nucleic acid sequences can be distributed randomly and over the entire sequence length.

In various embodiments, homologous sequences exhibiting a percentage identity with the bases of the nucleotide sequences of the present invention can have 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent identity with the polynucleotide sequences of the instant invention. Homologous nucleotide and amino acid sequences include mammalian homologs of the human sequences.

Both protein and nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman *Proc. Natl. Acad. Sci. USA*, 1988, 85(8):2444-2448; Altschul et al. *J. Mol. Biol.*, 1990, 215(3): 403-410; Thompson et al. *Nucleic Acids Res.*, 1994, 22(2): 4673-4680; Higgins et al. *Methods Enzymol.*, 1996, 266:383-402; Altschul et al. *J. Mol. Biol.*, 1990, 215(3):403-410; Altschul et al. *Nature Genetics*, 1993, 3:266-272).

Identity and similarity of related nucleic acid molecules and polypeptides can be readily calculated by known methods. Such methods include, but are not limited to, those described in Computational Molecular Biology, Lesk, A. M., ed., Oxford University Press, New York, 1988; York (1988); Biocomputing: Informatics and Genome Projects, Smith, D. W., ed., Academic Press, New York, 1993; York (1993); Computer Analysis of Sequence Data, Part 1, Griffin, A. M., and Griffin, H. G., eds., Humana Press, New Jersey, 1994; Jersey (1994); Sequence Analysis in Molecular Biology, von Heinje, G., Academic Press, 1987; Press (1987); Sequence Analysis Primer, Gribskov, M. and Devereux, J., eds., M. Stockton Press, New York, 1991; York (1991); and Carillo et al., SIAM J. Applied Math., 48:1073 (1988).

The methods also include the contacting one or more compounds to cells genetically modified to have a $CB_2$ promoter region disclosed herein. The term "genetic modification" as used herein refers to the stable or transient alteration of the genotype of a cell of the subject invention by intentional introduction of exogenous nucleic acids by any means known in the art (including for example, direct transmission of a polynucleotide sequence from a cell or virus particle, transmission of infective virus particles, and transmission by any known polynucleotide-bearing substance) resulting in a permanent or temporary alteration of genotype. The nucleic acids may be synthetic, or naturally derived, and may contain genes, portions of genes, or other useful polynucleotides in addition to the $CB_2$ promoter, such as the $CB_2$ receptor gene. A translation initiation codon can be inserted as necessary, making methionine the first amino acid in the sequence. The genetic modification may confer the ability to produce the $CB_2$ receptor, wherein the cell did not previously have the capability, or the modification may increase the amount of $CB_2$ endogenously produced by the cell, e.g., through increased expression.

Exogenous nucleic acids and/or vectors can be introduced into a cell by viral vectors (retrovirus, modified herpes virus, herpes virus, adenovirus, adeno-associated virus, lentivirus, and the like) or direct DNA transfection (lipofection, chitosan-nanoparticle mediated transfection, calcium phosphate transfection, DEAE-dextran, electroporation, and the like), microinjection, cationic lipid-mediated transfection, transduction, scrape loading, ballistic introduction and infection (see, for example, Sambrook et al. [1989] *Molecular Clon-* ing: *A Laboratory Manual*, 2<sup>nd</sup> Ed., Cold Spring Harbor Laboratory Press, Cold Spring Harbor, N.Y.).

In some embodiments, the inhibitory nucleic acid molecule is operably linked to a promoter sequence that permits expression of a nucleotide sequence within the nucleic acid molecule in a desired tissue within a subject. The promoters can be inducible, tissue-specific, or event-specific, as necessary. Inhibitory nucleic acid molecules can be administered locally at a desired site or systemically.

The cell that has been genetically modified to encode the $CB_2$ receptor may be chosen from eukaryotic or prokaryotic systems, for example, bacterial cells (Gram negative or Gram positive), yeast cells, animal cells, plant cells, and/or insect cells using baculovirus vectors, for example. In some embodiments, the genetically modified cell is a human or non-human mammal cells.

According to some embodiments of the methods of the invention, one or more compounds (e.g., inhibitory nucleic acid molecules) may be administered to a subject in order to alleviate (e.g., reduce or eliminate) a variety of symptoms associated with an allergic disease, i.e., treatment of the disease. "Treatment" is intended to include prophylactic intervention to prevent or reduce an undesirable immune response (e.g., allergic response) and onset of the symptoms associated with an allergic disease, as well as treatment of existing allergic diseases. The nucleic acid sequences and pharmaceutical compositions may be co-administered (concurrently or consecutively) to a subject with other therapeutic agents useful for treating allergic diseases.

Various viral or non-viral vectors may be used to deliver inhibitory nucleic acids to cells in vitro or in vivo. Tissue-specific promoters or event-specific promoters may be utilized with nucleic acid molecules to further optimize and localize expression at target sites, such as within diseased tissues (e.g., respiratory cells).

Many techniques for delivery of drugs and proteins are available in the art to reduce the effects of enzymatic degradation, to facilitate cell uptake, and to reduce any potential toxicity to normal (undiseased) cells, etc. Such methods and reagents can be utilized for delivery of compounds to cells in vitro or in vivo. For example, peptides known as "cell penetrating peptides" (CPP) or "protein transduction domains" (PTD) have an ability to cross the cell membrane and enter the cell. PTDs can be linked to a cargo moiety such as a drug, peptide, or full-length protein, and can transport the moiety across the cell membrane. One well characterized PTD is the human immunodeficient virus (HIV)-1 Tat peptide (see, for example, Frankel et al., U.S. Pat. Nos. 5,804,604; 5,747,641; 6,674,980; 5,670,617; and 5,652,122; Fawell, S. et al., *Proc. Natl. Acad. Sci. U.S.A.*, 1994, 91:664-668). Peptides such as the homeodomain of *Drosophila* Antennapedia (ANTp) and arginine-rich peptides display similar properties (Derossi, D. et al., *J. Biol. Chem.*, 1994, 269:10444-10450; Derossi, D. et al., *Trends Cell Biol.*, 1998, 8:84-87; Rojas, M. et al., *Nat. Biotechnol.*, 1998, 16:370-375; Futaki, S. et al., *J. Biol. Chem.*, 2001, 276:5836-5840). VP22, a tegument protein from Herpes simplex virus type 1 (HSV-1), also has the ability to transport proteins across a cell membrane (Elliot et al., *Cell*, 1997, 88:223-233; Schwarze S. R. et al., *Trends Pharmacol. Sci.*, 2000, 21:45-48). A common feature of these carriers is that they are highly basic and hydrophilic (Schwarze S. R. et al., *Trends Cell Biol.*, 2000, 10:290-295). Coupling of these carriers to marker proteins such as beta-galactosidase has been shown to confer efficient internalization of the marker protein into cells. More recently, chimeric, in-frame fusion proteins containing these carriers have been used to deliver proteins to a wide spectrum of cell types both in vitro and in vivo. For example, VP22-p53 chimeric protein retained its ability to spread between cells and its pro-apoptotic activity, and had a widespread cytotoxic effect in p53 negative human osteosarcoma cells in vitro (Phelan, A. et al., *Nature Biotechnol.*, 1998, 16:440-443). Intraperitoneal injection of the beta-galactosidase protein fused to the HIV-1 Tat peptide resulted in delivery of the biologically active fusion protein to all tissues in mice, including the brain (Schwarze S. R. et al., *Science*, 1999, 285:1569-1572).

Liposomes of various compositions can also be used for site-specific delivery of proteins and drugs (Witschi, C. et al., *Pharm. Res.*, 1999, 16:382-390; Yeh, M. K. et al., *Pharm. Res.*, 1996, 1693-1698). The interaction between the liposomes and the protein cargo usually relies on hydrophobic interactions or charge attractions, particularly in the case of cationic lipid delivery systems (Zelphati, O. et al., *J. Biol. Chem.*, 2001, 276:35103-35110). Tat peptide-bearing liposomes have also been constructed and used to deliver cargo directly into the cytoplasm, bypassing the endocytotic pathway (Torchilin V. P. et al., *Biochim. Biophys. Acta—Biomembranes*, 2001, 1511:397-411; Torchilin V. P. et al., *Proc. Natl. Acad. Sci. USA*, 2001, 98:8786-8791). When encapsulated in sugar-grafted liposomes, pentamidine isethionate and a derivative have been found to be more potent in comparison to normal liposome-encapsulated drug or to the free drug (Banerjee, G. et al., *J. Antimicrob. Chemother.*, 1996, 38(1):145-150).

Antibodies represent another targeting device that may make liposome uptake tissue-specific or cell-specific (Mastrobattista, E. et al., *Biochim. Biophys. Acta*, 1999, 1419(2): 353-363; Mastrobattista, E. et al., *Adv. Drug Deliv. Rev.*, 1999, 40(1-2):103-127). The liposome approach offers several advantages, including the ability to slowly release encapsulated drugs and proteins, the capability of evading the immune system and proteolytic enzymes, and the ability to target tumors and cause preferentially accumulation in tumor tissues and their metastases by extravasation through their leaky neovasculature. Other carriers have also been used to deliver drugs to cells, such as polyvinylpyrrolidone nanoparticles and maleylated bovine serum albumin (Sharma, D. et al., *Oncol. Res.*, 1996, 8(7-8):281-286; Mukhopadhyay, A. et al., *FEBS Lett.*, 1995, 376(1-2):95-98). Thus, using targeting and encapsulation technologies, which are very versatile and amenable to rational design and modification, delivery of compounds to desired cells can be facilitated. Furthermore, because many liposome compositions are also viable delivery vehicles for genetic material, many of the advantages of liposomes are equally applicable to nucleic acid molecules.

As indicated above, compositions of the invention may include a liposome component. According to one example, a liposome comprises a lipid composition that is capable of fusing with the plasma membrane of a cell, thereby allowing the liposome to deliver a nucleic acid molecule and/or a protein composition into a cell. Some preferred liposomes include those liposomes commonly used in gene delivery methods known to those of skill in the art. Some preferred liposome delivery vehicles comprise multilamellar vesicle (MLV) lipids and extruded lipids, although not limited to such liposomes. Methods for preparation of MLVs are well known in the art. "Extruded lipids" are also contemplated. Extruded lipids are lipids that are prepared similarly to MLV lipids, but which are subsequently extruded through filters of decreasing size, as described in Templeton et al., *Nature Biotech.*, 1997, 15:647-652, which is incorporated herein by reference in its entirety. Small unilamellar vesicle (SUV) lipids can also be used in the compositions and methods of the present invention. Other preferred liposome delivery vehicles comprise liposomes having a polycationic lipid composition (i.e., cationic liposomes). For example, cationic liposome compositions include, but are not limited to, any cationic liposome complexed with cholesterol, and without limitation, include DOTMA and cholesterol, DOTAP and cholesterol, DOTIM and cholesterol, and DDAB and cholesterol. Liposomes utilized in the present invention can be any size, including from about 10 to 1000 nanometers (nm), or any size in between.

A liposome delivery vehicle can be modified to target a particular site in a mammal, thereby targeting and making use of compound at that site. Suitable modifications include manipulating the chemical formula of the lipid portion of the delivery vehicle. Manipulating the chemical formula of the lipid portion of the delivery vehicle can elicit the extracellular or intracellular targeting of the delivery vehicle. For example, a chemical can be added to the lipid formula of a liposome that alters the charge of the lipid bilayer of the liposome so that the liposome fuses with particular cells having particular charge characteristics. In one embodiment, other targeting mechanisms, such as targeting by addition of exogenous targeting molecules to a liposome (i.e., antibodies) may not be a necessary component of the liposome of the present invention, since effective immune activation at immunologically active organs can already be provided by the composition when the route of delivery is intravenous or intraperitoneal, without the aid of additional targeting mechanisms. However, in some embodiments, a liposome can be directed to a particular target cell or tissue by using a targeting agent, such as an antibody, soluble receptor or ligand, incorporated with the liposome, to target a particular cell or tissue to which the targeting molecule can bind. Targeting liposomes are described, for example, in Ho et al., *Biochemistry*, 1986, 25: 5500-6; Ho et al., *J Biol Chem*, 1987a, 262: 13979-84; Ho et al., *J Biol Chem*, 1987b, 262: 13973-8; and U.S. Pat. No. 4,957,735 to Huang et al., each of which is incorporated herein by reference in its entirety). In one embodiment, if avoidance of the efficient uptake of injected liposomes by reticuloendothelial system cells due to opsonization of liposomes by plasma proteins or other factors is desired, hydrophilic lipids, such as gangliosides (Allen et al., *FEBS Lett*, 1987, 223: 42-6) or polyethylene glycol (PEG)-derived lipids (Klibanov et al., *FEBS Lett*, 1990, 268: 235-7), can be incorporated into the bilayer of a conventional liposome to form the so-called sterically-stabilized or "stealth" liposomes (Woodle et al., *Biochim Biophys Acta*, 1992, 1113: 171-99). Variations of such liposomes are described, for example, in U.S. Pat. No. 5,705,187 to Unger et al., U.S. Pat. No. 5,820,873 to Choi et al., U.S. Pat. No. 5,817,856 to Tirosh et al.; U.S. Pat. No. 5,686,101 to Tagawa et al.; U.S. Pat. No. 5,043,164 to Huang et al., and U.S. Pat. No. 5,013,556 to Woodle et al., all of which are incorporated herein by reference in their entireties).

Mammalian species which benefit from the disclosed methods of treatment include, and are not limited to, apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. The terms "patient" and "subject" are used interchangeably herein are intended to include such human and non-human mammalian species. According to the method of the present invention, human or non-human mammalian nucleic acids can be administered to the patient. The nucleic acid may be naturally occurring within the subject's species or a different mammalian species. In instances where genetically modified cells are administered to a subject, the cells may be autogenic, allogeneic, or xenogeneic, for example.

The present invention includes compositions containing one or more compounds (e.g., inhibitory nucleic acid molecules) that directly or indirectly interact with the $CB_2$ promoter region, and a carrier (e.g., a pharmaceutically acceptable carrier). Compositions may include a therapeutically effective amount of a compound, and a pharmaceutically acceptable carrier. Compounds and compositions can be administered to a subject by any effective route that permits contact with the target cell type, including local or systemic delivery (e.g., intravenous). Administration can be continuous or at distinct intervals as can be determined by a person skilled in the art.

The compounds (and pharmaceutical compositions containing them), can be administered to a subject by any route that results in contact between the compound(s) and the $CB_2$ promoter region of the cell. In some embodiments, the compounds (and pharmaceutical compositions containing them) are administered to a subject by a route that results in prevention (or reduction of onset) or alleviation of symptoms associated with an allergic disease. For example, the compound can be administered parenterally, intravenously (I.V.), intramuscularly (I.M.), subcutaneously (S.C.), intradermally (I.D.), topically, transdermally, orally, intranasally, etc.

If desired, the pharmaceutical composition may be adapted for administration to the airways of the patient, e.g., nose, sinus, throat and lung, for example, as nose drops, as nasal drops, by nebulization as an inhalant, vaporization, or other methods known in the art. Examples of intranasal administration can be by means of a spray, drops, powder or gel and also described in U.S. Pat. No. 6,489,306, which is incorporated herein by reference in its entirety. Alternate embodiments include administration through any oral or mucosal routes, sublingual administration and even eye drops. However, other means of drug administrations are well within the scope of the composition.

The pharmaceutical compositions may be formulated according to known methods for preparing pharmaceutically useful compositions. Furthermore, as used herein, the phrase "pharmaceutically acceptable carrier" includes any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients used in the compositions. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations containing pharmaceutically acceptable carriers are described in a number of sources which are well known and readily available to those skilled in the art. For example, *Remington's Pharmaceutical Sciences* (Martin E. W., 1995, Easton Pa., Mack Publishing Company, $19^{th}$ ed.), which is incorporated herein by reference in its entirety, describes formulations that can be used in connection with the compositions.

Pharmaceutical compositions useful for parenteral injection may include pharmaceutically acceptable sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents, or vehicles include water, ethanol, polyol (such as glycerol, propylene glycol, polyethylene, lycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants. Formulations suitable for parenteral administration include, for example, aqueous injectable solutions that may contain antioxidants, buffers, and solutes which render the formulation isotonic with the blood of the intended recipient; and aqueous and non-aqueous sterile suspensions, which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that, in addition to the ingredients particularly mentioned above, the formulations of the subject invention can include other agents conventional in the art having regard to the type of formulation in question.

The pharmaceutical compositions used in the methods may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption, such as aluminum monostearate and gelatin.

In some cases, in order to prolong the effect of the compound, it is desirable to slow the absorption from subcutaneous or intramuscular injection. This may be accomplished by the use of a liquid suspension of crystalline or amorphous material with poor water solubility. The rate of absorption of the compound then depends upon its rate of dissolution which, in turn, may depend upon crystal size and crystalline form. Alternatively, delayed absorption of a parenterally administered compound is accomplished by dissolving or suspending the compound in an oil vehicle.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the compounds are mixed with it least one pharmaceutically acceptable excipient or carrier such as sodium nitrate or dicalcium phosphate and/or a) fillers or extenders such as starches, lactose, sucrose, glucose, mannitol, and silicic acid; b) binders such as, for example, carboxymethylcellulose, alginates, gelatin, polyvinylpyrrolidone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as, for example, cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. Optionally, the solid dosage forms contain opacifying agents, and can be of a composition that releases the compound only, or preferentially, in a certain part of the intestinal tract, optionally, in a delayed manner. Examples of embedding compositions that can be used include polymeric substances and waxes.

The compound can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compound, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder, which may be pressurized or non-pressurized. In non-pressurized powder compositions, the active ingredients in finely divided form may be used in admixture with a larger-sized pharmaceutically acceptable inert carrier comprising particles having a size, for example, of up to 100 µm in diameter. Suitable inert carriers include sugars such as lactose. Desirably, at least 95% by weight of the particles of the active ingredient have an effective particle size in the range of 0.01 to 10 µm.

Alternatively, the pharmaceutical composition may be pressurized and contain a compressed gas, such as nitrogen or a liquefied gas propellant. The liquefied propellant medium or the entire composition is preferably such that the active ingredients do not dissolve therein to any substantial extent. The pressurized composition may also contain a surface active agent. The surface active agent may be a liquid or solid non-ionic surface active agent or may be a solid anionic surface active agent. It is preferred to use the solid anionic surface active agent in the form of a sodium salt.

The compositions and methods may further incorporate permeation enhancers, such as those described in U.S. Patent Publication No. 2003/0147943 (Luo et al.), penetrating peptides capable of facilitating penetration of a compound, across a biological barrier, such as those described in U.S. Patent Publication No. 2004/0146549 (Ben-Sasson et al.), enhancer compounds that enhance the absorption of a polypeptide in the respiratory tract, such as those described in U.S. Patent Publication No. 2004/0171550 (Backstrom et al.), and suspension vehicles, such as those described in U.S. Patent Publication No. 2004/0224903 (Berry et al.), each of which are incorporated herein by reference in their entirety.

The compound is administered and dosed in accordance with good medical practice, taking into account the clinical condition of the individual patient, the site and method of administration, scheduling of administration, patient age, sex, body weight, and other factors known to medical practitioners. The pharmaceutically "effective amount" for purposes herein is thus determined by such considerations as are known in the art. For example, an effective amount of amount is that amount necessary to provide an effective amount of the compound to the $CB_2$ promoter region in vivo or in vitro. The amount of the compound can be effective to achieve some improvement including, but not limited to, more rapid recovery, total prevention of symptoms associated with an allergic disease, or improvement or elimination of symptoms associated with an allergic disease, and other indicators as are selected as appropriate measures by those skilled in the art. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for local or systemic administration based on the size of a mammal and the route of administration.

Various methods may include a step that involves comparing a value, level, feature, characteristic, property, etc. to a "suitable control", referred to interchangeably herein as an "appropriate control". A "suitable control' or "appropriate control" is any control or standard familiar to one of ordinary skill in the art useful for comparison purposes. In one embodiment, a "suitable control" or "appropriate control" is a value, level, feature, characteristic, property, etc. determined before, during, or after contacting an $CB_2$ promoter region with a candidate compound, as described herein. For example, a transcription rate, mRNA level, translation rate, protein level, biological activity, cellular characteristic or property, genotype, phenotype, etc. can be determined prior to introducing a candidate into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Measuring expression includes determining or detecting the amount of the polypeptide present in a cell or shed by it, as well as measuring the underlying mRNA, where the quantity of mRNA present is considered to reflect the quantity of polypeptide manufactured by the cell. Furthermore, the gene for the $CB_2$ receptor can be analyzed to determine whether there is a gene defect responsible for aberrant expression or polypeptide activity.

Polypeptide detection can be carried out by any available method, e.g., by Western blots, ELISA, dot blot, immunoprecipitation, RIA, immunohistochemistry, etc. For instance, a tissue section can be prepared and labeled with a specific antibody (indirect or direct and visualized with a microscope. Amount of a polypeptide can be quantitated without visualization, e.g., by preparing a lysate of a sample of interest, and then determining by ELISA or Western the amount of polypeptide per quantity of tissue. Antibodies and other specific binding agents can be used. There is no limitation as to how detection of $CB_2$ receptor is performed.

Assays can be utilized which permit quantification and/or presence/absence detection of a target nucleic acid or polypeptide ($CB_2$) in a sample. Assays can be performed at the single-cell level, or in a sample comprising many cells, where the assay is "averaging" expression over the entire collection of cells and tissue present in the sample. Any suitable assay format can be used, including, but not limited to, e.g., Southern blot analysis, Northern blot analysis, polymerase chain reaction ("PCR") (e.g., Saiki et al., *Science* 1988, 241, 53; U.S. Pat. Nos. 4,683,195, 4,683,202, and 6,040,166; PCR Protocols: A Guide to Methods and Applications, Innis et al., eds., Academic Press, New York, 1990), reverse transcriptase polymerase chain reaction ("RT-PCR"), anchored PCR, rapid amplification of cDNA ends ("RACE") (e.g., Schaefer in Gene Cloning and Analysis: Current Innovations, Pages 99-115, 1997), ligase chain reaction ("LCR") (EP 320 308), one-sided PCR (Ohara et al., *Proc. Natl. Acad. Sci.* 1989, 86, 5673-5677), indexing methods (e.g., U.S. Pat. No. 5,508,169), in situ hybridization, differential display (e.g., Liang et al., *Nucl. Acid. Res.* 1993, 21, 3269 3275; U.S. Pat. Nos. 5,262,311, 5,599,672 and 5,965,409; WO97/18454; Prashar and Weissman, *Proc. Natl. Acad. Sci.*, 93:659-663, and U.S. Pat. Nos. 6,010,850 and 5,712,126; Welsh et al., *Nucleic Acid Res.*, 20:4965-4970, 1992, and U.S. Pat. No. 5,487,985) and other RNA fingerprinting techniques, nucleic acid sequence based amplification ("NASBA") and other transcription based amplification systems (e.g., U.S. Pat. Nos. 5,409,818 and 5,554,527; WO 88/10315), polynucleotide arrays (e.g., U.S. Pat. Nos. 5,143,854, 5,424,186; 5,700,637, 5,874,219, and 6,054,270; PCT WO 92/10092; PCT WO 90/15070), Qbeta Replicase (PCT/US87/00880), Strand Displacement Amplification ("SDA"), Repair Chain Reaction ("RCR"), nuclease protection assays, subtraction-based methods, Rapid-Scan, etc. Additional useful methods include, but are not limited to, e.g., template-based amplification methods, competitive PCR (e.g., U.S. Pat. No. 5,747, 251), redox-based assays (e.g., U.S. Pat. No. 5,871,918), Taqman-based assays (e.g., Holland et al., *Proc. Natl. Acad. Sci.* 1991, 88, 7276-7280; U.S. Pat. Nos. 5,210,015 and 5,994,063), real-time fluorescence-based monitoring (e.g., U.S. Pat. No. 5,928,907), molecular energy transfer labels (e.g., U.S. Pat. Nos. 5,348,853, 5,532,129, 5,565,322, 6,030, 787, and 6,117,635; Tyagi and Kramer, Nature Biotech., 14:303-309, 1996). Any method suitable for single cell analysis of gene or protein expression can be used, including in situ hybridization, immunocytochemistry, MACS, FACS, flow cytometry, etc. For single cell assays, expression products can be measured using antibodies, PCR, or other types of nucleic acid amplification (e.g., Brady et al., *Methods Mol. & Cell. Biol.* 1990, 2, 17-25; Eberwine et al., *Proc. Natl. Acad. Sci.* 1992, 89, 3010-3014; U.S. Pat. No. 5,723,290). These and other methods can be carried out conventionally, e.g., as described in the mentioned publications.

The terms "transfection", "transformation", and "introduction", and grammatical variations thereof, are used interchangeably herein to refer to the insertion of an exogenous nucleic acid molecule (e.g., inhibitory nucleic acid molecule such as RNAi molecule). The insertion of a nucleic acid molecule per se and the insertion of a plasmid or vector comprised of the exogenous nucleic acid molecule are included. The exogenous nucleic acid molecule may be directly transcribed and translated by the cell, maintained as a nonintegrated vector, for example, a plasmid, or alternatively, may be stably integrated into the host genome.

The phrases "isolated" or "biologically pure" refer to material that is substantially or essentially free from components which normally accompany the material as it is found in its native state.

The terms "cell" and "cells" are used interchangeably herein to refer to a single cell or plurality of cells (i.e., at least one cell). In some embodiments, host cells are used in the methods disclosed. However, tissues, and genetically modified or transgenic animals may also be utilized.

The terms "comprising", "consisting of" and "consisting essentially of" are defined according to their standard meaning. The terms may be substituted for one another throughout the instant application in order to attach the specific meaning associated with each term.

As used in this specification, the singular forms "a", "an", and "the" include plural reference unless the context clearly dictates otherwise. Thus, for example, a reference to "a cell" includes more than one such cell. Reference to "a receptor" includes more than one such receptor. Reference to "a nucleic acid molecule" includes more than one such nucleic acid molecule. Reference to "a polypeptide" or "compound" includes more than one such polypeptide or compound, and the like.

The practice of the methods and compositions described herein may employ, unless otherwise indicated, conventional techniques of molecular biology, microbiology, recombinant DNA technology, electrophysiology, and pharmacology that are within the skill of the art. Such techniques are explained fully in the literature (see, e.g., Sambrook, Fritsch & Maniatis, Molecular Cloning: A Laboratory Manual, Second Edition (1989); DNA Cloning, Vols. I and II (D. N. Glover ed. 1985); Perbal, B., A Practical Guide to Molecular Cloning (1984); the series, Methods In Enzymology (S. Colowick and N. Kaplan eds., Academic Press, Inc.); Transcription and Translation (Hames et al. eds. 1984); Gene Transfer Vectors For Mammalian Cells (J. H. Miller et al. eds. (1987) Cold Spring Harbor Laboratory, Cold Spring Harbor, N.Y.); Scopes, Protein Purification: Principles and Practice (2nd ed., Springer-Verlag); and PCR: A Practical Approach (McPherson et al. eds. (1991) IRL Press)).

All patents, patent applications, provisional applications, and publications referred to or cited herein, supra or infra, are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Materials and Methods

BIOINFORMATICS ANALYSIS. The bioinformatics programs used for this study include the GCG SeqWeb v3.1 software package, Primer3 (Rozen and Skaletsky, *Methods Mol Biol*, 2000, 132:365-386), the Genomatix Suite, Consite, the Database of Transcriptional Start Sites (DBTSS), ClustalW and databases such as Ensembl, and NCBI.

MICE. C57BL/6 mice, 8 to 10 wks old and of mixed gender, were obtained from NCI (Fredericksburg, Md.) and housed and cared for in the University of South Florida Health Sciences Center animal facility, which is fully accredited by the American Association for Accreditation of Laboratory Animal Care.

ISOLATION OF MOUSE SPLENOCYTES, T AND B LYMPHOCYTES. Mice were euthanized by $CO_2$ asphyxiation, followed by removal of the spleens, which were placed in 12 ml of hanks balanced buffer saline (HBBS) then dispersed with a Seward Stomacher® 80 (Lab System, England) to release the splenocytes. The splenocytes where collected by centrifugation at 1100 rpm for 10 minutes at 10° C., and washed once with PBS. The T and B cells were then isolated by magnetic negative selection using the EasySep® mouse T or B cell enrichment Kits (Stem Cell Technologies, Canada) following the manufacturer's protocol. Total RNA was extracted from the lymphocytes immediately following isolation, except for B cells activated by LPS (5 µg/ml) for up to 8 hrs.

HUMAN SUBJECTS, ISOLATION OF PERIPHERAL BLOOD MONONUCLEAR CELLS (PBMCS) AND B LYMPHOCYTES. Human subjects recruited for this study were laboratory workers at the University of South Florida (USF) who gave informed consent. Venous blood (25 ml) was drawn into 4 $K_3$ EDTA vacutainer tubes (Becton Dickinson, Franklin Lakes, N.J.), then diluted 1:1 or 1:2 with RPMI 1640 medium (Sigma, St Louis, Mo.). The PBMCs were isolated from blood using Hisopaque®-1077 (Sigma Diagnostics, Inc.) following the manufacturer's protocol. B cell isolation was performed by magnetic negative selection using the EasySep® human B cell enrichment kit (StemCell Technologies, Canada).

PHENOTYPIC ANALYSIS OF IMMUNE CELL POPULATIONS. Mouse T and B cell subtypes were analyzed for enrichment by PCR and FACS analysis. RACE cDNA of the T and B cell samples was analyzed by PCR amplification using specific primers for the CDR chain of the T cell receptor and for the B cell marker CD19 (50). Enrichment of the B cell preparation is determined by the absence of CD3ϵ, while T cell enrichment is determined by the absence of CD19. PCR amplification was performed using 1 µl of RACE cDNA, 500 nM of each primer and Taq polymerase supplied with the SMART RACE cDNA Amplification kit (Clontech Inc., Madison, Wis.) in a final volume of 25□. Amplification was for 28 cycles using the MyCycler™ thermal cycler (Bio-Rad Laboratories, Hercules, Calif.). β-actin was used as a loading control. FACS analysis of the purified mouse T and B cell populations was done by labeling $10^6$ cells with fluorochrome-conjugated anti-mouse mAbs; CD19-PE, CD3-PerCP, NK-pan-FITC and F/480-APC (BD Pharmingen, San Jose, Calif.). The human B cell populations were analyzed for enrichment by labeling $10^5$ cells with fluorochrome-conjugated anti-human mAbs; CD19-PE, CD3-FITC and CD14-APC (BD Pharmingen, San Jose, Calif.). All flow cytometric analysis was conducted using a FACS Caliber flow cytometer and Cell Quest software (Becton Dickinson, San Diego, Calif., USA).

RNA EXTRACTION. Total RNA was extracted from the cell populations by standard techniques using Tri-reagent (Sigma; 1 ml per $10^7$ cells) and quantitated using the RiboGreen RNA Quantitation Kit (Molecular Probes, Eugene, Oreg.). Just prior to cDNA synthesis, residual DNA was removed by treatment with Turbo DNA-free™ (Ambion Inc., Austin, Tex.) following manufacturer's protocol.

REVERSE TRANSCRIPTASE-POLYMERASE CHAIN REACTION (RT-PCR). To synthesize the cDNA, 1.0 µg of the DNAse treated RNA was primed with 1 µl of random primers for 5 minutes at 70° C., then reverse transcribed (RT) at 37° C. for 1 hr using 15 U avian myeloblastosis virus (AMV), 40 Units RNasin (Promega, Corp., Madison, Wis.) and 1.25 mM mix of dNTPs (Promega Corp., Madison, Wis.) in a volume of 20 µl. The PCR reaction was carried out in 25 µl containing 1 µl cDNA, 500 nM of each primer (see Table 3), with 12.5 µl GoTaq Green Master Mix (Promega Corp., Madison, Wis.) and amplified using the MyCycler™ thermal cycler (Bio-Rad Laboratories, Hercules, Calif.). The PCR amplification conditions were as follows; for the initial denaturation step, 95° C. for 1 min, followed by 32 cycles at 95° C. for 20 sec, 55° C. for 30 sec, 72° C. for 45 sec, with a final elongation at 72° C. for 3 min.

SMART-5'-RACE. To identify the TSS, this technique was employed: Switching Mechanism At 5' end of RNA Transcript Rapid Amplification of cDNA Ends (SMART™ RACE cDNA Amplification kit, Clontech Inc., Madison, Wis.) following manufacturer's protocol. Two reverse gene specific primers (GSP) were designed, for both mouse and human $CB_2$ using the GCG SeqWeb v3.1 software (see Table 1 for primer sequences). The mouse GSP 1 (mCB2-R301) binds within the ORF 301 bp downstream of the ATG, while the human GSP1 (hCB2-R298) binds 298 bp downstream of the ATG. These were used with the universal primer mix (UPM) that anneals to the SMART sequence at the 5' end of the cDNA and is supplied with the kit for the initial PCR reaction.

A second GSP2 (mCB2-R217 and hCB2-R163), located 84 bp upstream of mCB2-R301, and 74 bp upstream of human GSP1, was used with UPM in a nested PCR for $CB_2$ confirmation. RACE products were run on a 2% agarose gel, visualized with ethidium bromide and purified using the Perfectprep® Gel Cleanup kit (Eppendorf, North America) following manufacturer's protocol, and sent to the Moffitt/USF Molecule Biology Core lab for DNA sequencing. The SeqWeb PileUp program was used to compare the RACE sequences with the GenBank mouse mCnr2 and human hCNR2 sequences to confirm $CB_2$ identity, exonal usage, and location of the TSSs.

TABLE 1

SMART 5' RACE primers used to identify the TSS.

| Gene Specific Primer Name[a] | Sequence 5'-to-3' | Size (mer) | 5' end binding site[b] |
|---|---|---|---|
| Mouse GSP1 mCB2-R301 | CGACCCCGTGGAAGACGTGGAAGATGACAA (SEQ ID NO: 176) | 30 | 301 bp downstream ATG |
| Mouse GSP2 mCB2-R217 | TGAACAGGTACGAGGGCTTTCT (SEQ ID NO: 177) | 22 | 217 bp downstream ATG |
| Human GSP1 hCB2-R298 | GCCAGGAAGTCAGCCCCAGCCAAGCTGCCAA (SEQ ID NO: 178) | 31 | 298 bp downstream ATG |
| Human GSP2 hCB2-R163 | GCACAGCCACGTTCTCCAGGGCACTTAGCA (SEQ ID NO: 179) | 30 | 163 bp downstream ATG |

[a]GSP, gene specific primer; 1 designates used for the initial RACE PCR, 2 used for nested PCR.
[b]The number of base pairs from the start of translation in which the 5' end of the GSP binds for amplification of $CB_2$. The primers were designed to include enough of the coding region for $CB_2$ confirmation of the RACE transcripts.

PCR AND RT-PCR PRIMER MAPPING. Genomic DNA was extracted from mouse splenic and human peripheral B cells using the Wizard® Genomic DNA Isolation System (Promega Corp., Madison, Wis.) following manufacturer's protocol. RNA was extracted, DNAse treated and reverse transcribed from mouse and human B cells as stated above. Using Primer3, forward primers were designed to flank the TSSs identified by 5'RACE (FIGS. 11A-B and 12A-B) 2 to 10 bp in either direction. Forward primers upstream of the TSS should only amplify genomic DNA, whereas forward primers downstream of the TSS should amplify genomic DNA as well as cDNA derived from the $CB_2$ transcripts. The PCR reaction was carried out in 25 µl containing either 1 µl cDNA or 1 µl DNA, 500 nM of each primer (see Table 3), with 12.5 µl GoTaq Green Master Mix (Promega Corp.) and amplified using the MyCycler™ thermal cycler (Bio-Rad Laboratories, Inc). The PCR amplification conditions were as stated above with minor adjustments, the cycle number was increased to 35 and for the mouse samples elongation was increased to 1.5 minutes.

TABLE 2

Primers Used for Mapping the TSSs.

| Primer Group[a] | | | Sequence 5'-to-3'[b] | | Assay[c] | Size of amplicon |
|---|---|---|---|---|---|---|
| mE1b | DNA | A | Ggaggaggcatgaggca | (SEQ ID NO: 180) | PCR | 189 bp |
| | mRNA | B | ACACATAGCCTGGCACA | (SEQ ID NO: 181) | RT-PCR | 171 bp |
| | | C | GCGGTTGAATTCTCTCTTC | (SEQ ID NO: 182) | | |
| | | G | GACAAAGTTGCAGGCGAAGATCAC | (SEQ ID NO: 183) | | 755 bp |
| mE2 | DNA | D | Atacatcaaacacatccttg | (SEQ ID NO: 184) | PCR | 224 bp |
| | mRNA | E | TTCTAGAAGGCACCCATGT | (SEQ ID NO: 185) | RT-PCR | 189 bp |
| | | F | CCTCTGCTCATTCAGGTACA | (SEQ ID NO: 186) | | |
| | | G | GACAAAGTTGCAGGCGAAGATCAC | (SEQ ID NO: 187) | | 567 bp |

TABLE 2-continued

Primers Used for Mapping the TSSs.

| Primer Group[a] | | | Sequence 5'-to-3'[b] | | Assay[c] | Size of amplicon |
|---|---|---|---|---|---|---|
| hE1 | DNA | J | Gcaagagaaagctggctt | (SEQ ID NO: 188) | PCR | 99 bp |
| | mRNA | I | TCAACAGGTGCTCTGAGTG | (SEQ ID NO: 189) | RT-PCR | 71 bp |
| | | H | CTGAGGAGTCCCAGTTGTT | (SEQ ID NO: 190) | | |

[a]m, mouse; h, human; E1b, exon 1b; E2, exon 2; A, D, J, DNA forward primers; B, E, I, forward primers for amplification of mRNA derived cDNA; C, F, G, H, reverse primers.
[b]Primers designed to bind genomic DNA 5' of the TSSs are in lower case.
[c]RT-PCR, reverse transcription polymerase chain reaction.

QUANTITATIVE REAL TIME PCR (RT-QPCR). Mouse $mCB_2$ transcript exonal usage in resting and LPS (5 μg/ml) stimulated splenic B cells was measured by qRT-PCR, in which a duplex Taqman PCR strategy was employed; 4 $mCB_2$ exon specific primer sets and probes were designed, one each for the $mCB_2$ exons (1a, 1b, 2, and 3) and 1 primer and probe set for the endogenous β-actin control using Primer3 (see Table 3 for primer/probe sequences). The real-time PCR was carried out in 20 μl containing 1 μl cDNA, 300 nM β-actin and 500 nM $CB_2$ primers, 250 nM fluorescent probe (6-FAM for $mCB_2$ exon, ROX for β-actin), with 10 μl IQ™ Multiplex Powermix, and performed in the iCycler IQ™ Real-Time PCR detection system (Bio-Rad Laboratories, Inc). In brief, the reaction was performed in duplicate for each RT cDNA product (see above). Samples were heated for 10 min at 95° C., followed by 50 cycles of amplification for 15 s at 95° C. and 1 min at 60° C.

TABLE 3

Primers and taqman probes used in this study.

| Primer pairs[a] and probe | | Sequence 5'-to-3'[b] | Assay[c] | Size of amplicon[d] |
|---|---|---|---|---|
| mCB2-E3 | F | GCCGTGCTCTATATTATCCTGTCCTC (SEQ ID NO: 191) | qRT-PCR | 120 bp |
| | R | GACAAAGTTGCAGGCGAAGATCAC (SEQ ID NO: 192) | | |
| | P | 6FAM-AGAAAGCCCTCGTACCTGTTCATCAGCA-BHQ1 (SEQ ID NO: 193) | | |
| mCB2-E1a | F | TCATCTGCGAAAGTGTGA (SEQ ID NO: 194) | qRT-PCR | 112 bp |
| | R | TTGTCCTGGCTATTCTGTATC (SEQ ID NO: 195) | | |
| | P | 6FAM-CTGGAGCTGCAGCTCTTGGGAC-BHQ1 (SEQ ID NO: 196) | | |
| mCB2-E1b | F | ACACATAGCCTGGCACA (SEQ ID NO: 197) | qRT-PCR | 171 bp |
| | R | GCGGTTGAATTCTCTCTTC (SEQ ID NO: 198) | | |
| | P | 6FAM-TCAAGTGAGTTGCAGGACAGCATAC-BHQ1 (SEQ ID NO: 199) | | |
| mCB2-E2 | F | TTCTAGAAGGCACCCATGT (SEQ ID NO: 200) | qRT-PCR | 189 bp |
| | R | CCTCTGCTCATTCAGGTACA (SEQ ID NO: 201) | | |
| | P | 6FAM-CTTCCTGTTGCTGTGTGCATCCT-BHQ1 (SEQ ID NO: 202) | | |
| β-actin | F | GGGAATGGGTCAGAAGGACT (SEQ ID NO: 203) | qRT-PCR | 134 bp |
| | R | AGGTGTGGTGCCAGATCTTC (SEQ ID NO: 204) | | |
| | P | ROX-ATGTGGGTGACGAGGCCCAGAGCAA-BHQ2 (SEQ ID NO: 205) | | |

[a]E3, exon 3; E1a, exon 1a; E1b, exon 1b; E2, exon 2; F, forward primer; R, reverse primer; P, Taqman® probe.
[b]6FAM, 6-carboxyfluorescein; BHQ1 or 2, Black Hole Quencher®-1 or 2.

PROMOTER CLONING. Using genomic DNA extracted from mouse B cells (see above) and the pGL3-enhancer vector (Promega), two clones were constructed to test for promoter activity surrounding the TSSs of the mouse exon 1 and 2 $CB_2$ transcript variants. The clones included the region from −359 bp to +205 bp of the TSS (+1) of exon 1a, whereas the second clone spanned the region from +68 bp to +205 bp of the exon 2 TSS (+1). The DNA regions were PCR amplified (see Table 4 for primer sequences) and initially cloned into the pBlue TOPO-TA vector (Invitrogen) following manufacturer's protocol, then sub-cloned by standard methods, into the pGL3-enhancer vector via the Hind III restriction enzyme site.

er's protocol. In brief, cells were collected by centrifugation at 600 RCF for 10 minutes and washed 1× with PBS. Cells were lysed using 200 μl of CCLR, of which 20 μl was used for the luciferase assay and the remaining lysate was stored at −80° C. Each sample was in duplicate and luciferase activity was measured using the MLX luminometer (Dynex Technologies Inc., Chantilly, Va.). A standard curve was used to measure the amount of lucerifase protein in each sample.

ACTIVATION OF B CELLS. To activate B cells, the B cell mitogen, LPS, and known inducers of immunoglobulin class switching IL-4 and anti-CD40 were utilized. Purified primary splenic B cells were cultured in RPMI medium containing 10% FCS with either 5 μg/ml LPS or 3 ng/ml IL-4 and 0.5

TABLE 4

Promoter Clones and PCR Primers.

| Promoter clone | Primers | Sequence 5'-to-3' | Promoter region cloned | Size (bp) |
|---|---|---|---|---|
| pGL3-E16 | E1 − 352F | GGCACATGTCACAGACAA (SEQ ID NO: 206) | −270 bp to +205 bp | 475 |
|  | E1 + 123R | GCGAAGAGTTAGGGAAGAGT (SEQ ID NO: 207) | exon 1a TSS(+1) |  |
| pGL3-E19 | E1 − 14F | CCTGCTGGGTCTCCAGAT (SEQ ID NO: 208) | +68 bp to +205 bp | 137 |
|  | E1 + 123R | GCGAAGAGTTAGGGAAGAGT (SEQ ID NO: 209) | exon 1a TSS(+1) |  |
| pGL3-E25 | E1 − 441F | GTTCAATTCCCAGCACCC (SEQ ID NO: 210) | −359 bp to +63 bp | 422 |
|  | E1 − 19R | CCCACGTAGGTCCCAAGAG (SEQ ID NO: 211) | exon 1a TSS(+1) |  |
| pGL3-P7 | E2 − F189 | CTTGCCAGTTCCCAGTTTCA (SEQ ID NO: 212) | −189 bp to +36 bp | 225 |
|  | E2 + R36 | CAAGTCACATGGGTGCCTTCT (SEQ ID NO: 213) | exon 2 TSS(+1) |  |
| pGL3-P8 | E2 − F90 | AGAAGAGGGACTTGCCCAAA (SEQ ID NO: 214) | −90 bp to +36 bp | 126 |
|  | E2 + R36 | CAAGTCACATGGGTGCCTTCT (SEQ ID NO: 215) | exon 2 TSS(+1) |  |
| pGL3-P10 | E2 + F13 | TCTAGAAGGCACCCATGTGA (SEQ ID NO: 216) | +13 bp to +205 bp | 192 |
|  | E2 + R205 | CTGTGCCTCTGCTCATTCAG (SEQ ID NO: 217) | exon 2 TSS(+1) |  |
| pGL3-P11 | E2 − F189 | CTTGCCAGTTCCCAGTTTCA (SEQ ID NO: 218) | −189 bp to +101 bp | 290 |
|  | E2 + R101 | AACAGGATGCACACAGCAAC (SEQ ID NO: 219) | exon 2 TSS(+1) |  |
| pGL3-P13 | E2 − F25 | TCAAACACATCCTTGCCCTA (SEQ ID NO: 220) | −25 bp to +101 bp | 126 |
|  | E2 + R101 | AACAGGATGCACACAGCAAC (SEQ ID NO: 221) | exon 2 TSS(+1) |  |

TRANSFECTION OF B CELLS. Primary B cells were cultured for 24 to 48 hrs in RPMI medium containing 10% FCS, 10 ng/ml IL-4 and 500 ng/ml anti-CD40, then transfected ($10^7$ cells/500 μl RPMI in 0.4-cm cuvettes) with the pGL3-clones (10 μg) by electroporation at 250 V and 800 μFarads using the Gene Pulser (BioRad). The transfected B cells were collected within 18 to 24 hrs after electroporation. For each cell sample a 50 μl aliquot was removed and mixed with an equal volume of Trypan Blue to obtain cell number and check viability. Cells were counted using a hemocytometer and compound light microscope.

LUCIFERASE REPORTER ASSAY. Cell lysates of the transfected cells were analyzed for luciferase activity using Promega's Luciferase Assay System, following manufactur- μg/ml anti-CD40 for 1, 3, and 8 hrs. Total RNA was isolated at each time point and analyzed for transcript expression by RT-qPCR. Relative transcript expression was determined by the $2^{-\Delta\Delta Ct}$ method, in which β-actin was the endogenous control and time 0 (un-stimulated) was the calibrator.

EXAMPLE 1

Bioinformatics Analysis of the $CB_2$ (CNR2) and Genbank Clones

Figure 3B:
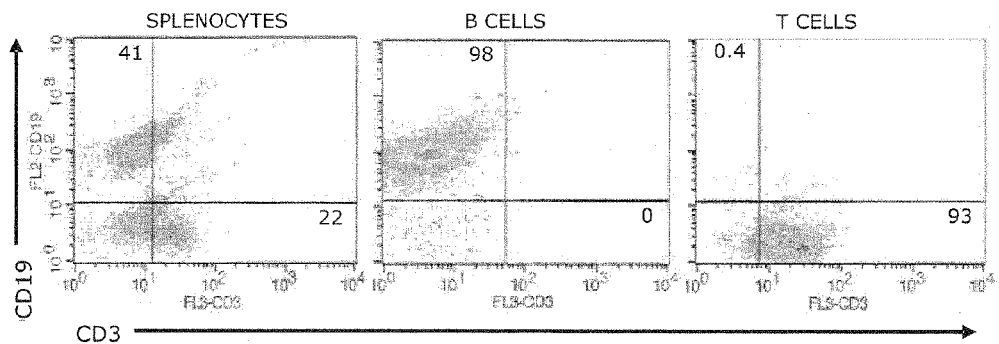
Figure 3C:
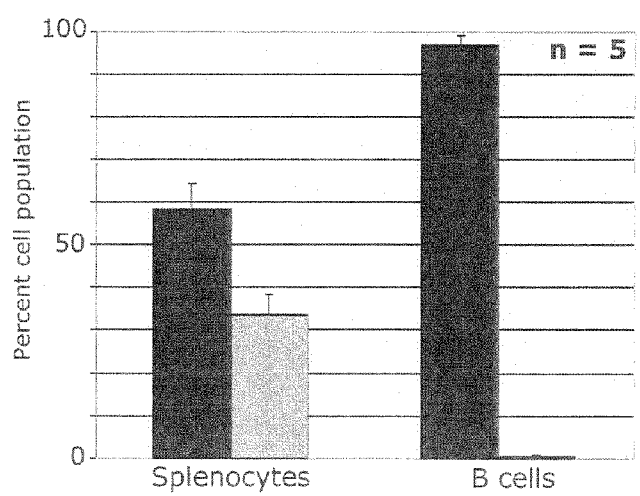
Figure 4A:
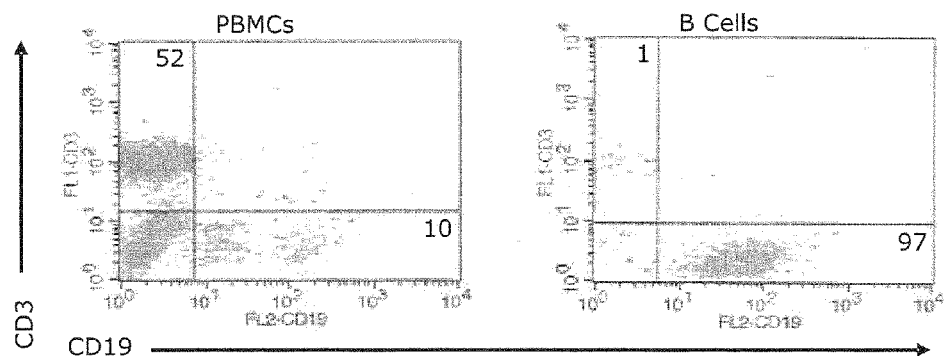
FIGS. 4A and 4B show results of phenotypic analysis of lymphocyte subtypes isolated from human PBMCs. Human B cells isolated from PBMCs by affinity purification were analyzed with CD19-PE, CD3-FITC and CD14-APC anti-human mAbs (CD14 data not shown) to determine B cell enrichment. Scatter plots are shown in FIG. 4A. The bar graph in FIG. 4B represents data from 3 human donors. Black bars are B cells and grey bars are T cells.
Figure 4B:
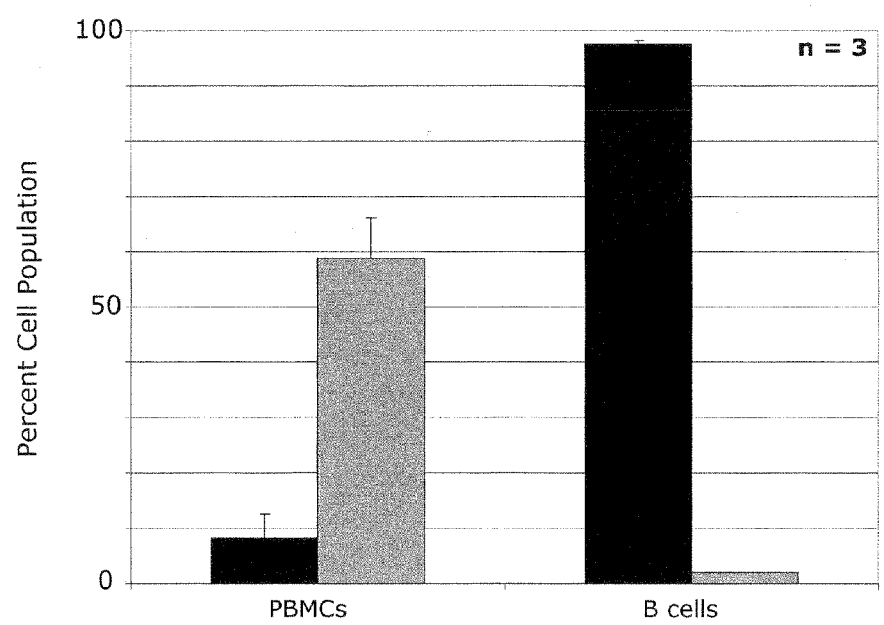

Since the discovery of $CB_2$, several cDNA clones from various mouse and human tissues, as well as the complete gene sequence have been submitted to GenBank and available to researchers. The present inventors therefore took advantage of this resource to gain initial insight as to how the $CB_2$ receptor gene is expressed in B cells. Initially, the present inventors explored genome databases, such as Ensembl and NCBI, to obtain the location and gene structure of mouse and human CNR2. The mouse Cnr2 (mCnr2) was reported to be located on chromosome 4, 24.7 kb in size, and produce at least two transcripts containing different 5' untranslated region (UTR) first exons (FIGS. 3A & 3B). Whereas human CNR2 (hCNR2) was reported on chromosome 1, 39.4 kb in size, and express a single transcript (FIGS. 4A & 4B). A consensus was reported among the mouse and human clones in which the ORF, encoding $CB_2$ protein, was within a single exon—exon 3 for mouse and exon 2 for human (FIGS. 1A-1C and 2A-2C). Further computational analysis using the GCG SeqWeb package to align the 5'UTR of the GenBank™ clones, revealed the mouse clones from various immune tissues share a similar 5'UTR first exon (exon 1) that differed in length at their most 5' nucleotide. Similarly, the clones reported from bone and liver share a second common 5'UTR first exon (exon 2) yet differ in length at the 5' nucleotide (FIG. 1C). Analysis of human data (FIG. 2C) showed only one full length human $CB_2$ clone containing a 5'UTR first exon (exon 1). This analysis suggested that the mouse gene, mCnr2, utilizes multiple TSSs to produce at least two $CB_2$ transcript variants whereas the human gene, hCNR2, utilizes only one. However, none of this existing data provided information as to the location of the TSS and $CB_2$ transcript variants utilized in B cells. Therefore, the present inventors began to investigate the TSS and $CB_2$ transcripts in B cells purified from mouse splenocytes and human PBMCs.

EXAMPLE 2

Phenotype of Lymphocyte Subtypes

Studies have shown that $CB_2$ mRNA is most abundant in mouse and human B cells (Carayon, P. et al., *Blood*, 1998, 92:3605-3615; Galieque, S. et al., *Eur. J. Biochem.*, 1995, 232:54-61; Lee, S. F. et al., *Eur. J. Pharmacol.*, 2001, 423: 235-241) and the bioinformatic analysis performed above revealed that the mCnr2 produces at least two transcripts, whereas the hCNR2 produces only one (FIGS. 3A-3C and 4A-4B). However, from the database, information pertaining to the location of the TSS or $CB_2$ transcript usage in purified mouse and human B cells could not be found. Therefore, the present inventors began an analysis for $CB_2$ transcript initiation and usage in un-stimulated, resting purified B cells from mouse splenocytes and human PBMCs. T and B cells were purified using the EasySep® negative selection kits for mouse and human. Splenocytes from mice and blood mononuclear cells from humans were processed over antibody affinity columns to remove all lymphoid subtypes with the exception of B cells and T cells. The present inventors then employed RT-PCR and flow cytometry to determine enrichment of the lymphocyte subtypes. RT-PCR determined either the presence or absence of the T cell specific CDR message or the B cell specific message, CD19. Enrichment of the B cell preparation was determined by the presence of CD19 and absence of CD3ε, whereas T cell enrichment was determined by the presence of CDR and absence of CD19. PCR amplification was performed using CD3ε and CD19 specific primers (Wang, X. et al., *Nucleic Acids Research*, 2003, 31:e154) for 28 cycles, in which weak to no visible CD19 bands were seen in the T cell populations and weak CD3ε bands were seen in the B cell population (FIG. 3A). Because of the weak bands seen in the lymphocyte subtypes, the present inventors unable to determine the percent purification of the lymphocyte subtypes. Therefore, to determine more precisely the purity of the subtypes, flow cytometry analysis was performed using CD19 and CD3 fluorescent labeled antibodies and demonstrated that the mouse B and T cell populations as well as the human B cell populations were enriched to greater than 95% (FIGS. 3A-3C and 4A-4B). These results show that the purified lymphocyte subtypes were indeed highly enriched.

EXAMPLE 3

Mouse and Human B Cells Differ in the Number of $CB_2$ TSSs

Figure 5A:
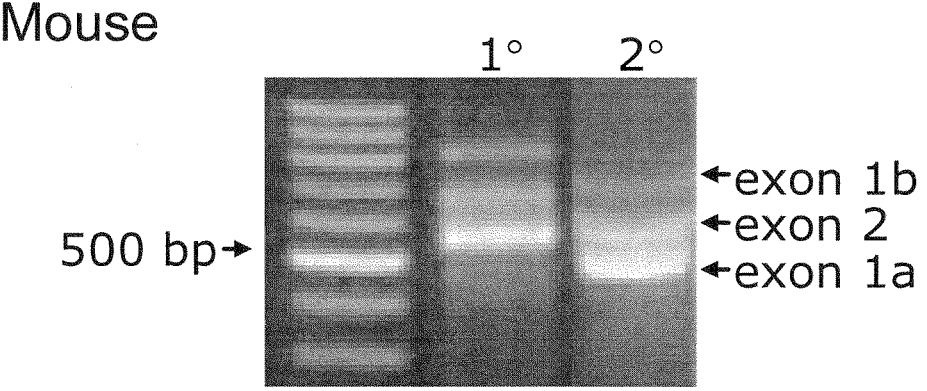
FIGS. 5A and 5B show mouse and human $CB_2$ Transcripts and TSSs Identified by 5' RACE. Gel electrophoresis of the 5' RACE products were visualized on a 2% agarose gel stained with ethidium bromide, primary PCR (1°), nested PCR (2°).
Figure 5B:
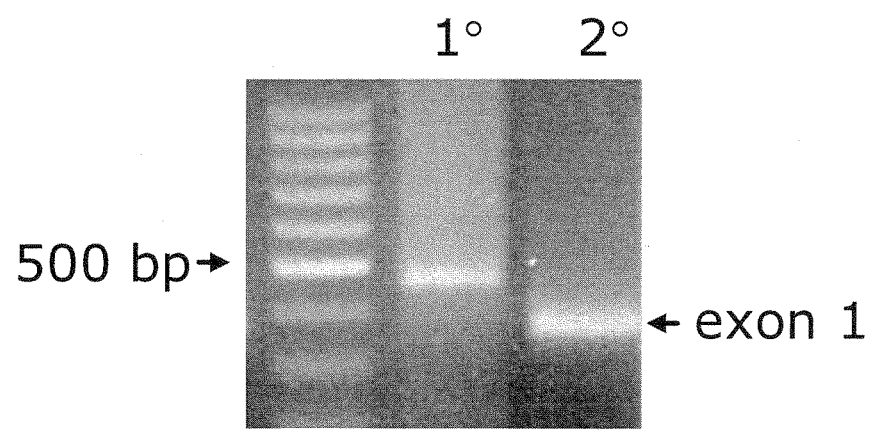
Figure 8:
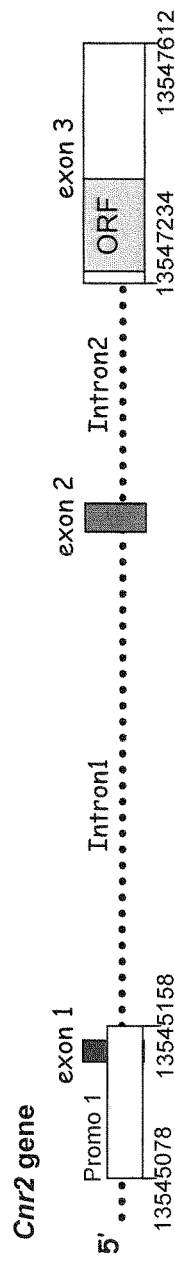
FIG. 8 is an illustration of the structure of $CB_2$ gene in B cells showing promoter 1, exons 2 and 3 (with ORF, protein coding region), and introns 1 and 2. Based upon GenBank, the $CB_2$ gene in mouse contains 3 exons that are arranged in linear fashion on chromosome 4. Exons 1 and 2 are separated from exon 3 by 2 introns that are spliced out during processing of the primary RNA transcript. From this limited information, it is believed that mouse cells transcribe at least 2 RNA transcripts but the structures of the promoters for these transcripts are not known in immune cells in general and specifically in B cells. The gene promoter according to an aspect of the invention is termed promoter 1 and represents 809 nucleotide base pairs of DNA located on chromosome 4 and positioned 5' at intron 1 and upstream of exon 2, intron 2, and exon 3 (the $CB_2$ open reading frame, ORF) (see model of gene in FIG. 8).

To determine the location of the mCnr2 TSS in purified B cells, the SMART 5' RACE technique was employed. FIGS. 5A-5B show RACE results of RNA isolated from mouse and human B cells. For mouse cells, the GSP1, $mCB_2$-R301, was used along with the UPM primer supplied with the kit. RACE PCR yielded three $mCB_2$ transcripts that were confirmed as $CB_2$ RACE products by nested PCR (FIG. 5A). RACE was also performed on human B cell RNA using the $hCB_2$-R298 GSP1 with the UPM, followed by nested PCR using $hCB_2$-R163 GSP2, resulting in the demonstration of only one transcript (FIG. 5B). In order to determine the relative gene location of the TSSs and 5'UTR structure of the $CB_2$ transcripts in B cells, the RACE products were isolated, sequenced and the nucleotides aligned for analysis. The location of the TSS was revealed by alignment of the 5' end of the RACE sequences with the UPM-SII oligo primer sequence and genomic DNA (FIG. 6). Furthermore, alignment of the sequenced RACE products to either the mouse or human genome, along with the GenBank submitted mRNA sequences revealed several new aspects of $CB_2$ transcript expression in B cells. First, the mouse transcripts were homologous to the Cnr2 as well as the existing $CB_2$ mRNA data, with the exception that exons 1 and 2 in the transcripts that were isolated were longer by 14 to 294 nucleotides, respectively, indicating they contained previously unidentified TSSs. Mouse B cells also expressed an additional transcript, exon 1b, with three TSSs (FIG. 9). Regarding transcript usage in human B cells, data obtained from three human subjects showed expression of only one first exon (FIG. 10). This is believed to be the first report identifying TSSs in B cells from mouse and human and these sequences have been submitted to GenBank (accession nos. FJ357033-6).

Figure 12B:
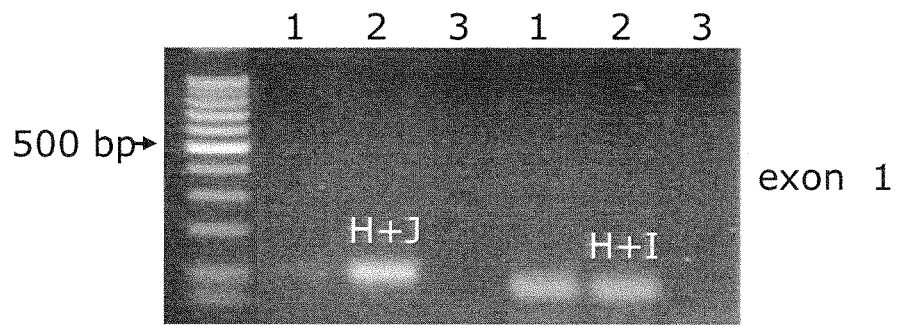

To verify the relative location of the TSSs, the present designed specific forward primers for PCR of either genomic DNA or cDNA reverse transcribed from 1 μg of total RNA. The strategy for these experiments is illustrated in FIGS. 11A and 12A. In brief, the forward primers were designed so that either the 3' or 5' end borders the TSS. Consequently, the forward primer in which the 3' end is adjacent to the TSS will only amplify genomic DNA and not the cDNA derived from the mRNA transcripts, whereas the forward primer that adjoins the TSS at the 5' end will amplify both genomic DNA and cDNA. There is some limitation with this approach in that it is not as sensitive as 5' RACE in determining the TSS, but it does help confirm the relative location of the TSS and approximate 5' end of the transcripts. Therefore, using this approach, the present inventors were able to confirm the TSS location of $mCB_2$ exons 1b and 2 (FIG. 11B), as well as the $hCB_2$ exon 1 transcript (FIG. 12B). Another limitation with the assay was that mouse exons 1a and 1b share identical sequences with the exception that exon 1b is 280 nucleotides longer at the 5' end. Consequently, primers designed to adjoin the TSS of exon 1a would not be able to distinguish genomic DNA from cDNA derived from exon 1b and would amplify both. Therefore, this approach could not be used to verify the location of the TSS for transcripts containing exon 1a in B cells.

EXAMPLE 4

Preferential Usage of the CB2 Exon 1a Transcript Variant in Resting Spenic B Cells The 5' RACE data revealed that resting splenic B cells expressed several $CB_2$ transcripts. Therefore, in order to determine which transcript was most abundant, THE INVENTORS used RT-PCR to quantify the transcripts. Using exon specific primers, semi-quantitative RT-PCR showed exon 3-containing transcripts and those containing variants of exon 1 rather than exon 2 predominated in resting B cells (FIG. 13A). To better define these results, the inventors used quantitative real time RT-PCR (RT-qPCR). The primers and $CB_2$ exon specific taqman sequences, listed in Table 3 and located as black boxes in the diagram of FIG. 13, were used in conjunction with β-actin primers and taqman probe in a duplex RT-qPCR. Since all three transcripts include exon 3, primers designed for this exon will amplify all the transcripts regardless of the first exon. In addition, primers designed for exon 1a should amplify all transcripts containing exon 1, whereas primers for exon 1b and 2 were designed to specifically amplify transcripts containing only these exons. The results show that the exon 1a transcript variant was the most abundantly expressed transcript in un-stimulated resting splenic B cells (FIG. 13B).

EXAMPLE 5

Bioinformatics Analysis for Core Promoter Elements Near the TSSs

It has been well established that identification of the TSS will lead to the location of the core promoter, which is usually −40 bp upstream to +40 bp downstream of the TSS. The basic elements that comprise the core promoter are the TATA-box, INR (Initiator), DPE (downstream promoter element), and BRE (TFIIB recognition elements) (Sandelin, A. et al., Nature Reviews, 2007, 8:424-436). Therefore, the inventors performed a bioinformatics analysis for the presence of consensus sequence of the core promoter elements in the vicinity of the RACE TSSs to tentatively identify the structure and location of the Cnr2 core promoter. Using GCG SeqWeb, the inventors aligned the 5' ends of the RACE sequences with that of previously described $CB_2$ mRNA sequences (GenBank accession nos. NM009924 for mouse, and NM001841 for human) as well as the Cnr2 genomic region spanning −45 bp to +50 bp of the RACE TSSs (positions +1, FIG. 13A-B), followed by in silico analysis for core element consensus sequences. For exon 1a, the inventors identified an INR sequence spanning the area −2 bp to +5 bp surrounding the TSS (+1), a TATA-like sequence at position −25 hp as well as multiple DPEs and DCEs at positions +10, 18, 31, 36, 38, and +44 bp. The RACE results for the exon 1b transcript identified 3 TSSs, which from this analysis appear to have INR-like sequences. In addition, a GC/GAGA-box spanning 24 bp is present that is −24, −25, −26 bp as well as multiple DPE sites at +30, 33, 29, and +35 bp from its respective TSS. The exon 2 RACE transcript has an INR-like sequence, a TATA-box at −21 bp as well as DCE at +11 bp and a DPE at +25 bp (FIG. 14A). The RACE transcripts from human also contain an INR-like sequence, as well as a TATA-box at −31 bp, a $BRE^d$- 24 bp and a DPE at +35 bp (FIG. 14B). From this analysis it appears that the consensus sequences for core promoter elements are in the vicinity of the TSSs identified by the 5' RACE experiments. Furthermore, the analysis suggested that mCnr2 has three potential core promoters for the pre-initiation complex to assemble for transcription initiation, whereas hCNR2 has a single putative core promoter.

EXAMPLE 6

Bioinformatics Analysis to Identify Putative Promoters and Cis-Sequences

It is well accepted that the promoter has two interacting components; the core promoter, in which the basic transcription factors join with Pol II at the TSS to form the pre-initiation complex and the regulatory elements that are involved in activated transcription (Yarden, G. et al., Nucleic Acids Research, 2009, 37:4234-4246). These regulatory elements include proximal elements, next to the core promoter, and enhancers/repressors elements, which can be located several kbs upstream or downstream the TSS. These regulatory elements, known as cis-sequences are the DNA binding sites for transcription factors. Identifying the Cnr2 promoter and cis-sequences will provide insight into how this gene is regulated in B cells during different states of activation.

Bioinformatics has become a useful tool in identifying sequences that may be involved in regulating gene transcription that can then be experimentally tested. Therefore, to increase the understanding of the functional regulatory regions that control $CB_2$ transcription the inventors utilized several web-base programs to tentatively locate the Cnr2 promoter and cis-sequences. Functional regulatory regions tend to be close to the TSS; therefore, the first analysis was to locate putative promoters near our 5' RACE TSSs. To accomplish this, the present inventors used the Genomatix suite to analyze 1 kb of the Cnr2 genomic sequence (obtain from GenBank) surrounding the TSSs for exons 1 and 2. The analysis yielded two predicted promoter regions for the mCnr2 and one for the hCNR2. The first mCnr2 predicted promoter is 690 bp and spans the region −574 bp to +115 bp from the $mCB_2$ exon 1a TSS (+1). The second mCnr2 promoter is 601 bp and spans −362 bp to +238 bp from the $mCB_2$ exon 2 TSS (+1). The single hCNR2 predicted promoter is 601 bp spanning −406 bp to +135 bp of the TSS (+1).

To identify putative cis-sequences, the present inventors used the same 1 kb genomic regions as above and the MatInspector program of the Genomatix suite, which this analysis yielded numerous cis-sequences that hampered us to decipher the true positives from the false. Therefore, the inventors used the process of phylogenetic footprinting, in which ClustalW was used to align the entire Cnr2 gene of mouse and human to find conserved regulatory regions. Alignment of the orthologous genes paralleled the Genomatix promoter prediction for the exon 1 region (FIG. 15A). In addition, the orthologous alignment of the genomic region near the mouse exon 2 showed high conservation between mouse and human suggesting the possibility of an exon 2 for human CNR2, which the Genomatix analysis did not reveal (FIG. 15B). Exon 1 and 2 regions were further analyzed using the Consite web-base program for conserved cis-sequence regions. The exon 1 alignment revealed conserved cis-sequences for Elk-1 and c-REL, as well as DNA binding sites for STAT6 and NF-kBp50 for mouse, GATA and STAT for human. Similar results were obtained for the exon 2 alignment indicating a conserved NF-kB, p65, c-REL cis-sequence and single STAT6 DNA binding sites for both mouse and human (FIG.

15A-15B). The results obtained from these analyses exemplified the usefulness of employing bioinformatics as a tool to direct research in locating candidate Cnr2 gene regulatory regions that can then be experimentally tested for functionality, as well as guide future research in understanding the interplay between the cis-sequences and trans-factors that regulate Cnr2 in B cells.

EXAMPLE 7

Cloning of the Putative Cnr2 Promoters

Figure 16A:
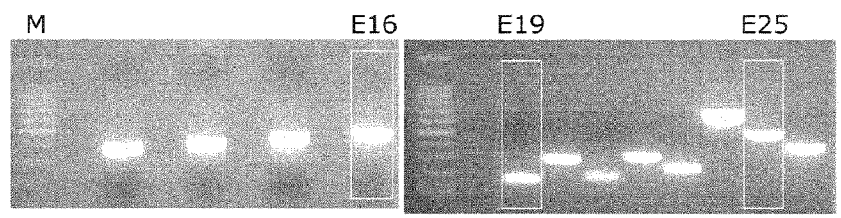
FIGS. 16A-16C shows cloning of the Exon 1 Promoter.
Figure 16B:
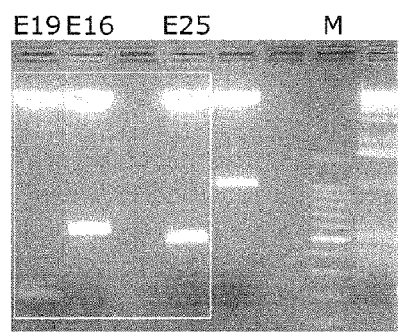
Figure 16C:
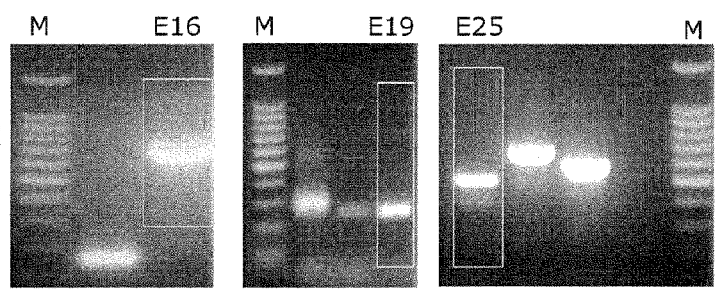

From the bioinformatics analysis, the regions surrounding the TSSs for mouse exons 1 and 2 appeared to have core promoter elements, as well as enhancer elements; therefore, the inventors wanted to evaluate these regions for promoter activity. To test for promoter activity, the inventors used genomic DNA from purified B cells to PCR amplify select regions of exon 1 (FIG. 16A) spanning −359 bp to +205 bp of exon 1a TSS (+1) as well as the region from −189 bp to +205 bp of exon 2 TSS (+1). During PCR amplification, the Taq polymerase adds an adenosine nucleotide at the end of elongation thereby creating an A-tail that can be easily cloned into a TA-cloning vector, such as the TOPO-blue vector. Therefore, the PCR amplified DNA fragments were gel purified and initially TA-cloned into the TOPO-blue vector then subcloned into the pGL3-enhancer vector via the Hind III site by standard methods (FIG. 16B). PCR screening was performed to determine insertion of the Cnr2 clones into the pGL3-enhancer vector (FIG. 16C). In total, three exon 1; pGL3-E16 (−270, +205), E19(+68, +205), and E25(−359, +63) as well as five exon 2; pGL3-P7(−189, +36), P8(−90, +36), P10(+13, +205), P11(−189, +101), and P13(−25, +101) experimental Cnr2 clones were chosen for evaluation of promoter activity.

EXAMPLE 8

Determination of Cnr2 Promomter Activity in B Cells

Figure 22A:
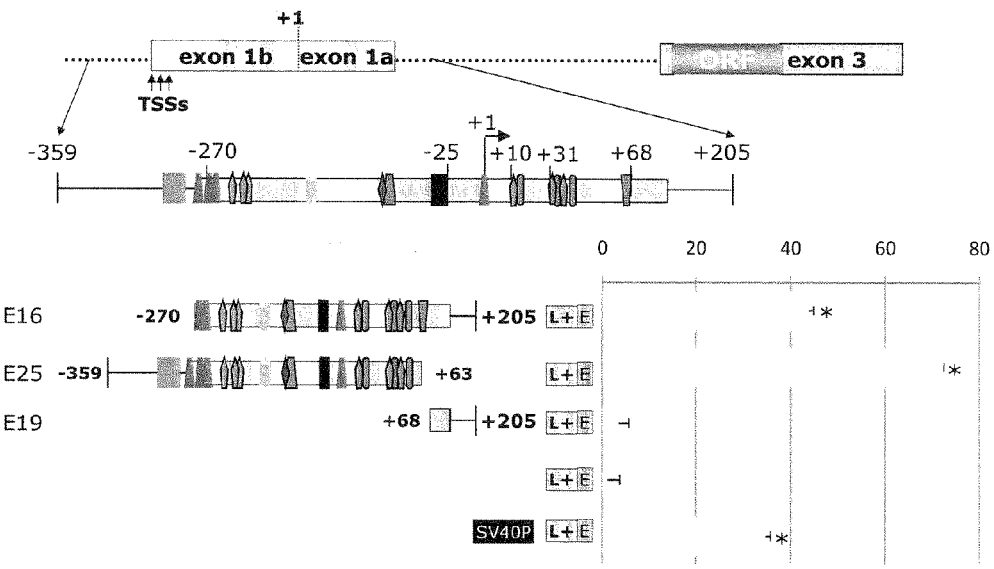
FIGS. 22A and 22B show pGL3-Cnr2 luciferase activity in IL-4/anti-CD40 activated B cells.

The pGL3-Cnr2 constructs were transfected by electroporation into IL-4/anti-CD40 stimulated primary B cells and 24 hrs later luciferase activity was determined for each construct. For exon 1 five constructs were analyzed, two control and three experimental vectors. The pGL3-enhancer vector does not have a promoter and contains only the SV40 enhancer downstream of the luciferase gene and therefore served as baseline activity. The pGL3-control vector contains both the SV40 promoter and enhancer and therefore exhibits full promoter activity. The pGL3-E25 experimental vector spans the region −359 bp to +63 bp (exon 1a, TSS+1) and contains all the TSSs and core promoter elements for exons 1a and 1b. The pGL3-E16 experimental vector spanning −270 bp to +205 bp contains the core promoter of exon 1a and a portion of the exon 1b core promoter. The GAGA-box and 1 TSS at −280 bp were excluded. The pGL3-E19 experimental vector spans from +68 bp to +205 bp and therefore did not contain either the exon 1a or exon 1b TSSs and core promoter cis-elements. Luciferase activation analysis for the exon 1 putative promoter demonstrated significant promoter activity for the pGL3-E25(−359, +63), pGL3-E16(−270, +205) and pGL3-control vectors, but not for pGL3-E19(+68, +205), indicating that the RACE TSSs that were identified were in Cnr2 genomic regions that exhibited characteristics of a gene promoter (FIG. 22A). In addition, pGL3-E25 had greater promoter activity then pGL3-E16 indicating that the GAGA-box and possibly the TSS at −280 bp are important for full promoter activity under these conditions.

Figure 22B:
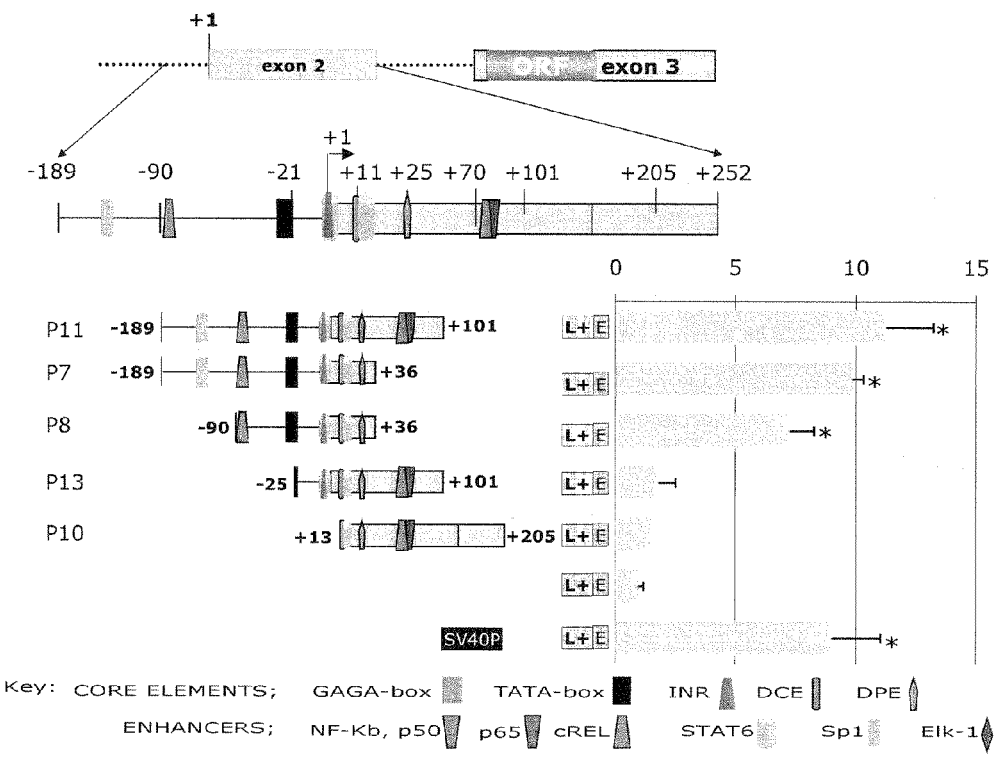
Figure 23:
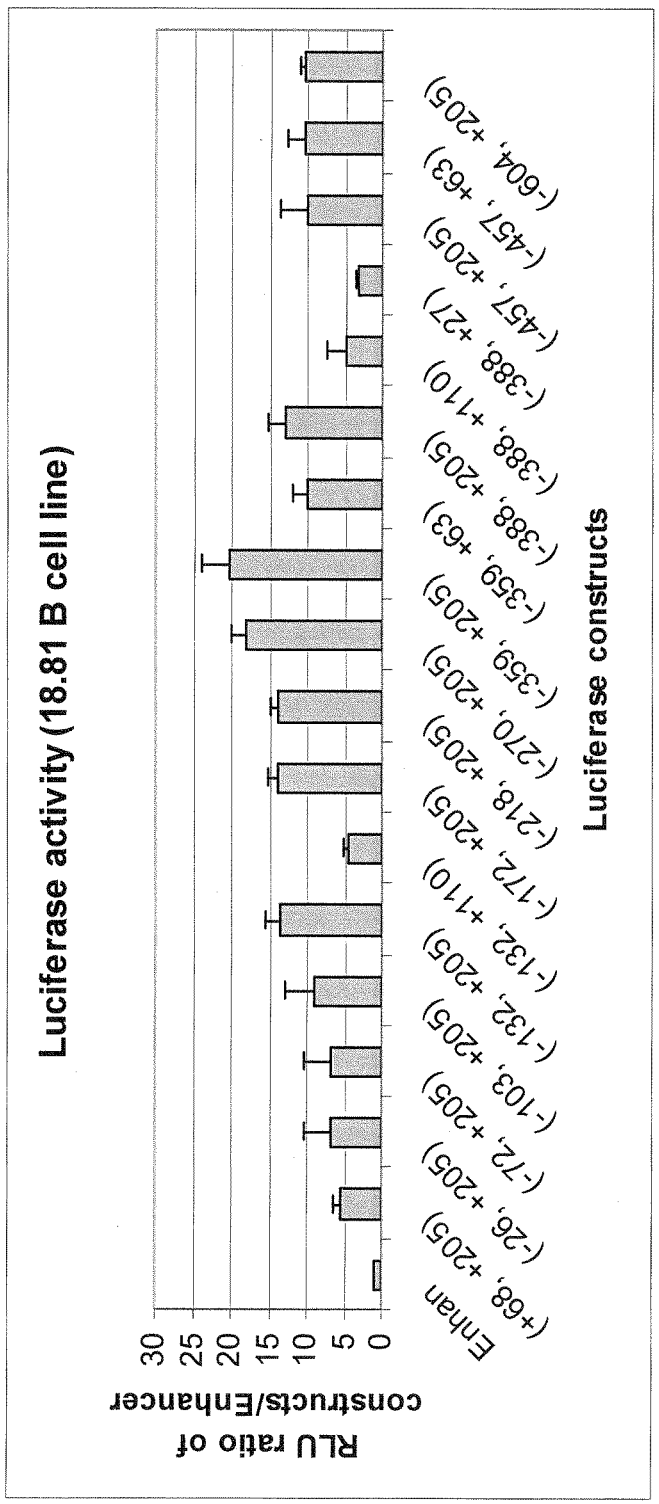
FIG. 23 shows $CB_2$ gene promoter activity measured in the B cell line, 18.81, for various chromosome segments ranging from the shortest (+66, +205) to the longest (−604, +205). The promoter activity is expressed as the ratio of chromosome segment RLUs to the RLU activity of the enhancer only (Enhan) vector. The gene promoter activity of a chromosome segment can be determined by inserting the segment of putative promoter into a so-called Reporter Vector and then inserting the vector into a relevant cell type. 17 different DNA fragments of the putative promoter segment of the $CB_2$ gene were isolated and inserted these into the pGL3 Luciferase Promoter Vector (Promega Corporation, Madison, Wis. 73711). These different Vectors were then inserted (transfected) into the 18.81 mouse B cell line and tested for gene promoter activity by assaying the activity of the read-out gene product, luciferase (FIG. 23). The activity of the luciferase is expressed in relative light units (RLUs) normalized to the control vector construct containing only a gene enhancer sequence (see Enhan bar in FIG. 23). From FIG. 23, it can be seen that the highest gene promoter activity is associated with fragment −359 to +205. Lengthening or shortening this fragment lessens the promoter activity; however, fragment −604 to +205 still has very good promoter activity and is therefore identified as the sequence encompassing the gene promoter.

The five exon 2 experimental clones used to evaluate promoter activity were pGL3-P11, which spans the genomic region −189 bp to +101 bp (exon 2, TSS+1) and contained the core and enhancer cis-elements. The truncated pGL3-P7 spanned −189 bp to +36 bp, was designed to exclude the 3' NF-kBp65, cREL cis-elements yet contained the core and 5' enhancer cis-elements. The pGL3-P8 was further truncated at the 5' end to span −90 bp to +36 bp and contained only core promoter cis-elements along with the 5' cREL enhancer cis-element. The pGL3-P13(−25, +101) truncated at the 5' end to include a third of the TATA-box and 3' core and enhancer cis-elements. The pGL3-P10(+13, +205) clone truncated at the 5' end to exclude the TATA-box and INR core cis-elements, but extended at the 3' end to include a portion of the GenBank designated exon 2 sequence. The reporter assay for the exon 2 clones demonstrated that the core promoter vector pGL3-P8 was sufficient to produce significant promoter activity. However, increased promoter activity was seen with the pGL3-P7 clone, which contained the 5' Sp1 cis-element as well as the pGL3-P11 clone that contained the 5' Sp1 and the 3' NF-kBp65, cREL cis-elements. No significant promoter activity was observed for either the pGL3-P10 or -P13 clones demonstrating that the TATA-box as well as the INR are needed for full promoter activity (FIG. 22B). In all, these results demonstrated that the Cnr2 genomic region containing the TSSs as well as core promoter cis-elements for exons 1a, 1b and 2 contained strong promoter activity as judged by these luciferase expression studies.

EXAMPLE 9

CB2 Transcript Expression in Mouse Activated B Cells

Since $CB_2$ is abundant in B cells and implicated in the involvement of various B cell functions, an understanding of transcript usage under varying conditions of B cell activation is of interest. The literature shows that stimulation of B cells with anti-CD40 and/or IL-4, through STAT6 (cis-sequence found in both $CB_2$ putative promoter regions) activation, increases $CB_2$ expression (Carayon, P. et al., Blood, 1998, 92:3605-3615; Lee, S. F. et al., Eur. J. Pharmacol., 2001, 423:235-241; Schroder, A. J. et al., J Immunol, 2002, 168: 996-1000), whereas, LPS stimulation suppresses expression (Lee, S. F. et al., Advances in Experimental Medicine and Biology, 2001, 493:223-228). LPS through TLR4 triggers an intracellular signaling cascade, similar to anti-CD40/CD40 binding, that activates the trans-regulatory factors Elk1 and NF-kB (found in the $CB_2$ putative promoters). Both IL4/anti-CD40 and LPS promote B cell maturation and isotype switching.

Figure 25A:
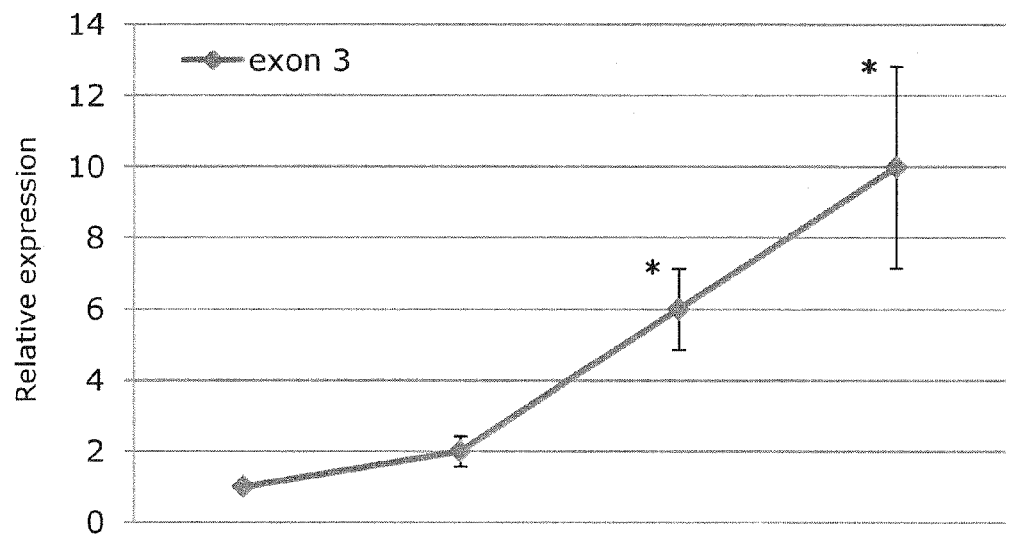
FIGS. 25A and 25B show that LPS induces the expression of the mouse $CB_2$ exon 1b and 2 transcripts in primary B cells. Primary B cells were cultured for 1, 3, and 8 hrs in RPMI medium containing 5 µg/ml LPS. Total RNA was isolated and 1 µg was used for RT-qPCR. Total $CB_2$ message expression (exon 3) increases over time with LPS stimulation, as shown in FIG. 25A. Exon 1b and 2 transcripts expression is significantly increased overtime whereas the exon 1a transcript remains at baseline, as shown in FIG. 25B. Results were obtained by the $2^{-\Delta\Delta CT}$ method in which β-actin is the endogenous control and un-stimulated B cells (time 0) as the calibrator. Data are means±S.E.M. of three independent experiments. * Significance at P=0.05
Figure 25B:
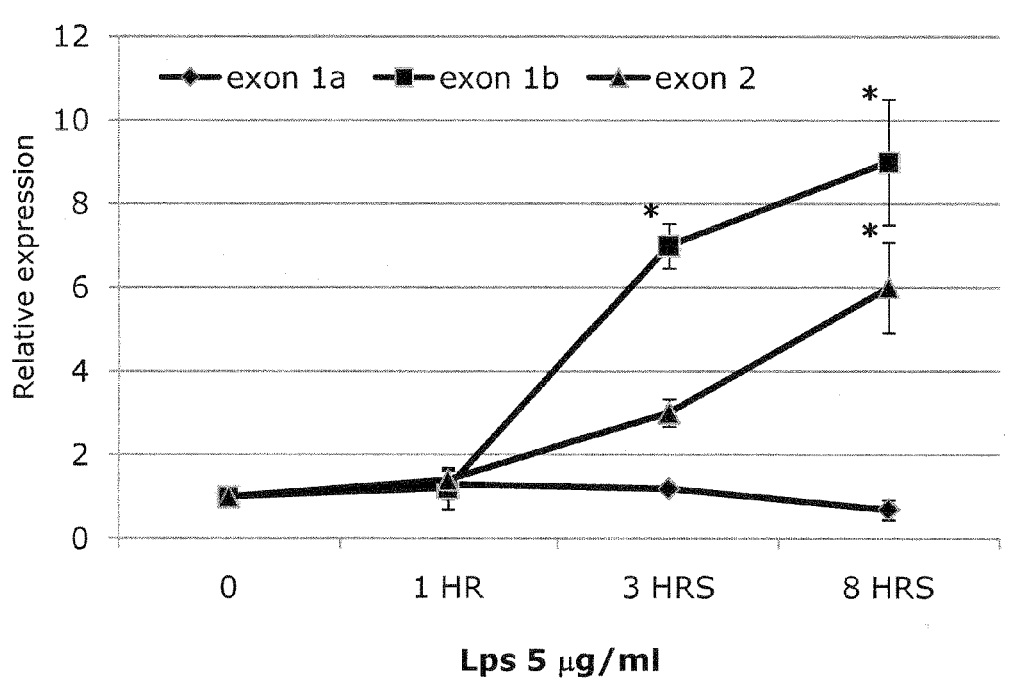

Therefore, to gain a better understanding of $CB_2$ transcript usage in activated B cells, the inventors stimulated primary B cells with either LPS or the co-stimulatory molecule anti-CD40. To determine the relative expression of the $CB_2$ transcript variants, total RNA was collected at 1, 3, and 8 hrs following stimulation for RT-qPCR analysis. We looked at the expression of the $CB_2$ coding exon (exon 3, FIG. 25A) and observed a steady increase over time following LPS stimulation. Furthermore, using exon-specific primers and taqman probes revealed that LPS induced significant expression of the non-coding exon 1b and 2 transcripts, whereas, the exon 1a transcript remained at baseline (FIG. 25B).

B cells activated by IL-4 and anti-CD40 undergo class switch recombination (CSR) changing the C region of the H chain to switch from IgM to IgE. The present inventors' lab has previously shown that IL4/anti-CD40 stimulation increased $CB_2$ expression in B cells at the message (Lee, S. F. et al., *Eur. J. Pharmacol.*, 2001, 423:235-241) and protein level (Agudelo, M. et al., *Journal of Neuroimmune Pharmacology*, 2008, 3:35-42). In addition to this, the inventors' lab has also shown that co-treatment of the IL-4/anti-CD40 stimulated B cells with the CBR agonist CP55940 increased immunoglobulin class switching to IgE.

Figure 26A:
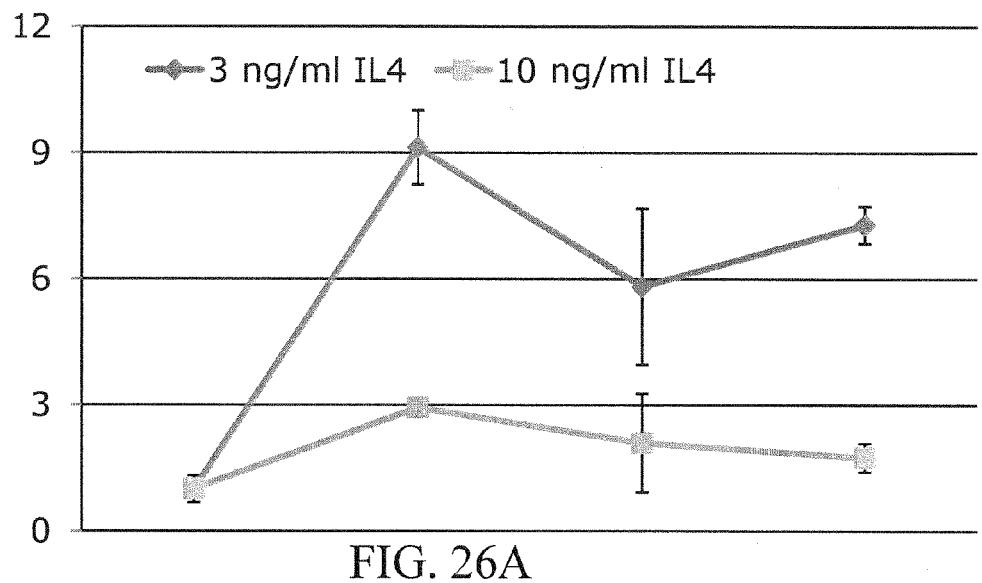
FIGS. 26A and 26B show results of stimulation of mouse primary B cells with IL-4 and anti-CD40. Mouse primary B cells were cultured for 1, 3, and 8 hrs in RPMI medium containing IL-4 and 500 ng/ml anti-CD40. Total RNA was isolated and 1 µg was used for RT-qPCR. Total $CB_2$ expression (exon 3) significantly increases with 3 ng/ml compared to 10 ng/ml IL-4 and 500 ng/ml anti-CD40, as shown in FIG. 26A. The exon 2 transcript steadily increases with stimulation of 3 ng/ml IL-4, as shown in FIG. 26B.
Figure 26B:
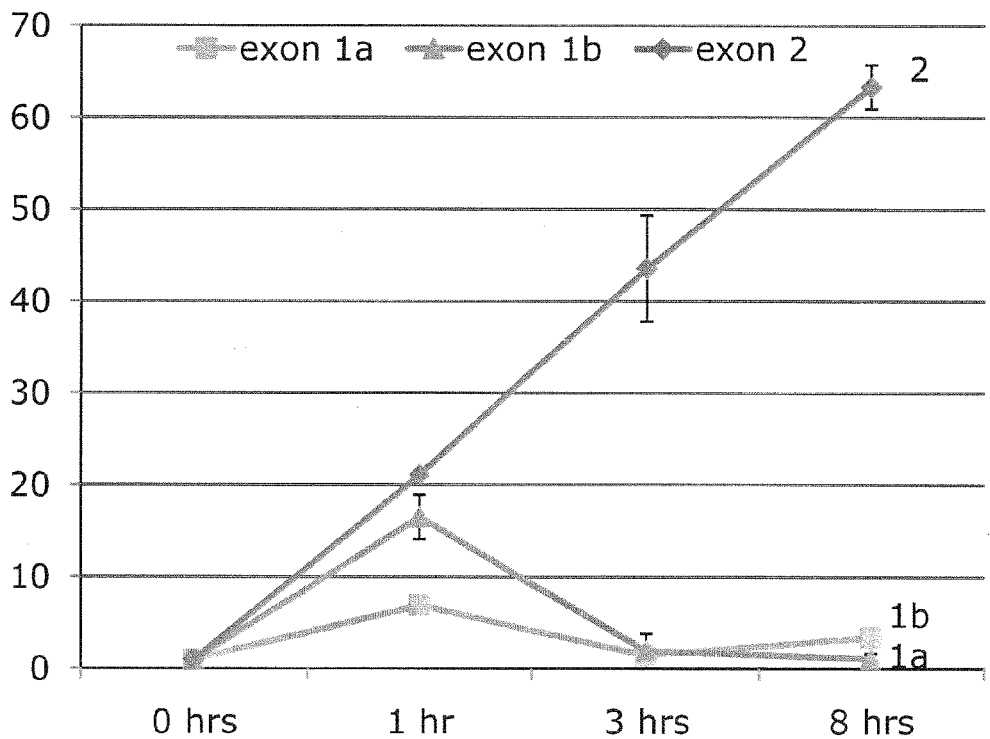

To determine the effective dose of IL-4, the inventors initially looked at $CB_2$ the coding exon 3 expression using two concentrations of IL-4 (3 and 10 ng/ml) with anti-CD40 (0.5 µg/ml). Exon 3 expression was significantly higher in B cells stimulated with 3 ng/ml of IL-4 compared to B cells stimulated with 10 ng/ml (FIG. 26A). Therefore, the inventors used the 3 ng/ml concentration of IL-4 with anti-CD40 to investigate $CB_2$ transcript variant expression. Following stimulation exon 3 increased within the first hour and maintained a steady state of expression thereafter (FIG. 26A). On the other hand, non-coding exon expression increased increased 1 hr following stimulation with exon 2 continuing to increase over time, while the exons 1a and 1b returned to baseline by three hrs post stimulation (FIG. 26B). These results demonstrated for the first time that $CB_2$ transcript usage differs in B cells depending upon the state of activation of the cell with exon 1a predominating under basal conditions and exons 1b and 2 under varying conditions of activation.

EXAMPLE 10

CB2 Transcript Expression in Immune Cell Subtypes

Figure 27A:
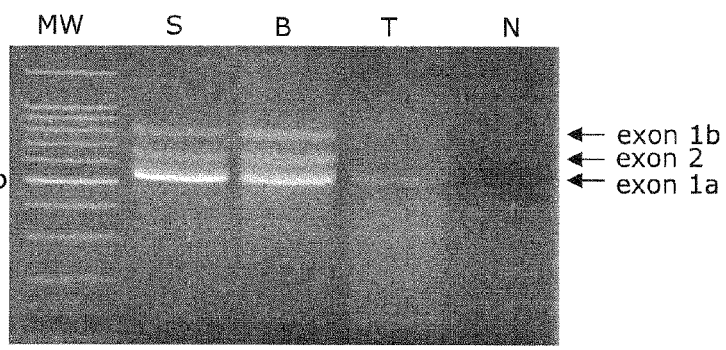
FIGS. 27A and 27B show results of gel electrophoresis of the 5' RACE mouse $CB_2$ transcripts isolated from immune cell subtypes, including splenocytes, B cells, and T cells (FIG. 27A), and dendritic cells and macrophages (FIG. 27B).
Figure 27B:
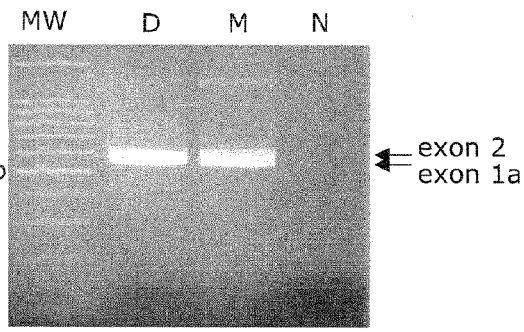
Figure 28A:
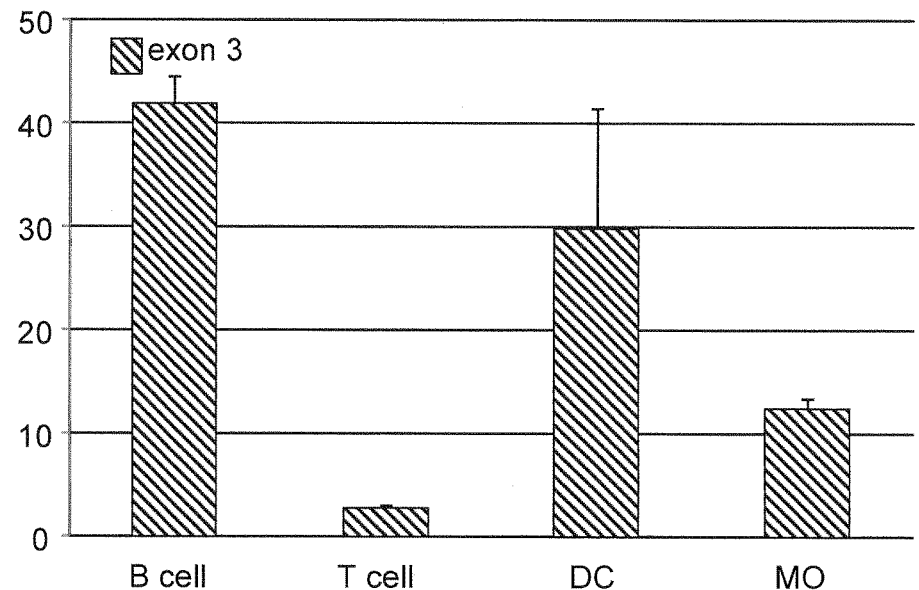
FIGS. 28A and 28B show results of quantitative RT-qPCR of the $CB_2$ Transcripts in Immune Cell Subtypes. Using 1 µg of total RNA isolated from un-stimulated B cells, T cells, Dendritic cells (DC) and macrophages (Mo) $CB_2$ transcript usage was determined. Total $CB_2$ expression (exon 3) in the immune cell subtypes is shown in FIG. 28A. $CB_2$ transcript expression in the immune cell subtypes is shown in FIG. 28B.
Figure 28B:
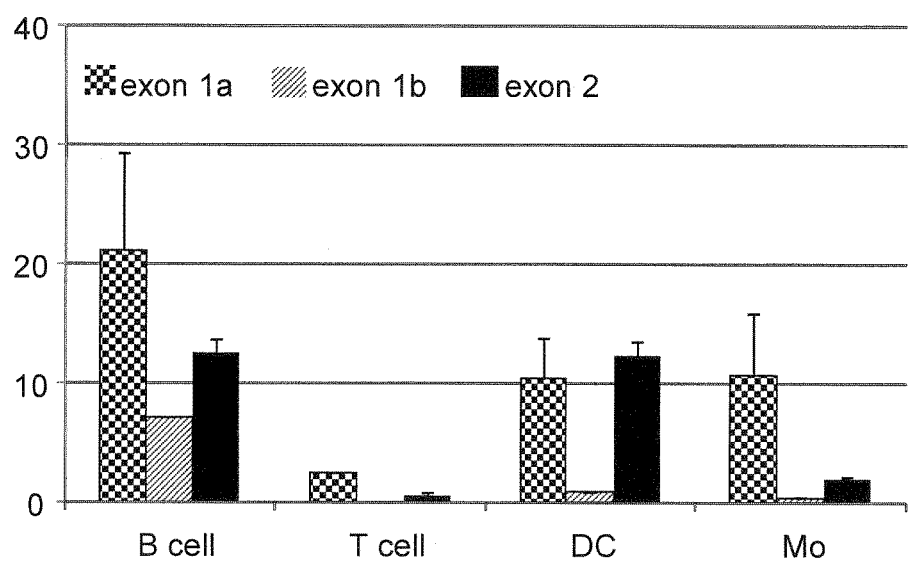

The bioinformatics analysis performed in Aim 1 of the GenBank $CB_2$ clones suggested that expression of the first 5'UTR exon (1 and 2) variants could be related to tissue or cell type, the clones of immune tissue expressed exon 1, and other tissue types expressed exon 2. In spite of this, 5' RACE showed that B cells expressed $CB_2$ transcripts containing two variants of exon 1 and a single exon 2 variant. Since the previously described GenBank clones were obtained from immune tissues, and provided no information on transcript expression in immune cell subtypes, the inventors wanted to investigate $CB_2$ expression in other immune cells other than B cells. Total RNA was isolated from purified un-stimulated T cells, dendritic cells, and macrophages for 5' RACE analysis. The results showed that $CB_2$ transcript expression was unique to immune cell subtypes. For example, T cells expressed only the exon 1a variant, whereas dendritic cells and macrophages expressed two transcript variants (exon 1a and 2). Most interesting was that the exon 1b variant was only observed in B cells (FIG. 27 A-B). To confirm the expression of the transcript variants in the immune cell subtypes, RT-qPCR using exon specific primers and taqman probes was done (FIG. 28A-B). Coding exon 3 transcript expression was highest in B cells, followed by dendritic cells, then macrophages and T cells expressing the least (FIG. 28A). The exon 1a variant was the major $CB_2$ transcript seen in T cells. Dendritic cells and macrophages expressed both the exon 1a and 2 variants, however the relative expression of exon 2 was much higher in the dendritic cells (FIG. 28B). The expression of the exon 1b variant was exclusive to B cells, though a negligible amount was observed in dendritic cells, which could be from amplification of residual genomic DNA. These results showed for the first time that the $CB_2$ transcript expression profile is different among the immune cell subtypes and that variant expression could be related to cell type and/or cell function. In addition, among these immune cell subtypes, the exon 1b variant was observed only in B cells and, therefore, could potentially be a cell specific target for $CB_2$ expression in this cell type.

EXAMPLE 11

$CB_2$ Transcript Expression in Development of B Cells

In A recent study investigating $CB_2$ mediation of immature B cell retention in bone marrow sinusoids (Pereira, J. P. et al., *Nature Immunology*, 2009, 10:403-411) showed a two-fold higher expression of $CB_2$ in immature B cells compared to pre-B cells and that $CB_2$ deficiency led to a lower frequency of the Ig light-chain ($\lambda^+$) immature and mature B cells in the blood and spleen, thus suggesting a role for $CB_2$ in the formation of the B cell repertoire. In addition, the results above have shown that expression of the $CB_2$ transcript variants can be related to immune cell subtype as well as the activation state of B cells. Therefore, the present inventors investigated $CB_2$ transcript expression in three different B cell lines representing B cell development from the pre-B stage to the mature stage.

Figure 29A:
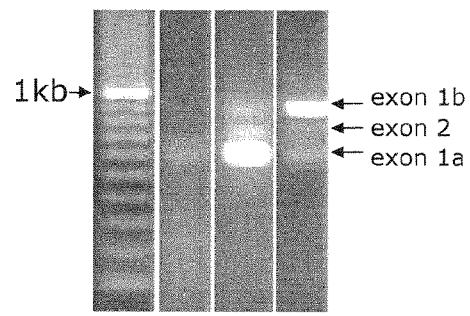
FIGS. 29A-29C show results of mouse $CB_2$ transcript expression in B Cell Lines.
Figure 29B:
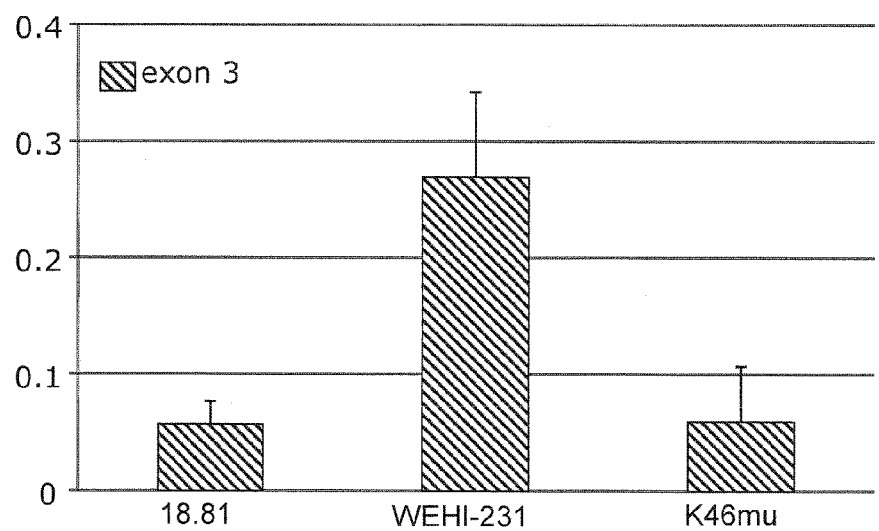
Figure 29C:
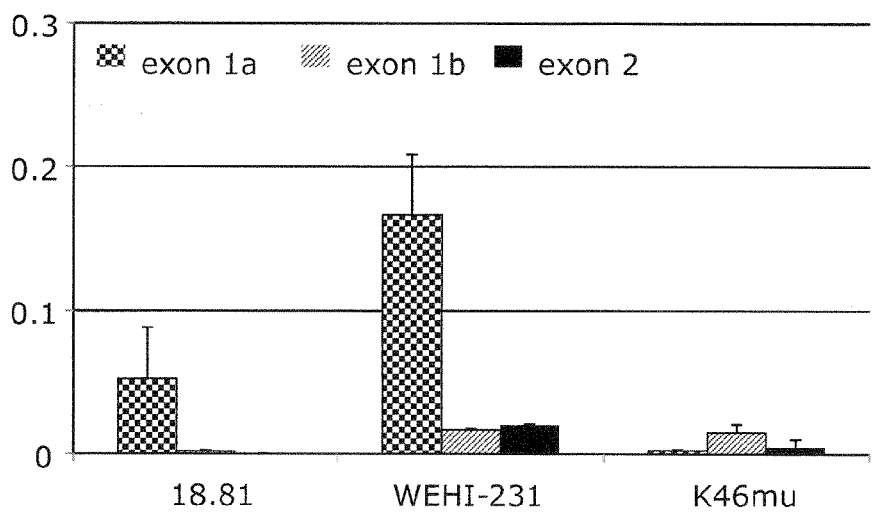

The three mouse B cell lines used were; 18.81, an Abelson virus-transformed pre-B cell line that synthesizes only H chain, no light chain is produced. WEHI-231, an immature B lymphoma cell line that lacks Fc receptors and expresses only surface IgM and not IgD. K46µ, a mature B lymphoma cell line that expresses surface IgM and IgD. The 5' RACE of the different cell lines showed that the pre-B cell line expressed the exon 1a transcript and that the immature B cell line WEHI-231 and the mature B cell Line K46µ express all three transcripts but at different levels (FIG. 29A). Therefore, we performed RT-qPCR to determine the predominant $CB_2$ transcript expressed in these B cell lines. $CB_2$ coding exon 3 was observed to be the highest in WEHI-231 (immature) and lower in 18.81 and K46µ. The predominant $CB_2$ transcript observed in 18.81 and WEHI-231 was the exon 1a transcript, whereas the exon 1b transcript was predominant in the mature K46µ B cell line (FIG. 29B). The data suggested that expression of the $CB_2$ transcript variants could be related to the developmental stage of B cells. In addition these results further support that $CB_2$ transcript usage varies in response to changes in B cell biology.

The relative robust expression of $CB_2$ in human and mouse B cells suggests that this receptor may have an important role in B cell biology. However, only a few reports have investigated the function of $CB_2$ in B cells. Furthermore, examination of the $CB_2$ transcript expression and Cnr2 regulatory elements (i.e., promoter and TSS) in B cells had not been reported. Therefore, the inventors investigated the genomic sequences involved in transcription of $CB_2$ by identifying the TSSs, mRNA transcripts and core promoter regions in purified resting and activated mouse B cells.

The data disclosed herein provides the first evidence that resting splenic B cells in mice use multiple TSSs and express at least three $CB_2$ transcript variants. Based on present models of transcription initiation it is possible that two mechanisms of transcription could be involved in the generation of these variants: 1) alternative splicing of the 5'UTRs in the case of exons 1 or 2, and in fact donor-acceptor sites occur in these regions; and 2) alternative transcription initiation (dispersed initiation, see below) generating exon 1 variants that differ in the length of their 5' ends. The latter event may have occurred in the case of exon 1 in that different lengths of the 5' ends were observed ranging over 295 bps and containing a cluster of four TSSs. Interestingly, a cluster of TSSs was predicted by the database, DBTSS, in the 5' flanking regions of exons 1 and 2; furthermore, multiple TSSs were reported in GenBank $CB_2$ clones from various tissues in these same regions. The RACE products from B cells identified new TSSs for exons 1 and 2 that were not only different than reported in other tissues but for the most part longer at the 5' ends. Because of these many TSSs spread over hundreds of bps, the inventors analyzed for core promoter sequences in these areas using an in silico approach. Interestingly, the present inventors found consensus core promoter sequences such as INR, DPE, DCE along with either TATA or GC boxes in abundance and in proximity to all of the TSSs expressed in mouse and the one TSS expressed in human B cells (see FIGS. 14A-B). However, although present, these sequences were in different numbers and relative distances to the TSS position suggesting heterogeneity in core promoter activity under resting and activated conditions. Although the functional significance of multiple TSSs and core promoters is unknown, previous studies suggested this heterogeneity relates to cell type and/or cell activation state. This was observed in studies on the control of alternative first exons of the glucocorticoid receptor (GR) which are under the control of specific transcription factors that control both tissue specific and cell activation state specific GR expression (Turner, J. D. et al., Biochem Pharmacol., 2006, 72(11):1529-1537). This was also observed with adenosine A2A receptor (A2AR) 5'UTR splice variants wherein the long 5'UTR A2AR variants were observed in resting PMNs, whereas the short 5'UTRs were expressed to a greater extent in LPS-stimulated cells suggesting short 5'UTR variants were more efficiently translated (Kreth, S. et al., FASEB Journal, 2008, 22:3276-3286) and suggesting the length of the 5' UTR can be a factor in determining tissue specificity and cell activation state.

In the mouse $CB_2$ studies described herein, different TSSs and transcript expression were observed in different cell types. For example, resting T cells expressed only the exon 1a variant (FIGS. 27A-B and 28A-B) and variants of this have been reported in thymocytes, splenocytes, and the macrophage like cell line, NFS107 (GenBank accession nos. AK037898, X86405, and NM009924). Whereas, bone and liver tissue (GenBank accession nos. BC024052 and AK036658) expressed the exon 2 variant though shorter at the 5' end than what was observed in B cells. Besides T cells, variation of $CB_2$ transcript expression was observed in other immune cell subtypes. For example, purified dendritic cells and macrophages expressed the exon 1a and 2 variants (FIGS. 27A-B), though in dendritic cells the expression of the two variants was more or less equal, whereas in macrophages the exon 1a variant was expressed five-fold higher than the exon 2 variant (FIGS. 28A-B). Furthermore, resting splenic B cells expressed 3 $CB_2$ transcripts with an expression rank order of exon 1a>exon 2>exon 1b, and of interest expression of the exon 1b variant was only observed in B cells (FIGS. 13A-B and 28A-B). This variation in transcript expression among the various subtypes may be accounted for by variations in core promoter activity surrounding the different TSSs.

In contrast to the multiple TSSs and transcript variants observed in mouse cells, human peripheral B cells collected from three different donors expressed a single $CB_2$ transcript and TSS (FIGS. 5A-B). Interestingly, the present inventors' observations in mouse and human are in line with those showing that two different strategies are employed by Pol II for transcription initiation. The hCNR2 appears to utilize the more common strategy termed "focused initiation" in which a single TSS and the core promoter contains a TATA-box, $BRE^d$, INR, and DPE. On the other hand, the mCnr2 is more like the second strategy that involves multiple weak TSSs dispersed over DNA regions of approximately 50 to 150 bps, thereby dubbed "dispersed initiation" (Juven-Gershon, T. et al., Biochemical Society Transactions, 2006, 34:1047-1050). The mechanisms of dispersed initiation are not clear but probably involve selective usage of multiple upstream and downstream recognition and promoter elements similar to what we observed surrounding the mouse TSSs.

Different $mCB_2$ transcripts are not only associated with different cell types but also with different cell activation states. Using RT-qPCR, the inventors showed that the mouse exon 1a transcript was predominantly expressed in resting splenic B cells (FIGS. 13A-B) but that exons 1b and 2 were more pronounced in the LPS-activated B cells (FIG. 25B), and that exon 2 increased in IL-4/anti-CD40 stimulated B cells (FIG. 26B). A possible explanation of the observed variation in $CB_2$ transcript expression is the presence of proximal regulatory cis-sequences to the transcript TSS. Because in addition to core promoter activity, cell activation can lead to gene transcription through enhancer elements on the DNA either 5' or 3' to the core promoter region (Birney, E. et al., Nature, 2007, 447:799-816). Interestingly, the in silica analysis performed in Aim 2 (Examples 5-8) identified proximal NF-kB (−82 and +72 bp) as well as STAT6 (−6 and +12 bp) cis-sequences 5' and 3' of the TSS(+1) for exon 2 (FIG. 15B), which may account for the observed increase expression of the exon 2 variant in B cells activated by LPS or IL-4/anti-CD40 since it is well known that LPS, IL-4 and anti-CD40 activate B cells through an increase in NF-kB (12, 44, 47) and with IL-4 through activation of STAT6. In addition, pGL3-Cnr2 reporter plasmid transfected mouse B cells containing exon 2 genomic DNA constructs spanning −189 to +101 bp showed strong promoter activity when stimulated with IL-4 and anti-CD40 antibodies (FIG. 22B); non-stimulated cells showed little luciferase activity (data not shown). Which the 5' NF-kB cis-sequence appears to be important for promoter activation, because constructs in which the 3' NF-kB site has been omitted still exhibit strong promoter activity (FIG. 22B), in contrast to the much lower activity observed reporter constructs in which the 5' NF-kB site has been deleted (FIG. 22B). Furthermore, it is In addition to NF-kB, STAT6 binding might also be involved in the significant increase of the exon 2 transcript observed in B cells stimulated with IL-4/anti-CD40, because two putative STAT6 sites are located at −6 and +12 bp of the TSS(+1) of exon 2 (FIG. 15B). However, as reported previously (Thieu, V. T. et al., Journal of Leukocyte Biology, 2007, 82:370-379), NF-kB may be required for binding of STAT6, supported by the minimal to no promoter activity observed in the exon 2 reporter constructs in which one or both STAT6 sites are present but the 5' NF-kB site has been deleted (FIG. 22B). However, further analysis may be undertaken to determine the Cnr2 regulatory relationship of these cis-sequences for the trans-factors under these conditions in B cells.

In addition to the variation of $CB_2$ transcript expression seen in activated B cells, differences in $CB_2$ transcript expression was also observed in B cell development. RACE and RT-qPCR analysis of $CB_2$ transcript expression in three mouse B cell lines representing different stages of development showed that pre-B cells expressed only the exon 1a variant, whereas immature and mature B cells express all three variants, though at varying levels. Expression of the transcript variants was greatest in the immature B cells, notably the exon 1a variant, whereas mature B cells expressed mainly the exon 1b variant (FIGS. 29A-B). The results described herein are in line with a recent report in which $CB_2$ transcript expression was higher in immature B cells located in bone marrow sinusoids when compared to other developmental stages and suggested a function for $CB_2$ in the formation of the B cell repertoire (Pereira, J. P. et al., Nature Immunology, 2009, 10:403-411).

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. A method of reducing the expression of a B cell $CB_2$ receptor gene, comprising contacting the B cell with one or more inhibitory nucleic acid molecules comprising a nucleic acid sequence that targets a sequence (nucleic acid target sequence within or overlapping with the transcription start site associated with the B cell $CB_2$ receptor gene promoter region within the cell, thereby reducing expression of the B cell $CB_2$ receptor gene.

2. The method of claim 1, wherein the one or more inhibitory nucleic acid molecules are selected from among an interfering RNA (RNAi) molecule, an antisense oligonucleotide, a ribozyme, and a construct that causes targeted deletion of the $CB_2$ receptor gene.

3. The method of claim 1, wherein the nucleic acid target sequence comprises at least one region selected from among the transcription start site (tss) for human exon 1, or at least a portion of the 5' untranslated region (UTR) for human exon 1.

4. The method of claim 1, wherein the nucleic acid target sequence comprises at least one region selected from among the transcription start site (tss) for mouse exon 1a, mouse exon 1b, or mouse exon 2, or at least a portion of the 5' UTR for mouse exon 1a, mouse exon 1b, or mouse exon 2.

5. The method of claim 1, wherein the one or more inhibitory nucleic acid molecules are contacted with the cell in vivo, and wherein said contacting comprises administering the one or more inhibitory nucleic acid molecules to a subject.

6. The method of claim 5, wherein said administering results in regulation of an immunoglobulin E (IgE)-mediated allergic response in the subject.

7. The method of claim 1, wherein the cell is a human or mouse cell.

8. The method of claim 1, wherein the one or more inhibitory nucleic acid molecules are contacted with the cell in vitro.

9. The method of claim 1, wherein the nucleic acid target sequence comprises a region surrounding and including the 5' end of human exon 1.

10. The method of claim 1, wherein the nucleic acid target sequence comprises a region surrounding and including the 5' end of mouse exon 1a, the 5' end of mouse exon 1b, or the 5' end of mouse exon 2.

11. The method of claim 1, wherein the nucleic acid target sequence comprises a region surrounding and including the 5' end of mouse exon 1b.

12. The method of claim 1, wherein the nucleic acid target sequence comprises a region surrounding and including the 5' end of exon 2.

13. The method of claim 1, wherein the nucleic acid target sequence is a sequence within or overlapping with nucleotides 83-117 of SEQ ID NO:121.

14. The method of claim 1, wherein the nucleic acid sequence of the one or more inhibitory nucleic acid molecules is complementary to a sequence within or overlapping with nucleotides 83-117 of SEQ ID NO:121.

15. The method of claim 1, wherein the nucleic acid sequence of the one or more inhibitory nucleic acid molecules is sufficiently complementary to a sequence within, or overlapping with, nucleotides 83-117 of SEQ ID NO:121 to direct target-specific RNA interference (RNAi).

16. The method of claim 1, wherein the nucleic acid target sequence is a sequence within or overlapping with:
nucleotides 1-14 of SEQ ID NO:118, or
nucleotides 1-294 of SEQ ID NO:119, or
nucleotides 1-172 of SEQ ID NO:120.

17. The method of claim 1, wherein the nucleic acid sequence of the one or more inhibitory nucleic acid molecules is complementary to a sequence within or overlapping with:
nucleotides 1-14 of SEQ ID NO:118, or
nucleotides 1-294 of SEQ ID NO:119, or
nucleotides 1-172 of SEQ ID NO:120.

18. The method of claim 1, wherein the nucleic acid sequence of the one or more inhibitory nucleic acid molecules is sufficiently complementary to a sequence within or overlapping with:
nucleotides 1-14 of SEQ ID NO:118, or
nucleotides 1-294 of SEQ ID NO:119, or
nucleotides 1-172 of SEQ ID NO:120 to direct target-specific RNA interference (RNAi).

* * * * *

UNITED STATES PATENT AND TRADEMARK OFFICE
CERTIFICATE OF CORRECTION

PATENT NO. : 8,541,386 B2  
APPLICATION NO. : 12/859744  
DATED : September 24, 2013  
INVENTOR(S) : Thomas W. Klein et al.

Page 1 of 1

It is certified that error appears in the above-identified patent and that said Letters Patent is hereby corrected as shown below:

In the Specifications

Column 12
Line 37, "elements which" should read --elements, which--

Column 34
Line 26, "CDR chain" should read --CD3ε chain--

Column 41
Line 57, "CDR" should read --CD3ε--
Line 61, "CDR" should read --CD3ε--

Signed and Sealed this
Fourth Day of March, 2014

Michelle K. Lee
*Deputy Director of the United States Patent and Trademark Office*